US011891451B2

(12) United States Patent
Callewaert et al.

(10) Patent No.: US 11,891,451 B2
(45) Date of Patent: Feb. 6, 2024

(54) GLYCOSYLATION OF VARIABLE IMMUNOGLOBULIN DOMAINS

(71) Applicants: VIB VZW, Ghent (BE); UNIVERSITEIT GENT, Ghent (BE)

(72) Inventors: Nico Callewaert, Nevele (BE); Bram Laukens, Ghent (BE); Loes Van Schie, Ghent (BE); Wander Van Breedam, Antwerp (BE); Wim Nerinckx, Astene (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 319 days.

(21) Appl. No.: 16/612,476

(22) PCT Filed: May 9, 2018

(86) PCT No.: PCT/EP2018/062154
§ 371 (c)(1),
(2) Date: Nov. 11, 2019

(87) PCT Pub. No.: WO2018/206734
PCT Pub. Date: Nov. 15, 2018

(65) Prior Publication Data
US 2020/0148790 A1      May 14, 2020

(30) Foreign Application Priority Data
May 11, 2017   (EP) ..................................... 17170661

(51) Int. Cl.
*C07K 16/40*      (2006.01)
*A61K 47/68*      (2017.01)

(52) U.S. Cl.
CPC .......... *C07K 16/40* (2013.01); *A61K 47/6871* (2017.08); *C07K 2317/22* (2013.01); *C07K 2317/41* (2013.01); *C07K 2317/565* (2013.01); *C07K 2317/567* (2013.01); *C07K 2317/569* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2006/0292149 A1* 12/2006 Saint-Remy .............. A61P 9/10
514/165

FOREIGN PATENT DOCUMENTS

| WO | WO-0104269 A1 * | 1/2001 | ....... A61K 39/39533 |
| WO | 2016150845 A1 | 9/2016 | |
| WO | WO-2016150845 A1 * | 9/2016 | ............. C07K 16/18 |

OTHER PUBLICATIONS

Harmsen et al., Antibodies 2013, 2, 168-192; doi:10.3390/antib2020168.*
Melo-Braga et al., bioRxiv preprint doi: https://doi.org/10.1101/2021.04.11.439351; posted Apr. 12, 2021, 37 pages.*
Dondelinger et al., Front Immunol. Oct. 16, 2018;9:2278. doi: 10.3389/fimmu.2018.02278. eCollection 2018. PMID: 30386328.*
Antibodies from www.bioinf.org.uk:Dr. Andrew C.R. Martin's Group, downloaded Jul. 11, 2018, nine pages.*
Stryer, L. Biochemistry, 4th edition, W.H. Freeman and Company, 1995, pp. 18-23.*
Janeway et al., Immunobiology, 3rd edition, 1997, Garland Publishing Inc., pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Ghahroudi et al., FEBS Letters Sep. 15, 1997; 414(3): 521-526.*
Frenken et al., J Biotechnol. Feb. 28, 2000;78(1):11-21. doi: 10.1016/s0168-1656(99)00228-x.*
Harmsen et al., Vaccine. Sep. 30, 2005;23(41):4926-34. doi: 10.1016/j.vaccine.2005.05.017.*
Sagt et al., Appl Environ Microbiol. Nov. 2000;66(11):4940-4. doi: 10.1128/AEM.66.11.4940-4944.2000.*
Harmsen, M.M, et al. "Isolation of Panels of Llama Single-Domain Antibody Fragments Binding All Nine Neuraminidase Subtypes of Influenza a Virus." Antibodies. 2.2 (2013): 168-192.
Kubala, Marta H., et al. "Structural and Thermodynamic Analysis of the GFP:GFP-Nanobody Complex." Protein Science, vol. 19, No. 12, 2010, pp. 2389-2401.
Oyen, David, et al. "Constraining Enzyme Conformational Change by an Antibody Leads to Hyperbolic Inhibition." Journal of Molecular Biology, vol. 407, No. 1, 2011, pp. 138-148.
PCT International Search Report and Written Opinion, Application No. PCT/EP2018/062154, dated Sep. 3, 2018, 16 pages.

* cited by examiner

Primary Examiner — Michael Szperka
(74) Attorney, Agent, or Firm — Patent Law Works LLP

(57) ABSTRACT

The present invention provides nucleotide sequences encoding polypeptides comprising immunoglobulin variable domains with engineered glycosylation acceptor sites. Specifically, the invention provides immunoglobulin variable domain proteins modified with selected glycans and specific glycan-conjugates thereof. Also provided herein are methods for the production of glycosylated immunoglobulin variable domains and glycan-conjugates thereof.

13 Claims, 16 Drawing Sheets
Specification includes a Sequence Listing.

Figure 3

CLUSTAL O(1.2.1) multiple sequence alignment

```
reference-nanobody-3K74      --QLQESGGGLVQPGGSLRLSCAASGFTFHMYSMYAVRRAPGKGLEWVSHINPGGIITKY
nanobody-GBP                 QVQLVESGGALVQPGGSLRLSCAASGFPVIRYSPHRYRQAPGKEREWVAGISSAGDRSSY
                              *  .*************** .*.* * * *;**  *; ;. .* ;.* reference-nanobody-3K74      AESVKGRFTISRDNAKNTLYLQMNSLTSEDTAVYYCAKDWATGLAKRGQGTQVTVSS---
nanobody-GBP                 EDSVKGRFTISRDDARNTVYLQMNSLKPEDTAVYYCHMI--VGFEYWGQGTQVTVSSHHH
                              ;***********;*;;**.*****  ;  .*;  ********** reference-nanobody-3K74      ---
nanobody-GBP                 HHH
```

Figure 4

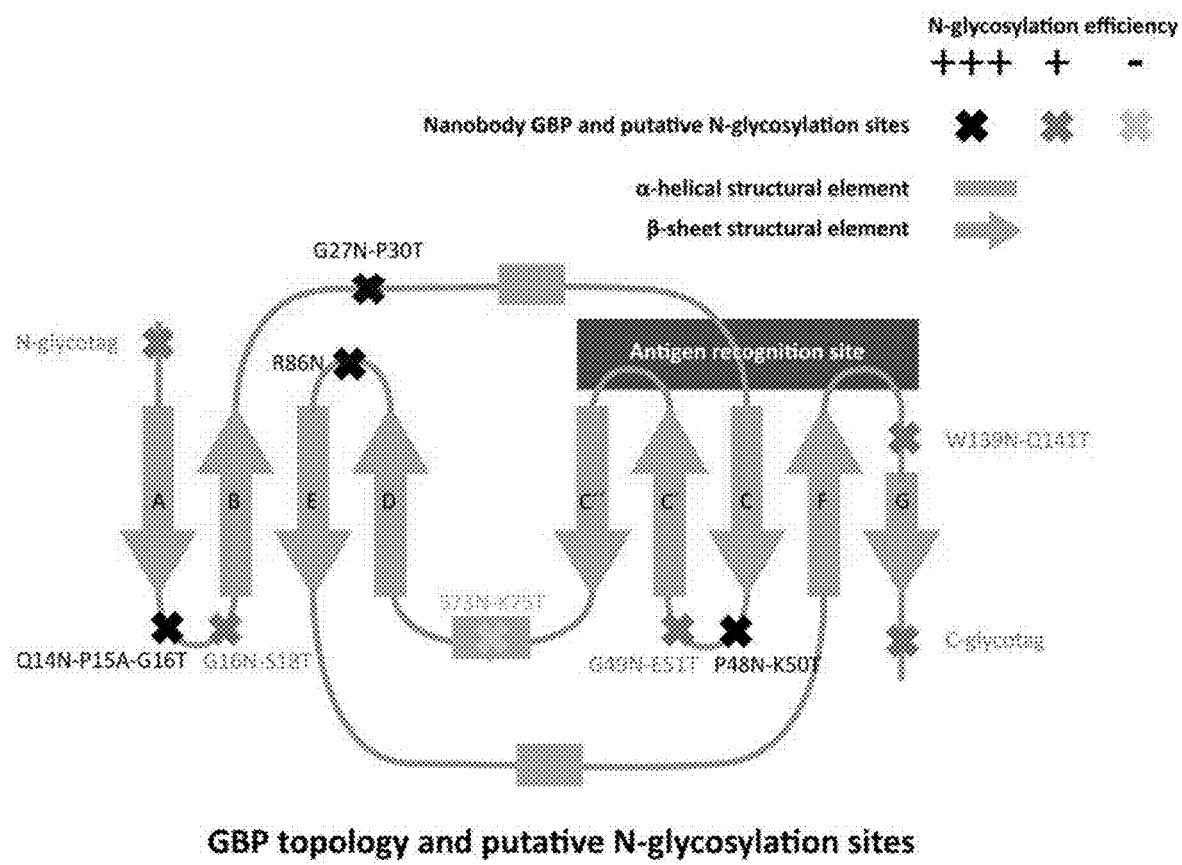

GBP topology and putative N-glycosylation sites

Figure 12
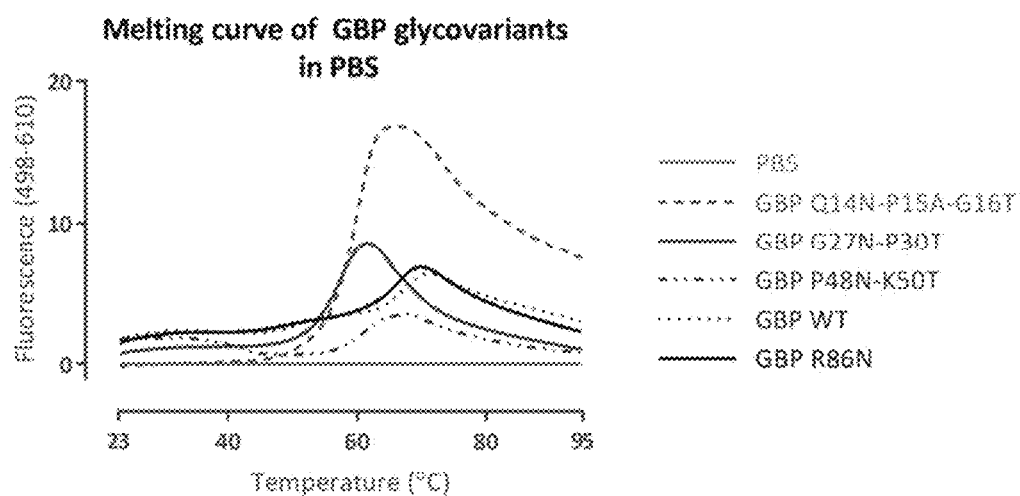
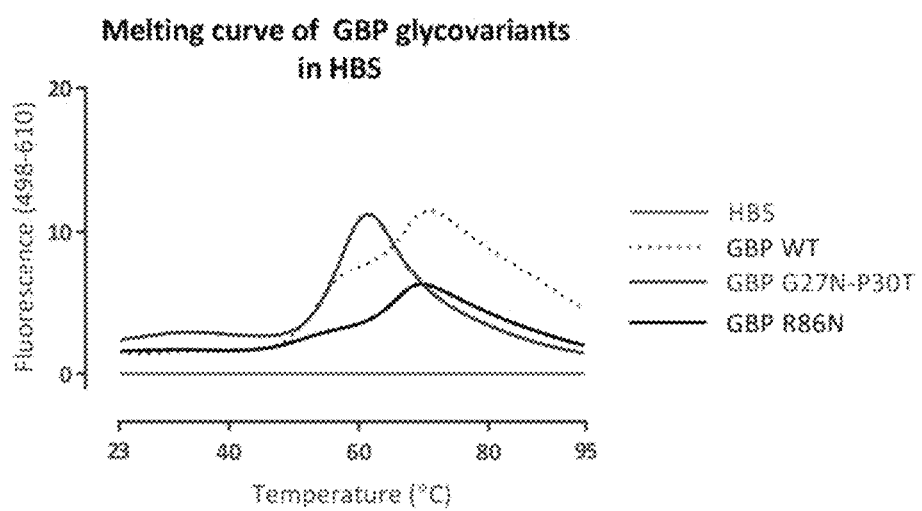

Figure 15

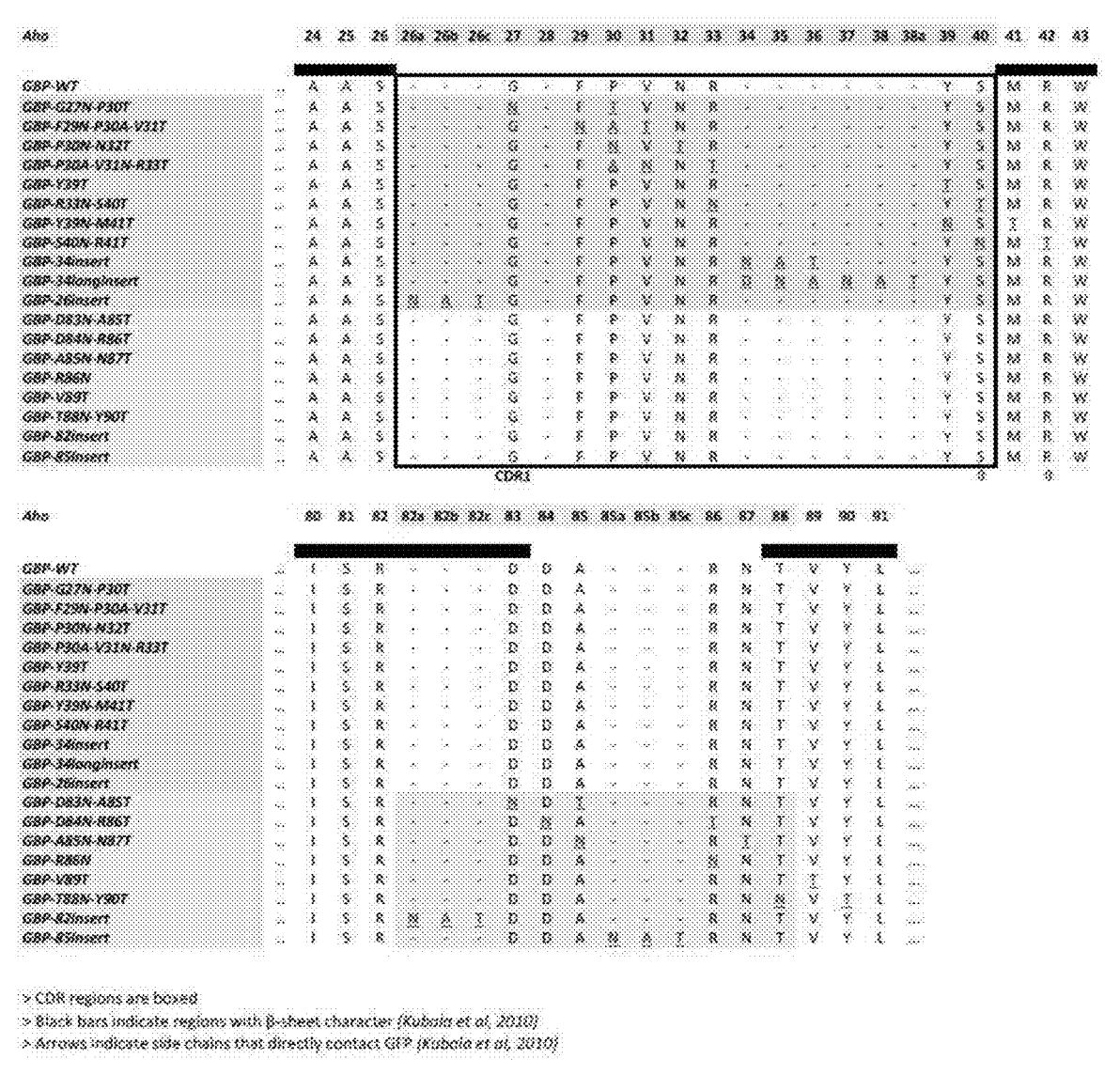

> CDR regions are boxed
> Black bars indicate regions with β-sheet character (Kubala et al, 2010)
> Arrows indicate side chains that directly contact GFP (Kubala et al, 2010)

GLYCOSYLATION OF VARIABLE IMMUNOGLOBULIN DOMAINS

FIELD OF THE INVENTION

The present application relates to the field of glycosylation engineering, more particularly to immunoglobulin domains and glycosylated derivatives thereof. In particular the invention provides nucleotide sequences encoding polypeptides comprising immunoglobulin variable domains with engineered glycosylation acceptor sites. Accordingly, the invention provides immunoglobulin variable domain proteins modified with selected glycans and specific glycan-conjugates thereof. Also provided herein are methods for the production of glycosylated immunoglobulin variable domains and glycan-conjugates thereof.

BACKGROUND TO THE INVENTION

The field of recombinant antibody technology has rapidly progressed during the last two decades, mainly because of the interest in their human therapeutic use. The ability to select specific human antibodies by display technologies and to improve their affinity, stability, and expression level by molecular evolution has further boosted the field. Whole antibodies are complex molecules that consist of heavy and light chains. Although isolated antibody heavy and light chains can retain antigen-binding specificity, their affinity and solubility is often reduced. However, the paired N-terminal variable domains of heavy (VH) and light (VL) chains are sufficient for antigen binding. Such antibody fragments can be produced as monovalent antibody fragment (Fab) or as single-chain Fv (scFv) where the VH and VL domains are joined by a polypeptide linker. The serendipitous discovery that camelids produce functional antibodies devoid of light chains (Hamers-Casterman et al (1993) *Nature* 363:446-448)) formed a new way of thinking in the field because it was subsequently shown that their single N-terminal domain (VHH, also referred to as Nanobody®) binds antigen without requiring domain pairing. These heavy-chain only antibodies also lack the CH1 domain, which in a conventional antibody associates with the light chain and to a lesser degree interacts with the VH domain. Such single-domain antibodies were later also identified in particular cartilaginous fish (Greenberg et al (1995) *Nature* 374:168-173) and together with the VHHs are often designated as immunoglobulin single variable domain antibodies (ISVD). ISVDs present interesting therapeutic possibilities owing to their small size, high stability, ease of modification by genetic fusions and good production levels in microorganisms. When Nanobodies® are produced in eukaryotic cells about a tenth of them is glycosylated (see Functional Glycomics, Jun. 11, 2009). However, glycosylation is generally avoided for the production of ISVDs and hence glycosylation acceptor sites are mutated as the presence of a glycan can introduce heterogeneity, but it can also interfere with folding and antigen recognition. The small size of ISVDs is also a therapeutic disadvantage because of their rapid clearance from circulation when administered to patients. On the other hand the small size of ISVDs offers opportunities for coupling ISVDs to half-life extension molecules, or coupling to specific drugs (e.g. formation of antibody-drug conjugates) or tracers. A variety of coupling methods are described in the art (e.g. especially applied in the field of the modification of monoclonal antibodies) and these technologies focus for example on conjugation via primary amine groups (lysine residues and N-terminus) or via cysteines, by acylation or alkylation, respectively. However, site-control of conjugation is generally low and full homogeneity is seldom obtained. Glycan-specific conjugation of monoclonal antibodies offers more homogeneity as described by Synaffix BV (see for example WO2014065661, WO2015057065 and WO2015057064) but this strategy suffers from the fact that the glycans have to be prepared in vitro before they are suitable for further chemical coupling. It would be desirable to identify specific sites in ISVDs which can be modified with glycan structures which do not encumber the binding or folding functions of these ISVDs and which would lead to an efficient glycosylation and result in homogeneous, ready-to-use-for-chemical-coupling glycan structures when produced in a suitable production system. In the prior art it was shown that modification of ISVDs with glycans is useful to prevent binding to pre-existing anti-VH autoantibodies (see for example WO2016150845). However, no specific design strategy for the introduction of glycosylation sites was used and the positions were arbitrarily chosen and mainly focused on the exposed C-terminal region of the ISVDs. As a consequence, the influence of the presence of glycans on the specific properties of an ISVD as well as the efficiency of glycosylation are currently unpredictable and have to be evaluated on an individual basis.

SUMMARY OF THE INVENTION

An important object of the present application is to provide polypeptides comprising immunoglobulin variable domains (IVDs), wherein the IVDs have glycosylation acceptor sites present in specifically selected regions which have been identified via a rational design approach. The presence of these specific glycosylation acceptor sites at specific regions in an IVD allows for efficient glycosylation without encumbering the binding affinities of the IVDs with their ligand and without interfering with the folding of the IVDs. Importantly, IVDs can be recombinantly produced in suitable host cells comprising homogenous forms of glycans at specific positions which can be further modified with a variety of moieties as herein explained further.

Thus, according to a first aspect, the following is provided: a nucleotide sequence encoding a polypeptide comprising an IVD, wherein the IVD comprises an amino acid sequence that comprises 4 framework regions (FR) and 3 complementarity determining regions (CDR) according to the following formula (1): FR1-CDR1-FR2-CDR2-FR3-CDR3-FR4 (1); or any suitable fragment thereof, wherein the IVD has a glycosylation acceptor site present at any of amino acids 83 to 88 and/or at any of amino acids 27 to 40 of the IVD (according to AHo numbering convention). In a particular aspect said IVD is an immunoglobulin single variable domain. The glycosylation acceptor site of the IVD can be an asparagine residue that can be N-glycosylated. Particularly, the glycosylation acceptor site of said IVD contains an NXT, NXS, NXC or NXV motif (wherein X can be any amino acid except proline (P)) such that the asparagine residue of the NXT/NXS/NXC/NXV motif is present at any of positions 83 to 88 and/or at any of positions 27 to 40 of the IVD (according to AHo numbering convention). In specific embodiments the IVD has an additional glycosylation acceptor site in the IVD, such as position 14 and/or 48 (according to AHo numbering convention).

In another aspect, a polypeptide comprising an IVD is provided, which is encoded by a nucleotide sequence of the invention.

According to other aspects expression vectors comprising said nucleotide sequence and a cell comprising the expression vector are provided.

A recombinant cell is, according to particular embodiments, a higher eukaryotic cell, such as a mammalian cell or a plant cell, a lower eukaryotic cell, such as a filamentous fungus cell or a yeast cell, or in certain conditions also a prokaryotic cell. Of particular relevance are glyco-engineered cells, particularly glyco-engineered lower eukaryotic cells.

More particularly, the higher eukaryotic cells according to the invention are vertebrate cells, in particular mammalian cells. Examples include, but are not limited to, CHO cells or HEK293 cells (e.g. HEK293S cells).

Using these cells IVDs can be produced which are modified with glycans at specific rationally chosen sites. Glyco-engineered cells are of particular advantage as they are favorable for the production of IVDs modified with particularly desired glycans and/or homogeneous glycans. This homogenous glycosylation profile is highly desirable as a product is obtained whose properties are well predictable.

Moreover, the above described cells are useful for the production of IVDs which are directly in the cell modified with GlcNAc, LacNAc, or Sialyl-LacNAc glycans being favorable for conjugation. Moreover, employment of these cells leads to IVDs with homogenous glycosylation profiles. Thus, particular benefits over conventional approaches are achieved as the obtained products are highly homogenous. This is in contrast with conventional approaches which typically require in vitro enzymatic treatment of heterogeneous glycans to provide GlcNAc, Gal, or Sia residues as starting points for further modification. Besides high costs, in vitro enzymatic treatment might risk incomplete processing and thus a heterogeneous product. Another conventional approach is based on direct processing of heterogeneously glycosylated proteins and accordingly, the resulting products again lack homogeneity.

According to specific embodiments, the polypeptide according to the invention comprises an IVD, which is glycosylated. The glycosylation can, according to specific embodiments, comprise one or more glycans with a terminal GlcNAc, GalNAc, Galactose, Sialic Acid, Glucose, Glucosamine, Galactosamine, Bacillosamine, Mannose or Mannose-6-P sugar or a chemically modified monosaccharide such as GalNAz, GlcNAz, or azido-Sialic acid present in one or more glycans. According to other specific embodiments, the glycosylation consists of one or more glycans selected from the list consisting of GlcNAc, LacNAc (=GlcNAc-Gal), sialyl-LacNAc, Man5GlcNAc2, Man8GlcNAc2, Man9GlcNAc2, complex glycans, hybrid glycans and GlcNAz, GlcNAc-GalNAz, and LacNAc-Azido-Sialic acid (see Alan D. McNaught (1996) *Pure & Appl. Chem. Vol.* 68, No 10, 1919-2008 for Nomenclature of Carbohydrates). IVDs modified at certain positions with the above described glycans are particularly useful for glycan-specific conjugation. Especially a glycosylation profile consisting of GlcNAc, LacNAc, or sialyl-LacNAc is of advantage for site-specific conjugation.

In specific embodiments, an IVD conjugate is provided comprising a polypeptide according to the invention and a conjugated moiety, which is conjugated to the glycan.

IVDs modified with glycans at rationally chosen positions are an ideal starting point for glycan-based conjugation. Linkage of a moiety to a glycan present on an IVD for example allows for the production of IVD conjugates, wherein the ratio of IVD and conjugated moiety is well-defined.

Even more advantageous are IVDs modified with homogenous glycans allowing for particularly efficient conjugation. Conjugation can be performed either chemically (e.g. using periodate oxidation of the glycan component and subsequent conjugation via methods known in the art such as oxime ligation, hydrazone ligation, or via reductive amination) or enzymatically (e.g. using Galactose Oxidase to oxidize Galactose and subsequent conjugation via oxime ligation, hydrazone ligation, or via reductive amination). Alternatively, tagged glycan residues may be incorporated to allow subsequent conjugation reactions (e.g. incorporation of GalNAz in the glycan chain using a mutant galactosyltransferase, and subsequent conjugation reaction via click chemistry).

The conjugated moiety can comprise a half-life extending moiety, a therapeutic agent, a detection unit or a targeting moiety. The opportunities to use the glycans on IVDs according to the invention as a bio-orthogonal handle for conjugation to drugs, tracers, and the like via glycan conjugation methodologies are not limited to the examples described herein.

Also provided in the application are methods to produce polypeptides comprising an IVD and IVD-conjugates as described herein. Particularly, methods are provided for producing polypeptides comprising an IVD according to the invention in a suitable cell, comprising the steps of:
  providing a suitable cell
  introducing an expression vector comprising a nucleotide sequence encoding a polypeptide according to the invention in said cell
  expressing the polypeptide comprising an IVD in suitable conditions; and
  isolating the polypeptide comprising an IVD.

Said method can further comprise the step of linking the conjugated moiety to the polypeptide.

The present invention also relates to a composition comprising a polypeptide comprising an IVD or a conjugate thereof. Preferably, said composition is a pharmaceutical composition. Even more preferably, said composition further comprises at least one pharmaceutically acceptable carrier, diluent, excipient or adjuvant, and optionally comprises one or more polypeptides of the invention.

BRIEF DESCRIPTION OF THE FIGURES

FIG. 3: Amino acid alignment of nanobody GBP (SEQ ID NO:9) with nanobody 3K74 (SEQ ID NO:1)

FIG. 4: Specific sites selected for introduction of N-linked glycosylation signatures in the GBP nanobody are depicted (numbering in the figure refers to the aHo numbering scheme; for alternative (Kabat) numbering see FIG. 9 or 11). N-glycosylation efficiency was estimated based on His-specific western blot data or mass spectrometry data.

FIG. 12: Melting curves of GBP glycovariants. Nanobodies produced in *Pichia pastoris* GlycoSwitchM5 (GSM5) (Man5GlcNAc2 glycans) and purified via IMAC and SEC, eluted in either phosphate-buffered saline (PBS, top) or HEPES-buffered saline (HBS, bottom). Thermal shift assay using SYPRO Orange dye in a qPCR machine.

FIG. 15: Partial sequence alignment of nanobody GBP (SEQ ID NO: 41) with glycovariants (GBT-G27N-P30T (SEQ ID NO:42); GBT-F29N-P30A-V31T (SEQ ID NO:43); GBT-P30N-N32T (SEQ ID NO:44); GBT-P30A-V31N-R33T (SEQ ID NO:45); GBT-Y39T (SEQ ID NO:46); GBT-R33N-S40T (SEQ ID NO:47); GBT-Y39N-M41T (SEQ ID NO:48); GBT-S40N-R41T (SEQ ID NO:49); GBT-34insert (SEQ ID NO:50); GBT-34longinsert (SEQ ID NO:51); GBT-26insert (SEQ ID NO:52); GBT-D83N-A85T (SEQ ID NO:53); GBT-D84N-R86T (SEQ ID NO:54); GBT-A85N-N87T (SEQ ID NO:55); GBT-R86N (SEQ ID NO:56); GBT-V89T (SEQ ID NO:57); GBT-T88N-Y90T (SEQ ID NO:58); GBT-82insert (SEQ ID NO:59); GBT-85insert (SEQ ID NO:60)) in region 27-40 (top) and region 83-88 (bottom).

DETAILED DESCRIPTION

Figure 1:
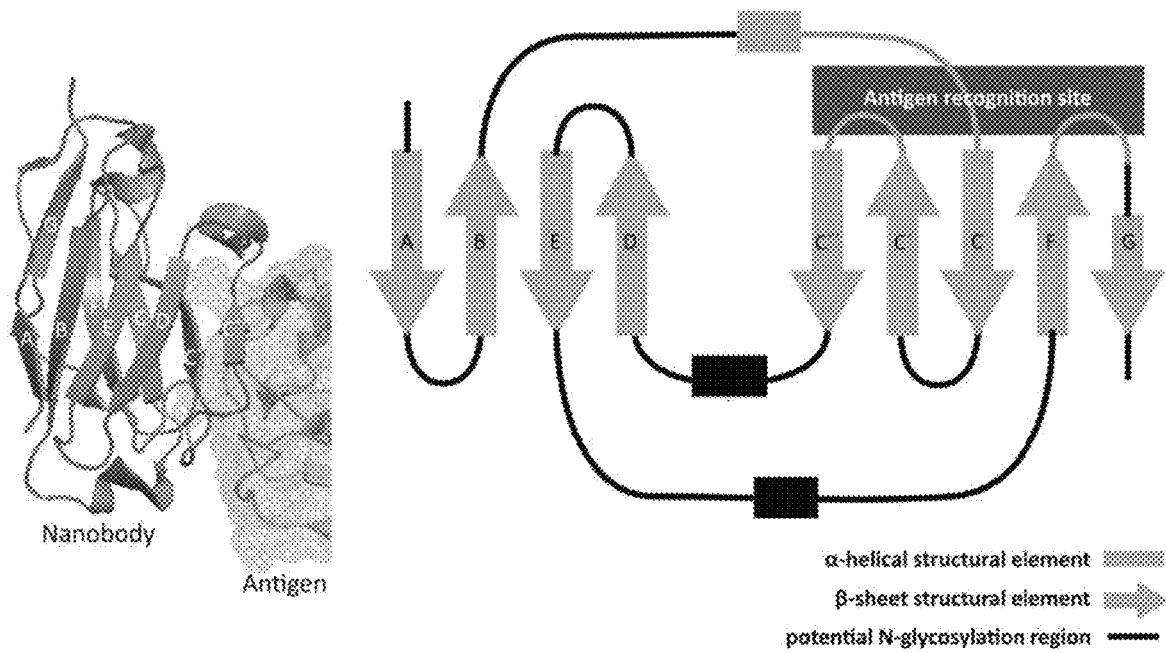
FIG. 1: Tertiary structure (left) and secondary structure topology (right) of a representative ISVD, here a nanobody (chain B from PDB entry id: 3K74). Several hypothetical regions were determined for N-linked glycosylation sequon introduction (in the right panel, 9 regions are depicted in black).
Figure 2:
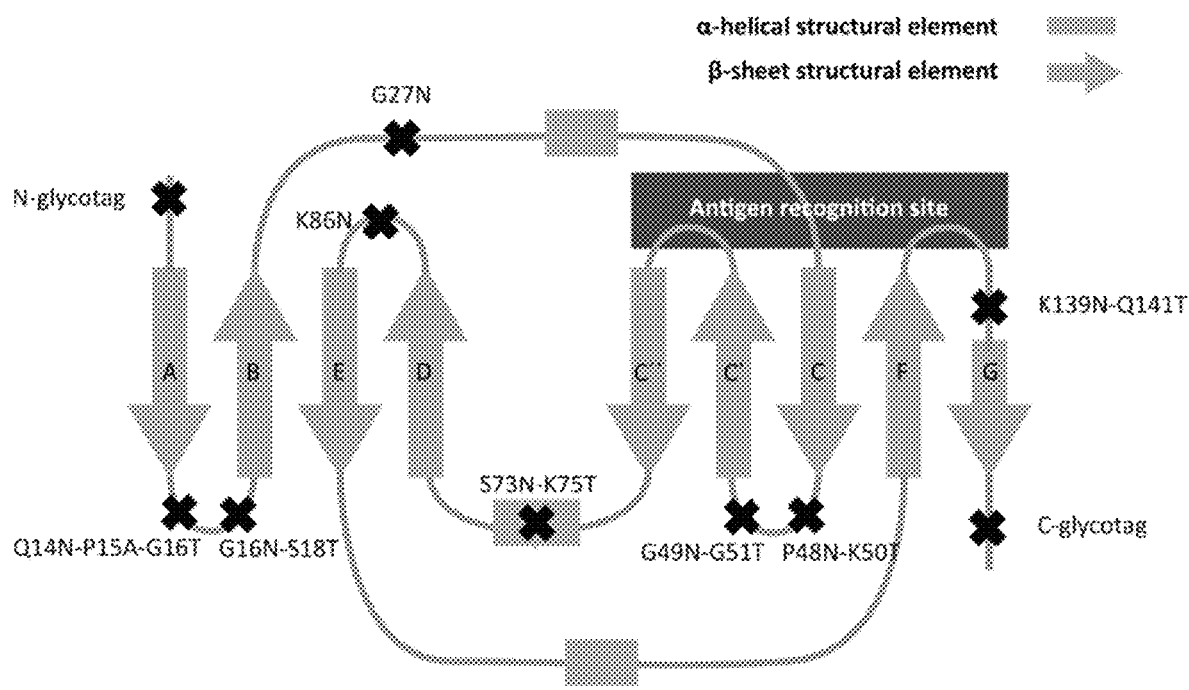
FIG. 2: Ten specific sites (indicated by X) selected for introduction of N-linked glycosylation sequons in reference nanobody PDB id: 3K74 (numbering in the figure refers to the aHo numbering scheme; for alternative (Kabat) numbering see FIG. 9).

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

As used herein, the term "nucleotide sequence" refers to a polymeric form of nucleotides of any length, either deoxyribonucleotides or ribonucleotides, or analogs thereof. Nucleotide sequences may have any three-dimensional structure, and may perform any function, known or unknown. Non-limiting examples of nucleotide sequences include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleotide sequence may be linear or circular.

As used herein, the term "polypeptide" refers to a polymeric form of amino acids of any length, which can include coded and non-coded amino acids, chemically or biochemically modified or derivatized amino acids, and polypeptides having modified peptide backbones. Polypeptide sequences can be depicted with the single-letter (or one letter) amino acid code or the three letter amino acid code as depicted here below:

| Amino acid | Three letter code | One letter code |
|---|---|---|
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" (abbreviated as "ISVD"), equivalent to the term "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, V H H domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al (1993) *Nature* 363: 446-448). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHHs and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dabs", "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

Figure 9:
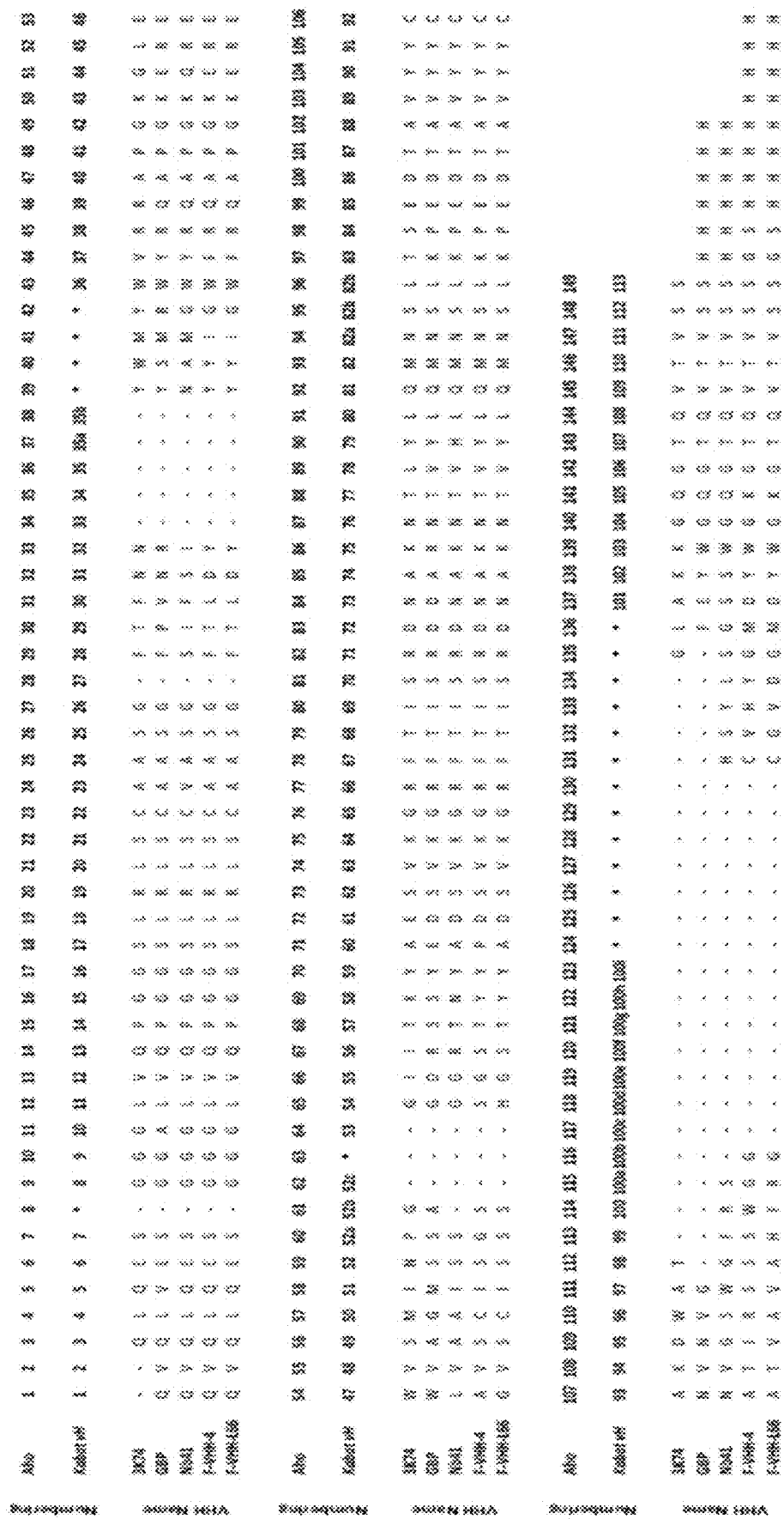
FIG. 9: Sequence alignment of nanobodies Nb 41 (SEQ ID NO:17), F-VHH-4 (SEQ ID NO:25), and F-VHH-L66 (SEQ ID NO:26) with nanobodies GBP (SEQ ID NO:9) and 3K74 (SEQ ID NO:1).
Figure 11:
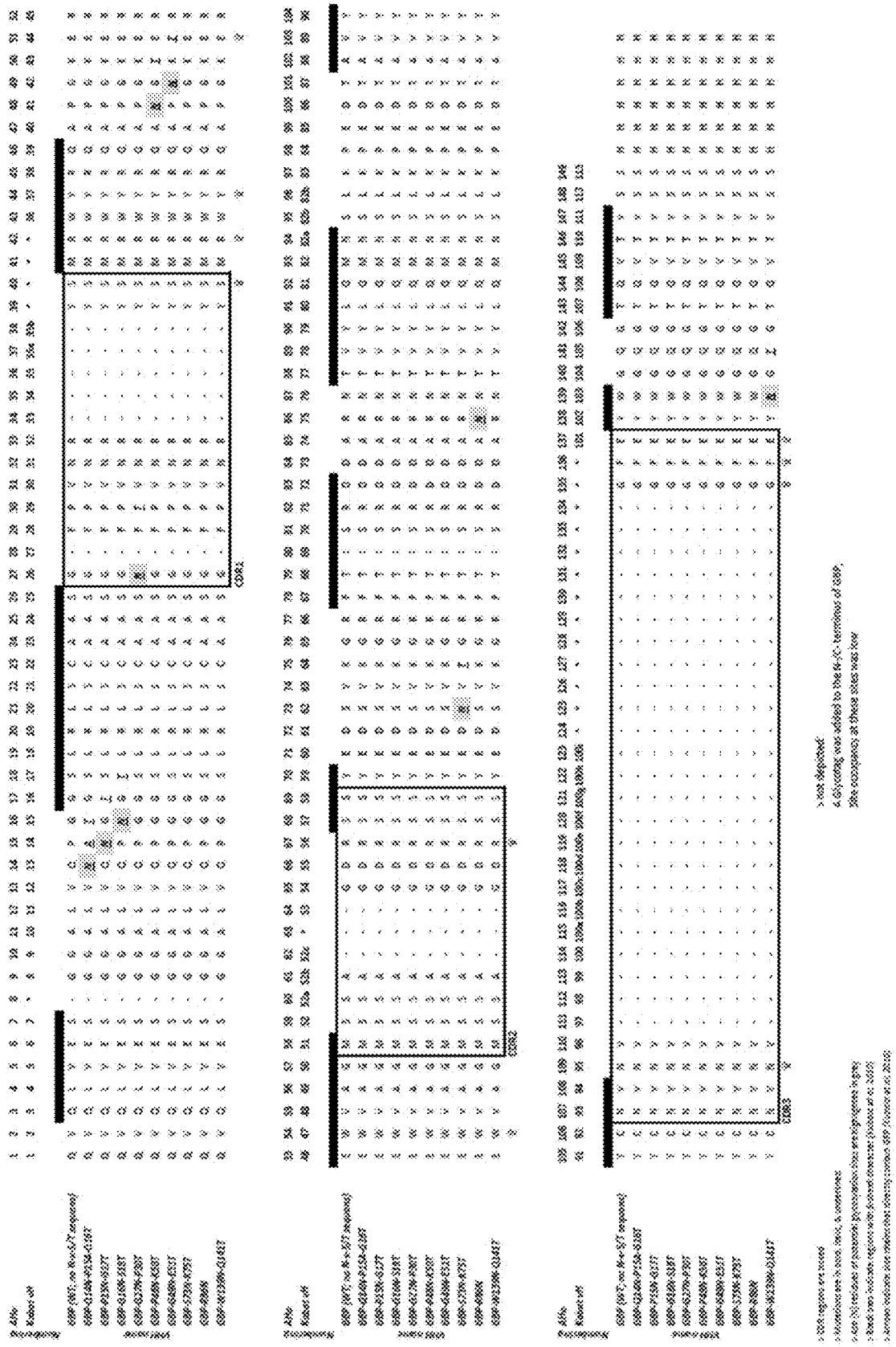
FIG. 11: Overview of nanobody GBP glycosylation sites with the sequences for GBP (SEQ ID NO:9); GBP-Q14N-P15A-G16T (SEQ ID NO:32); GBP-P15N-G17T (SEQ ID NO:33); GBP-G16N-S15T (SEQ ID NO:34); GBP-G27N-P30T (SEQ ID NO:35); GBP-P48N-K50T (SEQ ID NO:36); GBP-G49N-E51T (SEQ ID NO:37); GBP-S73N-K75T (SEQ ID NO:38); GBP-R56N (SEQ ID NO:39); and GBP-W139N-Q141T (SEQ ID NO:40).

For numbering of the amino acid residues of an IVD different numbering schemes can be applied. For example, numbering can be performed according to the AHo numbering scheme for all heavy (VH) and light chain variable domains (VL) given by Honegger, A. and Plückthun, A. (*J. Mol. Biol.* 309, 2001), as applied to VHH domains from camelids. Alternative methods for numbering the amino acid residues of VH domains, which can also be applied in an analogous manner to VHH domains, are known in the art. For example, the delineation of the FR and CDR sequences can be done by using the Kabat numbering system as applied to VHH domains from camelids in the article of Riechmann, L. and Muyldermans, S., 231(1-2), *J Immunol Methods*. 1999. Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113. An overview of the 2 different numbering schemes applied to the specific nanobodies used in the examples section is depicted in FIG. 9 or 11. However, in the present description and claims, the numbering according to AHo as described above will be followed.

It should be noted that—as is well known in the art for $V_H$ domains and for VHH domains—the total number of amino acid residues in each of the CDRs may vary and may not correspond to the total number of amino acid residues indicated by the Kabat numbering or AHo numbering (that is, one or more positions according to the Kabat numbering or AHo may not be occupied in the actual sequence, or the actual sequence may contain more amino acid residues than the number allowed for by the Kabat numbering or AHo numbering). This means that, generally, the numbering according to Kabat or AHo may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on what is described before, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (*Biotechnology* 10:779-783, 1992), Barbas, et al. (*Proc. Nat. Acad. Sci, USA* 91: 3809-3813, 1994), Shier et al. (*Gene* 169: 147-155, 1995), Yelton et al. (*Immunol.* 155: 1994-2004, 1995), Jackson et al. (*J. Immunol.* 154: 3310-9, 1995), Hawkins et al. (*J. Mol. Biol.* 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

The term "Glycosylation acceptor site" refers to a position within the IVD, which can be N- or O-glycosylated. N-linked glycans are typically attached to asparagine (Asn), while O-linked glycans are commonly linked to the hydroxyl oxygen of serine, threonine, tyrosine, hydroxylysine, or hydroxyproline side-chains.

An "NXT", "NXS", "NXC" or "NXV" motif refers to the consensus sequences Asn-Xaa-Thr/Ser or Asn-Xaa-Cys/Val, wherein Xaa can be any amino acid except proline (Shrimal, S. and Gilmore, R., *J Cell Sci.* 126(23), 2013, Sun, S. and Zhang, H., *Anal. Chem.* 87 (24), 2015). It is well known in the art that potential N-glycosylation acceptor sites are specific to the consensus sequence Asn-Xaa-Thr/Ser or Asn-Xaa-Cys/Val. It has been shown in the art that the presence of proline between Asn and Thr/Ser leads to inefficient N-glycosylation. In a particular aspect, the N-linked glycosylation acceptor site of an IVD or ISVD according to the invention is expanded with aromatic residues like natural or engineered aromatic amino acid residues such as Phenylalanine (F), Tyrosine (Y), Histidine (H) or Tryptophane (W). Such modifications are described i.e. in Price, J. L. et al., *Biopolymers.* 98(3), 2012 and in Murray, A. N. et al., *Chem Biol.* 22(8), 2015. In a more particular embodiment, the aromatic residues are located at position −1 (F/Y/H/W-N-x-T/S), −2 (F/Y/H/W-x1-N-x-T/S), or −3 (F/Y/H/W-x2-x1-N-x-T/S) relative to the Asparagine (N) residue in the N-linked glycosylation sequon (N-x-T/N-x-S) (Murray A N et al (2015) *Chem. Biol.* 22(8):1052-62) and Price J L et al (2012) *Biopolymers* 98(3):195-211). Such modifications are particularly useful to increase glycosylation efficiency of an N-glycosylation acceptor site, glycan homogeneity, and glycoprotein stability.

The term "expression vector", as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Expression vectors generally contain a desired coding sequence and appropriate promoter sequences necessary for the expression of the operably linked coding sequence in a particular host organism (e.g. higher eukaryotes, lower eukaryotes, prokaryotes). Typically, a vector comprises a nucleotide sequence in which an expressible promoter or regulatory nucleotide sequence is operatively linked to, or associated with, a nucleotide sequence or DNA region that codes for an mRNA, such that the regulatory nucleotide sequence is able to regulate transcription or expression of the associated nucleotide sequence. Typically, a regulatory nucleotide sequence or promoter of the vector is not operatively linked to the associated nucleotide sequence as found in nature, hence is heterologous to the coding sequence of the DNA region operably linked to. The term "operatively" or "operably" "linked" as used herein refers to a functional linkage between the expressible promoter sequence and the DNA region or gene of interest, such that the promoter sequence is able to initiate transcription of the gene of interest, and refers to a functional linkage between the gene of interest and the transcription terminating sequence to assure adequate termination of transcription in eukaryotic cells. An "inducible promoter" refers to a promoter that can be switched 'on' or 'off' (thereby regulating gene transcription) in response to external stimuli such as, but not limited to, temperature, pH, certain nutrients, specific cellular signals, et cetera. It is used to distinguish between a "constitutive promoter", by which a promoter is meant that is continuously switched 'on', i.e. from which gene transcription is constitutively active.

A "glycan" as used herein generally refers to glycosidically linked monosaccharides, oligosaccharides and polysaccharides. Hence, carbohydrate portions of a glycoconjugate, such as a glycoprotein, glycolipid, or a proteoglycan are referred to herein as a "glycan". Glycans can be homo- or heteropolymers of monosaccharide residues, and can be linear or branched. N-linked glycans may be composed of GalNAc, Galactose, neuraminic acid, N-acetylglucosamine, Fucose, Mannose, and other monosaccharides, as also exemplified further herein.

In eukaryotes, O-linked glycans are assembled one sugar at a time on a serine or threonine residue of a peptide chain in the Golgi apparatus. Unlike N-linked glycans, there are no known consensus sequences but the position of a proline residue at either −1 or +3 relative to the serine or threonine is favourable for O-linked glycosylation.

"Complex N-glycans" as used in the application refers to structures with typically one, two or more (e.g. up to six) outer branches, most often linked to an inner core structure Man3GlcNAc2. The term "complex N-glycans" is well known to the skilled person and defined in literature. For instance, a complex N-glycan may have at least one branch, or at least two, of alternating GlcNAc and optionally also Galactose (Gal) residues that may terminate in a variety of oligosaccharides but typically will not terminate with a Mannose residue. For the sake of clarity a single GlcNAc, LacNAc, sialyl-LacNAc or an azide-modified version of these present on an N-glycosylation site of a glycoprotein (thus lacking the inner core structure Man3GlcNAc2) is not regarded as a complex N-glycan.

"Hypermannosyl glycans" are N-glycans comprising more than 9 mannose residues. Typically such hypermannosyl glycans are produced in lower eukaryotic cells such as yeast cells, specifically wild type yeast cells such as wild type *Pichia pastoris*. N-glycans produced in yeast cells such as *Pichia pastoris* can also be mannose-6-phosphate modified.

A "higher eukaryotic cell" as used herein refers to eukaryotic cells that are not cells from unicellular organisms. In other words, a higher eukaryotic cell is a cell from (or derived from, in case of cell cultures) a multicellular eukaryote such as a human cell line or another mammalian cell line (e.g. a CHO cell line). Typically, the higher eukaryotic cells will not be fungal cells. Particularly, the term generally refers to mammalian cells, human cell lines and insect cell lines. More particularly, the term refers to vertebrate cells, even more particularly to mammalian cells or human cells. The higher eukaryotic cells as described herein will typically be part of a cell culture (e.g. a cell line, such as a HEK or CHO cell line), although this is not always strictly required (e.g. in case of plant cells, the plant itself can be used to produce a recombinant protein).

By "lower eukaryotic cell" a filamentous fungus cell or a yeast cell is meant. Yeast cells can be from the species *Saccharomyces* (e.g. *Saccharomyces cerevisiae*), *Hansenula* (e.g. *Hansenula polymorpha*), *Arxula* (e.g. *Arxula adeninivorans*), *Yarrowia* (e.g. *Yarrowia lipolytica*), *Kluyveromyces* (e.g. *Kluyveromyces lactis*), or *Komagataella phaffii* (Kurtzman, C. P. (2009) *J Ind Microbiol Biotechnol.* 36(11) which was previously named and better known under the old nomenclature as *Pichia pastoris* and also further used herein. According to a specific embodiment, the lower eukaryotic cells are *Pichia* cells, and in a most particular embodiment *Pichia pastoris* cells. In specific embodiments the filamentous fungus cell is *Myceliopthora thermophila* (also known as C1 by the company Dyadic), *Aspergillus* species (e.g. *Aspergillus nidulans, Aspergillus niger, Aspergillus oryzae, Aspergillus japonicus*), *Fusarium* species (e.g. *Fusarium venenatum*), *Hypocrea* and *Trichoderma* species (e.g. *Trichoderma reesei*).

"Prokaryotic cells" typically refer to non-pathogenic prokaryotes like bacterial cells such as for example *E. coli, Lactococcus* and *Bacillus* species.

According to a particular embodiment, the cell of the present invention is a glyco-engineered cell. A "glyco-engineered cell" refers to a cell that has been genetically modified so that it expresses proteins with an altered N-glycan structure and/or O-glycan structure as compared to in a wild type background. Typically, the naturally occurring modifications on glycoproteins have been altered by genetic engineering of enzymes involved in the glycosylation pathway. In general, sugar chains in N-linked glycosylation may be divided in three types: high-mannose (typically yeast), complex (typically mammalian) and hybrid type glycosylation. Besides that, a variety of O-glycan patterns exist, for example with yeast oligomannosylglycans differing from mucin-type O-glycosylation in mammalian cells. The different types of N- and O-glycosylation are all well known to the skilled person and defined in the literature. Considerable effort has been directed towards the identification and optimization of strategies for the engineering of eukaryotic cells that produce glycoproteins having a desired N- and/or O-glycosylation pattern and are known in the art (e.g. De Pourcq, K. et al., Appl Microbiol Biotechnol. 87(5), 2010). One non-limiting example of such a glyco-engineered expression system is described in patent application WO2010015722 and relates to a (higher or lower) eukaryotic cell expressing both an endoglucosaminidase and a target protein, and wherein the recombinant secreted target proteins are characterized by a uniform N-glycosylation pattern (in particular one single GlcNAc residue (in lower eukaryotes) or a modification thereof such as GlcNAc modified with Galactose (LacNAc) or sialyl-LacNAc (in mammalian cells). Also encompassed are cells genetically modified so that they express proteins or glycoproteins in which the glycosylation pattern is human-like or humanized (i.e. complex-type glycoproteins). This can be achieved by providing cells, in particular lower eukaryotic cells, having inactivated endogenous glycosylation enzymes and/or comprising at least one other exogenous nucleic acid sequence encoding at least one enzyme needed for complex glycosylation. Endogenous glycosylation enzymes which could be inactivated include the alpha-1,6-mannosyltransferase Och1p, Alg3p, alpha-1,3-mannosyltransferase of the Mnn1p family, beta-1,2-mannosyltransferases. Enzymes needed for complex glycosylation include, but are not limited to: N-acetylglucosaminyl transferase I, N-acetylglucosaminyl transferase II, mannosidase II, galactosyltransferase, fucosyltransferase and sialyltransferase, and enzymes that are involved in donor sugar nucleotide synthesis or transport. Still other glyco-engineered cells, in particular yeast cells, that are envisaged here are characterized in that at least one enzyme involved in the production of high mannose structures (high mannose-type glycans) is not expressed. Enzymes involved in the production of high mannose structures typically are mannosyltransferases. In particular, alpha-1,6-mannosyltransferases Och1p, Alg3p, alpha-1,3-mannosyltransferase of the Mnn1p family, beta-1,2-mannosyltransferases may not be expressed. Thus, a cell can additionally or alternatively be engineered to express one or more enzymes or enzyme activities, which enable the production of particular N-glycan structures at a high yield. Such an enzyme can be targeted to a host subcellular organelle in which the enzyme will have optimal activity, for example, by means of signal peptide not normally associated with the enzyme. It should be clear that the enzymes described herein and their activities are well-known in the art.

Particularly envisaged herein as "glyco-engineered cells" according to the invention are cells as described in WO2010015722 and WO2015032899 (further designated herein as GlycoDelete cells, or cells having a GlycoDelete background). In brief, such a cell is engineered to reduce glycosylation heterogeneity and at least comprises a nucleotide sequence encoding an endoglucosaminidase enzyme and an expression vector comprising a nucleotide sequence encoding a target polypeptide.

As heterogeneity in glycosylation does not only originate from N-linked sugars, but also from 0-glycans attached to the glycoprotein, it can be desirable to remove these diverse carbohydrate chains from the polypeptides of the invention. This can be achieved by expressing an endoglucosaminidase enzyme in a cell that is deficient in expression and/or activity of an endogenous UDP-Galactose 4-epimerase (GalE) as described in WO2017005925. Cells described in the latter application are also particularly envisaged as glyco-engineered cells according to the present invention and herein further described as GlycoDoubleDelete cells or cells having a GlycoDoubleDelete background.

Also particularly referred to herein as "glyco-engineered cells" are non-mammalian cells engineered to mimic the human N-glycosylation pathway (i.e. GlycoSwitch®, see also Laukens, B. et al (2015) *Methods Mol Biol.* 1321 and Jacobs, P. P. et al. (2009) *Nat Protoc.* 4(1)).

An "IVD conjugate" or an "ISVD conjugate" is referred to herein as a polypeptide comprising an IVD or ISVD of the invention which is coupled (or conjugated or connected, which are equivalent terms in the art) with a specific moiety, herein further defined as the "conjugated moiety". Coupling between the IVD conjugate or ISVD conjugate can occur via a specific amino acid (e.g. lysine, cysteine) present in the IVD or ISVD. Preferably coupling occurs via the introduced glycan (e.g. an introduced N-glycan) present in the polypeptide sequence of said IVD or ISVD. Glycan-specific conjugation can be performed with glycans present in an introduced glycan site of the IVD or ISVD. In specific cases glycans can be modified further in vitro (e.g. trimmed with specific exoglycosidase enzymes) before they are coupled to a "conjugated moiety". In addition, coupling can also occur as a combination between i) a specific amino acid present in said IVD or ISVD and ii) the coupling via the introduced glycan and a conjugated moiety. Conjugation may be performed by any method described in the art and some non-limiting illustrative embodiments will be outlined in the example section.

As used herein, the term "conjugated moiety" comprises agents (e.g. proteins (e.g. a second IVD or ISVD), nucleotide sequences, lipids, (other) carbohydrates, polymers, peptides, drug moieties (e.g. cytotoxic drugs), tracers and detection agents) with a particular biological or specific functional activity. For example, an IVD or ISVD conjugate comprising a polypeptide according to the invention and a conjugated moiety has at least one additional function or property as compared to the unconjugated IVD or ISVD polypeptide of the invention. For example, an IVD or ISVD conjugate comprising a polypeptide of the invention and a cytotoxic drug being the conjugated moiety results in the formation of a binding polypeptide with drug cytotoxicity as second function (i.e. in addition to antigen binding conferred by the IVD or ISVD polypeptide). In yet another example, the conjugation of a second binding polypeptide to the IVD or ISVD polypeptide of the invention may confer additional binding properties. In certain embodiments, where the conjugated moiety is a genetically encoded therapeutic or diagnostic protein or nucleotide sequence, the conjugated moiety may be synthesized or expressed by either peptide synthesis or recombinant DNA methods that are well known in the art. In another aspect, where the conjugated moiety is a non-genetically encoded peptide, e.g. a drug moiety, the conjugated moiety may be synthesized artificially or purified from a natural source.

The present invention aims to provide polypeptides comprising IVDs or ISVDs having glycosylation acceptor sites present in specific regions, in particular in regions allowing for efficient glycosylation and which glycosylation does not interfere with the binding and folding of the IVDs or ISVDs, that makes them more amenable for further use, e.g. production of IVD or ISVD conjugates.

The present invention provides a nucleotide sequence encoding a polypeptide which polypeptide comprises an antibody mimetic wherein said antibody mimetic has at least one artificially engineered N-glycosylation site introduced at any possible position and wherein the glycosylation of said glycosylation acceptor site consists of one or more glycans selected from the group consisting of GlcNAc, LacNAc and sialyl-LacNAc.

In yet another embodiment the invention provides a polypeptide which polypeptide comprises an antibody mimetic wherein said antibody mimetic has at least one artificially engineered N-glycosylation site introduced at any possible position and wherein the glycosylation of said glycosylation acceptor site consists of one or more glycans selected from the group consisting of GlcNAc, LacNAc and sialyl-LacNAc.

In yet another embodiment the invention provides a conjugate comprising a polypeptide which polypeptide comprises an antibody mimetic wherein said antibody mimetic has at least one artificially engineered N-glycosylation site introduced at any possible position and wherein the glycosylation of said glycosylation acceptor site consists of one or more glycans selected from the group consisting of GlcNAc, LacNAc and sialyl-LacNAc and a conjugated moiety coupled to said glycans.

The term "antibody mimetic" as used herein, refers to artificial (poly-)peptides that, like antibodies, can specifically bind antigens, but that are not structurally related to antibodies. They are usually significantly smaller than antibodies with a molar mass of about 3 to 20 kDa. Non-limiting examples of antibody mimetics are abdurins, adnectins, affibodies, affilins, affimers, alphabodies, affitins, anticalins, avimers, DARPins, fynomers, Kunits domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the 10$^{th}$ type III domain of fibronectin, 3- or 4-helix bundle proteins, an armadillo repeat domain, a leucine-rich repeat domain, a PDZ domain, a SUMO or SUMO-like domain, an immunoglobulin-like domain, phosphotyrosine-binding domain, pleckstrin homology domain, src homology 2 domain or synthetic peptide ligands, e.g., from a (random) peptide library. Other examples of antigen-binding proteins also include synthetic binding proteins, more specifically also monobodies (e.g. for a review see Sha et al., 2017. Protein Science. 26:910-924). Monobodies are synthetic proteins, constructed on the basis of the fibronectin type III domain. Monobodies that bind with high affinity to a diverse array of targets, including the extracellular domain of receptors, kinases, steroid hormone receptors and modular protein domains, have been isolated (Koide, 2012).

In yet another embodiment the invention provides an ISVD polypeptide which polypeptide has at least one artificially engineered N-glycosylation site introduced at any possible position in its polypeptide sequence and wherein the glycosylation of said glycosylation acceptor site consists of one or more glycans selected from the group consisting of GlcNAc, LacNAc and sialyl-LacNAc.

In yet another embodiment the invention provides a conjugate comprising an ISVD polypeptide which polypeptide has at least one artificially engineered N-glycosylation site introduced at any possible position in its sequence and wherein the glycosylation of said glycosylation acceptor site consists of one or more glycans selected from the group consisting of GlcNAc, LacNAc and sialyl-LacNAc and a conjugated moiety coupled to said glycans.

In yet another embodiment the invention provides a nucleotide sequence encoding a polypeptide comprising an IVD, wherein said IVD has a glycosylation acceptor site present at any of amino acids 83 to 88 and/or at any of amino acids 27 to 40 of the IVD (according to AHo numbering convention). For the sake of clarity an IVD having a glycosylation acceptor site present at any of amino acids 83 to 88 and/or at any of amino acids 27 to 40 of the IVD (according to AHo numbering convention) is herein further designated as "an IVD of the invention" or "an ISVD of the invention".

In yet another embodiment the invention provides a nucleotide sequence encoding a polypeptide comprising an IVD, wherein said IVD has a glycosylation acceptor site present at any of amino acids 83 to 88 of the IVD (according to AHo numbering convention).

In yet another embodiment the invention provides a nucleotide sequence encoding a polypeptide comprising an IVD, wherein said IVD has a glycosylation acceptor site present at any of amino acids 27 to 40 of the IVD (according to AHo numbering convention).

In yet another embodiment the invention provides a nucleotide sequence encoding a polypeptide comprising an IVD, wherein said IVD has a glycosylation acceptor site present at any of amino acids 83 to 88 and at any of amino acids 27 to 40 of the IVD (according to AHo numbering convention).

Said glycosylation acceptor site can be modified (but not necessarily) with an N- or an O-linked glycan. It is particularly envisaged herein that the invention is not limited to N-glycosylation. The present disclosure provides means to employ both N- and O-glycosylation.

In an embodiment according to the invention a nucleotide sequence is provided encoding a polypeptide comprising an IVD, wherein said IVD has a glycosylation acceptor site present at any of amino acids 84 to 88, 85 to 88, 86 to 88, 87 and 88, 83 to 87, 84 to 87, 85 to 87, 83, 84, 85, 86, 87, 88, 83 to 86, 84 to 86, 85 and 86, 83 to 85, 84 and 85 or 83 and 84 and/or at any of amino acids 28 to 40, 29 to 40, 30 to 40, 31 to 40, 32 to 40, 33 to 40, 34 to 40, 35 to 40, 36 to 40, 37 to 40, 38 to 40, 39 and 40, 27, 28, 29, 30, 31, 32, 33, 34, 35, 36, 37, 38, 39 and 40, 27 to 39, 28 to 39, 29 to 39, 30 to 39, 31 to 39, 32 to 39, 33 to 39, 34 to 39, 35 to 39, 36 to 39, 37 to 39, 38 and 39, 27 to 38, 28 to 38, 29 to 38, 30 to 38, 31 to 38, 32 to 38, 33 to 38, 34 to 38, 35 to 38, 36 to 38, 37 and 38, 27 to 37, 28 to 37, 29 to 37, 30 to 37, 31 to 37, 32 to 37, 33 to 37, 34 to 37, 35 to 37, 36 and 37, 27 to 36, 28 to 36, 29 to 36, 30 to 36, 31 to 36, 32 to 36, 33 to 36, 34 to 36, 35 to 36, 27 to 35, 28 to 35, 29 to 35, 30 to 35, 31 to 35, 32 to 35, 33 to 35, 34 and 35, 27 to 34, 28 to 34, 29 to 34, 30 to 34, 31 to 34, 32 to 34, 33 and 34, 27 to 33, 28 to 33, 29 to 33, 30 to 33, 31 to 33, 32 and 33, 27 to 32, 28 to 32, 29 to 32, 30 to 32, 31 and 32, 27 to 31, 28 to 31, 29 to 31, 30 and 31, 27 to 30, 28 to 30, 29 and 30, 27 to 29, 28 and 29 or 27 and 28 of the IVD (according to AHo numbering convention).

In yet another embodiment according to the invention a nucleotide sequence is provided encoding a polypeptide comprising an IVD, wherein said IVD has a glycosylation acceptor site present at amino acid 86 and/or at amino acid 27 of the IVD (according to AHo numbering convention).

In yet another embodiment according to the invention a nucleotide sequence is provided encoding a polypeptide comprising an IVD, wherein said IVD has a glycosylation acceptor site present at amino acid 86 and at amino acid 27 of the IVD (according to AHo numbering convention).

In yet another embodiment according to the invention a nucleotide sequence is provided encoding a polypeptide comprising an IVD, wherein said IVD has a glycosylation acceptor site present at amino acid 86 of the IVD (according to AHo numbering convention).

In yet another embodiment according to the invention a nucleotide sequence is provided encoding a polypeptide comprising an IVD, wherein said IVD has a glycosylation acceptor site present at amino acid 27 of the IVD (according to AHo numbering convention).

In a preferred embodiment a nucleotide sequence is provided encoding a polypeptide comprising an IVD, wherein said IVD has a glycosylation acceptor site present at any of amino acids 83 to 88 of the IVD (according to AHo numbering convention). More specifically, the glycosylation acceptor site of said IVD is present at amino acids 84 to 88, 83, 84, 85, 86, 87, 88, to 88, 86 to 88, 87 and 88, 83 to 87, 84 to 87, 85 to 87, 86 and 87, 83 to 86, 84 to 86, 85 and 86, 83 to 85, 84 and 85 or 83 and 84 (according to AHo numbering convention). Most specifically, the glycosylation acceptor site of said IVD is present at amino acid 86 of the IVD (according to AHo numbering convention).

In another embodiment according to the invention a nucleotide sequence encoding a polypeptide comprising an IVD is provided, wherein said IVD has a glycosylation acceptor site present at any of amino acids 27 to 40 of the IVD (according to AHo numbering convention). More specifically, the glycosylation acceptor site of said IVD is present at any of amino acids 27, 28, 29, 30, 31, 32, 33, 34, 35, 36, 37, 38, 39, 40, 28 to 40, 29 to 40, 30 to 40, 31 to 40, 32 to 40, 33 to 40, 34 to 40, 35 to 40, 36 to 40, 37 to 40, 38 to 40, 39 and 40, 27 to 39, 28 to 39, 29 to 39, 30 to 39, 31 to 39, 32 to 39, 33 to 39, 34 to 39, 35 to 39, 36 to 39, 37 to 39, 38 and 39, 27 to 38, 28 to 38, 29 to 38, 30 to 38, 31 to 38, 32 to 38, 33 to 38, 34 to 38, 35 to 38, 36 to 38, 37 and 38, 27 to 37, 28 to 37, 29 to 37, 30 to 37, 31 to 37, 32 to 37, 33 to 37, 34 to 37, 35 to 37, 36 and 37, 27 to 36, 28 to 36, 29 to 36, 30 to 36, 31 to 36, 32 to 36, 33 to 36, 34 to 36, 35 to 36, 27 to 35, 28 to 35, 29 to 35, 30 to 35, 31 to 35, 32 to 35, 33 to 35, 34 and 35, 27 to 34, 28 to 34, 29 to 34, 30 to 34, 31 to 34, 32 to 34, 33 and 34, 27 to 33, 28 to 33, 29 to 33, 30 to 33, 31 to 33, 32 and 33, 27 to 32, 28 to 32, 29 to 32, 30 to 32, 31 and 32, 27 to 31, 28 to 31, 29 to 31, 30 and 31, 27 to 30, 28 to 30, 29 and 30, 27 to 29, 28 and 29 or 27 and 28 of the IVD (according to AHo numbering convention).

Most specifically, the glycosylation acceptor site of said IVD is present at amino acid 27 of the IVD (according to AHo numbering convention).

It should be clear to the skilled person based on the disclosure presented herein that additional positions in the IVD next to positions 83 to 88 and/or 27 to 40 can be selected which are prone for glycosylation.

Therefore, in particular embodiments according to the invention, a nucleotide sequence is provided encoding a polypeptide comprising an IVD, wherein said IVD has a glycosylation acceptor site present at any of amino acids 83 to 88 and/or at any of amino acids 27 to 40 of the IVD and has an additional glycosylation acceptor site in the IVD, present at a position such as position 14 and/or position 48 (according to AHo numbering convention). According to particular embodiments, the IVD of the invention has an additional glycosylation acceptor site introduced in the IVD at every possible position in said IVD. According to other particular embodiments, the IVD of the invention has an additional glycosylation acceptor site in the IVD present at position 14 (according to AHo numbering convention). According to other particular embodiments, the IVD of the invention has an additional glycosylation acceptor site in the IVD present at position 48 (according to AHo numbering convention).

In yet another embodiment the IVD of the invention has, according to particular embodiments, an additional glycosylation acceptor site present at position 16 and/or 49 and/or 139.

In yet another embodiment the IVD of the invention has an extra terminal amino (N-)-terminal tag and/or an extra carboxy terminal (C-) which tag includes a glycosylation acceptor site, particularly an N-glycan acceptor site.

Thus it is clear that the scope of the present invention includes the simultaneous use of at least two or even more glycosylation acceptor sites within the IVD of the present invention. Based on the present application, the skilled person knows how to select additional glycosylation acceptor sites within or next to the specific glycosylation acceptor sites identified in the IVDs of the invention and identification/or use of further positions and their combination is also within the scope of the invention as presented.

In a specific embodiment the invention provides the polypeptides encoded by the IVD nucleotide sequences described herein before.

According to another embodiment, the glycosylation acceptor site of said IVD is an asparagine residue that can be N-glycosylated. More particularly, said IVD contains an NXT, NXS, NXC or NXV motif (in which X can be any amino acid except proline) such that the asparagine residue of the NXT/NXS/NXC/NXV motif is present at any of amino acids 83 to 88 and/or at any of amino acids 27 to 40. Even more particularly, said IVD contains an NXT/NXS motif.

According to a particular embodiment, the invention provides a nucleotide sequence encoding a polypeptide comprising an IVD as described before, wherein said IVD is an immunoglobulin single variable domain (ISVD)

According to a particular embodiment, a nucleotide sequence encoding a polypeptide comprising an ISVD as described before is provided, wherein said ISVD is a heavy chain variable domain sequence. According to a more particular embodiment, the ISVD is a heavy chain variable domain sequence that is derived from a heavy chain antibody, preferably a camelid heavy chain antibody.

In another particular embodiment, a nucleotide sequence encoding a polypeptide comprising an ISVD as described before is provided, wherein said polypeptide consists of said ISVD.

In yet another embodiment an expression vector is provided comprising a nucleotide sequence encoding a polypeptide comprising an IVD as described before.

In the present invention the term 'comprising a polypeptide comprising an ISVD' means that an ISVD can be fused (or coupled) to another polypeptide such as a half-life extending polypeptide (e.g. a VHH directed to serum albumin), a second VHH (such as to create a bispecific or bivalent IgG), an enzyme, a therapeutic protein, an Fc domain such as an IgA Fc domain or an IgG Fc domain.

In yet another embodiment the invention provides a cell comprising an expression vector according to the invention. In particular embodiments, the cell is a higher eukaryotic cell, such as a mammalian cell or a plant cell, a lower eukaryotic cell, such as a filamentous fungus cell or a yeast cell, or a prokaryotic cell.

Higher eukaryotic cells can be of any higher eukaryotic organism, but in particular embodiments mammalian cells are envisaged. The nature of the cells used will typically depend on the desired glycosylation properties and/or the ease and cost of producing the IVD or ISVD described herein. Mammalian cells may for instance be used to avoid problems with immunogenicity. Higher eukaryotic cell lines for protein production are well known in the art, including cell lines with modified glycosylation pathways. Non-limiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, Som. Cell Molec. Genet., 12:555-556; and Kolkekar et al., 1997, Biochemistry, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, Proc. Natl. Acad. Sci. USA, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, J. Gen. Virol., 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251);

human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, Annals NY Acad. Sci., 383:44-68); MCR 5 cells; FS4 cells. According to particular embodiments, the cells are mammalian cells selected from CHO cells, Hek293 cells or COS cells. According to further particular embodiments, the mammalian cells are selected from CHO cells and Hek293 cells.

According to other particular embodiments, the cell according to the invention is a plant cell. Typical plant cells comprise cells from tobacco, tomato, carrot, maize, algae, alfalfa, rice, soybean, *Arabidopsis thaliana, Taxus cuspidata, Nicotiana benthamiana*, and *Catharanthus roseus*. Still aditional plant species which can be useful for the production of IVD or ISVD polypeptides according to the invention are described in Weathers, P. J. et al., *Appl Microbiol Biotechnol.* 85(5), 2010.

In more particular embodiments, the cell according to the invention is a lower eukaryotic cell, such as a filamentous fungus cell or a yeast cell. Specific examples of filamentous fungi and yeast cells have been outlined herein before.

In more particular embodiments, the cell according to the invention is a prokaryotic ell, such as *E. coli, Lactococcus* species or *Bacillus* species.

In more particular embodiments, the cell according to the invention as described before is a glyco-engineered cell. A glyco-engineered cell can be capable of removing unwanted N-glycosylation and/or O-glycosylation. The term glyco-engineered cell has been outlined herein before. A glyco-engineered cell can also be a non-mammalian cell engineered to mimic the human glycosylation pathway as described before.

In a particular embodiment, a polypeptide comprising an IVD encoded by a nucleotide sequence according to the invention as described before is provided, wherein the polypeptide comprises a glycan (or more than one glycan) wherein the glycan has a terminal GlcNAc, GalNAc, galactose, sialic acid, glucose, glucosamine, galactosamine, bacillosamine (a rare amino sugar (2,4-diacetamido-2,4,6-trideoxyglucose) described for example in *Bacillus subtilus* and *Campylobacter jejuni*), Mannose or Mannose-6-P sugar or a chemically modified monosaccharide such as GalNAz, Azido-sialic acid (AzSia), or GlcNAz. IVD polypeptides comprising a glycan with the specific sugars can be made in vivo. For example higher eukaryotic cells will typically generate glycans with terminal sialic acid, yeast cells will typically generate glycans with terminal mannose or mannose-6P, certain filamentous fungus will generate glycans with a terminal galactose, certain glycoengineered yeast cells produce terminal GlcNAc (e.g. described in WO2010015722), certain glycoengineered higher eukaryotic cells produce mixtures of glycans with terminal GlcNAc, galactose and sialic acid (e.g. described in WO2010015722 and WO2015032899), other glycoengineered higher eukaryotic cells produce glycans with terminal GlcNAc (see WO2017005925), eukaryotic cells comprising certain mutant galactosyltransferases can enzymatically attach GalNAc to a non-reducing GlcNAc sugar (see WO2004063344), eukaryotic cells comprising mutant galactosyltransferase which are fed with UDP-GalNAz (a C2-substituted azidoacetamido-galactose UDP-derivative) will incorporate GalNAz at a terminal non-reducing GlcNAc of a glycan (see WO2007095506 and WO2008029281). Optionally IVD polypeptides comprising a glycan with the specific sugars can be made by a combination of in vivo followed by in vitro trimming of the glycan until the desired terminal sugar is obtained, e.g. WO2015057065 (Synaffix).

In yet another particular embodiment the invention provides a polypeptide comprising an IVD of the present invention wherein the IVD comprises a glycan (or more than one glycan) and wherein the glycan consists of a glycan selected from the group consisting of GlcNAc, LacNAc, sialyl-LacNAc, Man5GlcNAc2, Man8GlcNAc2, Man9GlcNAc2, hyper-mannosylated glycans, mannose-6-phosphate glycans, complex glycans, hybrid glycans and chemically modified glycans such as GlcNAz, GlcNAc-GalNAz, azido-sialic acid-LacNAc.

In yet another particular embodiment the invention provides a composition comprising a polypeptide comprising an IVD of the present invention wherein the IVD comprises a glycan (or more than one glycan) and wherein the glycan consists of a glycan selected from the group consisting of GlcNAc, LacNAc, sialyl-LacNAc, Man5GlcNAc2, Man8GlcNAc2, Man9GlcNAc2, hypermannosyl glycans, mannose-6-phosphate glycans, complex glycans, hybrid glycans and chemically modified glycans such as GlcNAz, GlcNAc-GalNAz, azido-sialic acid-LacNAc, wherein the presence of one or more of these glycans at a particular position or positions in said polypeptide is at least 20%, at least 30%, at least 40%, at least 50%, at least 60%, at least 70%, at least 80% or at least 90% with respect to the same polypeptide in the sample.

While the variety of host cells described herein before can be particularly useful to produce specific glycans present on the IVDs provided by the invention, it should be kept in mind that also combined in vivo and in vitro approaches are possible to obtain the desired glycan structure. Indeed, IVDs or ISVDs of the invention which have been produced in eukaryotic hosts can be purified, the glycan structures can be trimmed by suitable endoglucosaminidases or exoglycosidases and thereafter can be re-built by the in vitro use of a variety of glycosyltransferases (e.g. galactosyltransferases, sialyltransferases, polysialyltransferases and the like).

IVD-Conjugates

In a particular embodiment the invention provides IVD-conjugates. In a preferred embodiment the IVD or ISVD polypeptides according to the invention are coupled to a specific moiety (a conjugated moiety as defined herein before) via the glycan structures present on said IVD or ISVD polypeptides. Such glycan specific coupling to a specific moiety is referred to in the art as glycan-specific conjugation. Glycan structures with specific terminal carbohydrates or specific glycan structures as herein described before present on the IVD or ISVD polypeptides are used as a starting point for the coupling with a specific moiety.

Specific Moieties which can be Used for Conjugation

A plethora of conjugated moieties exist in the art which can be used for coupling to the glycan structure present in the IVD or ISVD of the invention. Conjugated moieties comprise for example a half-life extending moiety, a therapeutic agent, a detection unit, a targeting moiety or even a second (the same or different) IVD or ISVD polypeptide. One or more conjugated moieties, which can also be different from each other, can be linked to the IVD or ISVD of the invention. Even one conjugated moiety can have more than one function, i.e. a half-life extending moiety can at the same time be useful as a targeting moiety.

i) Half-Life Extending Moieties

Various half-life extending moieties are envisaged herein. Non-limiting and in brief, reference is made to the half-life extension strategies described in Kontermann, R. E., Expert Opin Biol Ther. 16(7), 2016 or van Witteloostuijn, S. B., Chem Med Chem. 11(22), 2016. In particular, a variety of half-life extension techniques relying on covalent chemical modification have been developed. These methods include PEGylation, fusion to unstructured polypeptide-based PEG mimetics, employment of polysialylation (e.g. enzymatic use of polysialyltransferase enzymes), biotin-coupling, polyoxazoline-coupling, conjugation with large polysaccharides, lipidation, fusion to albumin or the Fc domain of IgG or the Fc domain of IgA, and derivatization with bioorthogonal moieties that direct self-assembly. Yet another half-life extending moiety is an IVD (such as a VHH) directed to serum albumin.

ii) Therapeutic Moieties

In certain embodiments the conjugated moiety comprises various therapeutic agents including i.e. anti-inflammatory, anticancer, cytotoxic, anti-infective (e.g., anti-fungal, antibacterial, anti-parasitic, anti-viral, etc.), and anesthetic therapeutic agents. In specific embodiments the conjugated moiety is an enzyme capable of converting a prodrug which is converted into a toxic drug. A toxic agent (e.g. a toxin, a cytotoxic drug, a radionuclide) can also be suitable for therapeutic purposes and is particularly useful in cancer therapy. Hence, a specific example of an IVD-conjugate is an antibody-drug-conjugate (ADC). In principal, every agent suitable for therapeutic purposes is envisaged herein. Therapeutic agents as described are typically small molecules or biologics, but therapeutic agents can also be of another origin what should be clear to the skilled person and the invention should not be limited thereto.

iii) Detection Moieties

In certain embodiments the conjugated moiety comprises a detection moiety. The term "detection moiety" or "detectable label" refers to any unit possessing a property or function which can be used for detection purposes, i.e. those selected from the group comprising a chromophore unit, fluorescent unit, phosphorescent unit, luminescent unit, light absorbing unit, radioactive unit, and transition metal isotope mass tag unit. Without being limiting, the detection moiety can be a small or a large molecule as should be clear to the skilled person.

Suitable fluorescent units are those known from the art of immunofluorescence technologies, e.g., flow cytometry or fluorescence microscopy. In these embodiments of the invention, the conjugate comprising the detection unit is detected by exciting the detection unit and detecting the resulting emission (photoluminescence). In this embodiment, the detection unit is preferably a fluorescent unit.

Useful fluorescent units might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent units.

Another group of photoluminescent detection units are phosphorescent units with time-delayed emission of light after excitation. Phosphorescent units include metallo-organic complexes, such as Pd, Pt, Tb, Eu complexes, or nanoparticles with incorporated phosphorescent pigments such as lanthanide doped SrA1204.

In another embodiment of the invention the conjugate comprising the detection unit is detected without prior excitation by irradiation. In this embodiment the detection unit can be a radioactive label. They may be in the form of radioisotope labelling by exchanging non-radioactive isotopes for their radioactive counterparts, such as tritium, $^{32}$P, $^{35}$S or $^{14}$C, or introducing covalently bound labels, such as $^{125}$I, which is bound to tyrosine, $^{18}$F within fluorodeoxyglucose, or metallo-organic complexes, i.e. $^{99}$Tc-DTPA.

In another embodiment the detection unit is capable of causing chemiluminescence, i.e. horseradish peroxidase label in the presence of luminol.

In another embodiment of the invention the conjugate comprising the detection unit is not detected by radiation emission, but by absorption of UV, visible light, or NIR radiation. Suitable light-absorbing detection moieties are light absorbing dyes without fluorescence emission, such as small organic molecule quencher dyes like N-aryl rhodamines, azo dyes, and stilbenes.

In another embodiment, the light-absorbing detection unit can be irradiated by pulsed laser light, generating a photoacoustic signal.

In another embodiment of the invention the conjugate comprising the detection unit is detected by mass spectrometric detection of a transition metal isotope. Transition metal isotope mass tag labels might be introduced as covalently bound metallo-organic complexes or nanoparticle component. Known in the art are isotope tags of lanthanides and adjacent late transition elements.

iv) Targeting Moiety

In certain embodiments, the conjugated moiety comprises a targeting moiety. As used herein, the term "targeting moiety" refers to a conjugated moiety that binds to a target molecule. Small molecules or biologics can both be employed as a targeting moiety. Targeting moieties can comprise, without limitation, proteins, nucleotide sequences, lipids, other carbohydrates (e.g. specific glycans), and combinations thereof (e.g., glycoproteins, glycopeptides, and glycolipids). Any moiety which is able to bind to a target can be employed as a targeting moiety according to the invention.

Linkers Useful in the IVD-Conjugates

In certain embodiments the IVD-conjugates comprise a linker between the glycan and the targeting moiety. Certain linkers are more useful than others and the use of a specific linker will depend on the application. For example oximes and hydrazones, in particular derived from aliphatic aldehydes, show less stability over time in water or at lower pH. Aromatically stabilized structures can be more useful to stably link a glycan to a conjugated moiety. Such stabilized linkers are also within the scope of the present application, as they can limit adverse effects due to premature release of the conjugated moiety, particularly when the conjugated moiety is a toxic substance intended for killing of a tumor cell. Of particular interest are BICYCLO[6.1.0]NON-4-YNE REAGENTS as well as aromatically stabilized triazole linkers and sulfamide linkers. It is within common technical knowledge that increased stability of a conjugate can also result from reduced aggregation tendency of any of the moieties comprised within said conjugate. For the production of IVD conjugates with increased stability the reader is non-exclusively referred to WO2013036748, WO2014065661, WO2015057064 and WO2016053107 as well as to other patent applications filed by Synaffix B.V. Explicitly mentioned herein.

In general various linkers known in the art can be used to link the IVD and the conjugated moiety according to the invention. As should be clear, cleavable and non-cleavable linkers can be employed to achieve the desired release profile. In general, the optimal combination of linker and conjugation chemistry must be uniquely tailored to correlate each unique facet: the IVD, the conjugated moiety, and the profile of the disease to be treated. For reviews on antibody-drug conjugates and linkers used herein see for example Jessica R. McCombs and Shawn C. Owen, AAPS J. 17(2), 2015 and Lu, J. et al., Int J Mol Sci. 17(4), 2016 as well as a recent review by Pillow, T. H., Pharm Pat Anal. 6(1), 2017 describing a novel quaternary ammonium salt linker useful in conjugates for the treatment of cancer and infectious diseases.

Still other suitable spacers or linkers will be clear to the skilled person, and may generally be any linker or spacer used in the art. In specific aspects the linkers or spacers are suitable for use in applications which are intended for pharmaceutical use. For example, a linker between the glycan and the moiety in the ISVD-conjugate or IVD-conjugate may in certain aspects also be a suitable amino acid sequence, and in particular amino acid sequences of between 1 and 50, or more specifically, between 1 and 30 amino acid residues. Some examples of such amino acid sequences include Gly-Ser (GS) linkers, such as for example (GS)n or (GGGSS)n or (GSS)n, as described in WO 99/42077 and the $(G4S)_3$, $GS_{30}$, $GS_{15}$, $GS_9$ and $GS_7$ linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Still other suitable linkers generally comprise organic compounds or polymers, in particular those suitable for use in polypeptides for pharmaceutical use. For instance, poly(ethyleneglycol) moieties have been used to link antibody domains, see for example WO 04/081026. It is encompassed within the scope of the invention that the length, the degree of flexibility and/or other properties of the linker may have some influence on the properties of the final IVD conjugate of the invention, including but not limited to the affinity, specificity or avidity for a specific target. Based on the disclosure herein, the skilled person will be able to determine the optimal linker for use in a specific IVD or ISVD of the invention, optionally after some limited routine experiments. For example, in multivalent ISVDs of the invention that comprise building blocks, directed against a first and second target, the length and flexibility of the linker is preferably such that it allows each building block to bind to its cognate target. Again, based on the disclosure herein, the skilled person will be able to determine the optimal linker for use in a specific IVD or ISVD of the invention, optionally after some limited routine experiments. Finally, when two or more linkers are used in the IVD or ISVD of the invention, these linkers may be the same or different. Again, based on the disclosure herein, the skilled person will be able to determine the optimal linkers for use in a specific polypeptide of the invention, optionally after some limited routine experiments. In certain specific embodiments it is desirable to produce IVD conjugates with longer linkers including for example carbohydrates, which can provide the IVD conjugate with higher hydrophilicity and accordingly improved water-solubility. IVD conjugates comprising linkers with more carbohydrates are thus also within the scope of the present application. Also linkers modified with PEG or consisting of PEG can be useful to increase the hydrophilic properties of an IVD conjugate.

In yet another embodiment the invention provides a method to produce a polypeptide comprising an IVD of the invention, said method comprises the steps of introducing an expression vector comprising a nucleotide sequence encoding an IVD of the invention in a suitable expression host, expressing and isolating said IVD of the invention. Suitable conditions have to be chosen to express the polypeptide comprising an IVD according to the invention.

By the term "a suitable cell" a higher eukaryotic cell, such as a mammalian cell or a plant cell, a lower eukaryotic cell, such as a filamentous fungus cell or a yeast cell which is optionally glyco-engineered, is envisaged as explained above.

Particularly envisaged herein is the production of polypeptides comprising an IVD or IVSD according to the invention, wherein said polypeptide is glycosylated and comprises one or more glycans with a terminal GlcNAc, GalNAc, Galactose, Sialic Acid, Glucose, Glucosamine, Galactosamine, Bacillosamine, Mannose or Mannose-6-P sugar or a chemically modified monosaccharide such as GalNAz, AzSia, or GlcNAz.

For example a polypeptide comprising an IVD of the invention, wherein the polypeptide is N-glycosylated and comprises a mixture of N-glycans with a terminal GlcNAc, Galactose or Sialic Acid can typically be obtained by expression in a higher eukaryotic glyco-engineered cell according to the invention as described in WO2010015722 and WO2015032899. For example a polypeptide comprising an IVD of the invention, wherein the polypeptide is N-glycosylated and comprises or essentially comprises an N-glycan with a terminal GlcNAc can be produced in a lower eukaryotic cell as described in WO2010015722. For example an N-glycan with a terminal GlcNAc can be produced in a glyco-engineered cell deficient in expression and/or activity of an endogenous UDP-Galactose 4-epimerase (GalE) as described in WO2017005925.

Also particularly envisaged herein is the production of polypeptides comprising an IVD according to the invention, wherein the glycosylation of said polypeptide consists of one or more glycans selected from the group consisting of GlcNAc, LacNAc, sialyl-LacNAc, Man5GlcNAc2, Man8GlcNAc2, Man9GlcNAc2, complex glycans, hybrid glycans and GlcNAc-GalNAz. Even more particularly envisaged herein is the production of polypeptides comprising an IVD according to the invention, wherein the glycosylation of said polypeptide consists of one or more glycans selected from the group consisting of GlcNAc, LacNAc, sialyl-LacNAc, Man5GlcNAc2, Man8GlcNAc2, Man9GlcNAc2 and complex glycans.

A polypeptide comprising an IVD of the invention, wherein the polypeptide is glycosylated and wherein the glycosylation consists of GlcNAc, LacNAc and sialyl-LacNAc glycans is typically obtained in a glyco-engineered mammalian cell according to the invention as described in WO2010015722 and WO2015032899, although such GlcNAc, LacNAc and sialyl-LacNAc glycans could also be engineered in lower eukaryotic cells (e.g. via the introduction of the mammalian complex glycosylation pathway in yeast). A polypeptide comprising an IVD of the invention, wherein the polypeptide is glycosylated and wherein the glycosylation consists of a GlcNAc can be produced in a glyco-engineered cell according to the invention, which can be deficient in expression and/or activity of an endogenous UDP-Galactose 4-epimerase (GalE) as described in WO2017005925. A polypeptide comprising an IVD of the invention, wherein the polypeptide is glycosylated and wherein the glycosylation consists of a complex glycan can be produced in a higher eukaryotic cell according to the invention, which is optionally glyco-engineered. A polypeptide comprising an IVD of the invention, wherein the polypeptide is glycosylated and wherein the glycosylation consists of one or more glycans selected from the group consisting of Man5GlcNAc2 glycans, Man8GlcNAc2 glycans, Man9GlcNAc2 glycans, hypermannosylated glycans, mannose-6-phosphate modified glycans and complex glycans can be produced in glyco-engineered cells according to the invention, particularly in yeast cells.

Coupling Methods to Link Specific Moieties to an IVD

In yet another embodiment the invention provides methods to produce an IVD or ISVD conjugate of the invention. Generally, such methods start by introducing an expression vector comprising a nucleotide sequence encoding an IVD according to the invention in a suitable cell of choice, followed by expressing the IVD polypeptide for some time, purifying the IVD polypeptide and linking of a specific conjugated moiety to the purified IVD polypeptide. The coupling method itself is generally carried out in vitro.

Several possibilities exist in the art to link a specific conjugated moiety an IVD polypeptide of the invention. Generally spoken there are chemical, enzymatic and combined chemo-enzymatic conjugation strategies to carry out the coupling reaction.

According to a particular embodiment, said method to produce an IVD-conjugate comprises the steps of
  oxidizing the vicinal diol or dials present in glycans of a polypeptide comprising an IVD of the invention
  reacting the obtained free aldehyde groups with aminooxy-containing molecules.

For oxidation, sodium periodate or several other comparable reagents known in the art can be used. In a specific embodiment the diol to be oxidized originates from a LacNAc disaccharide or sialyl-LacNAc trisaccharide present on the IVD of the invention. Oximes are formed by subsequent reaction of the resulting free aldehyde groups with aminooxy-containing molecules, commonly described as LacNAc/sialyl-LacNAc oxidation-oxime ligation chemistry. Well-known in the art is the use of catalysts like para-phenylenediamine, 2-aminophenols or 2-(aminomethyl)benzimidazoles. Oxime and hydrazine conjugation are a promising alternative to click-chemistry, a more complex biorthogonal modification strategy. Under reductive amination conditions, the aldehyde (e.g. galactose oxidation generates a di-aldehyde, sialic acid oxidation generates a monoaldehyde) can be reacted with amines, which results in stable oxazepine derivatives.

According to another particular embodiment, said method to produce an IVD-conjugate optionally comprises the steps of
  oxidizing the C6 hydroxyl group of a Gal residue in the terminal LacNAc N-glycan present on an IVD of the invention
  reacting the free aldehyde group with aminooxy-containing molecules.

For oxidation, the enzyme Galactose Oxidase (GAO) can be used. Employing the above mentioned steps typically oxime bonds are formed, optionally in the presence of a catalase, all of this is well-known in the art.

To modulate or to particularly increase stability of oximes and hydrazones, the use of linkers as described before is particularly envisaged herein.

In more particular embodiments, the conjugated moiety is linked to the glycan present on the IVD, particularly a single GlcNAc or LacNAc, via a monosaccharide derivative. The monosaccharide derivative can be linked to the glycan present on the IVD in the presence of a glycosyltransferase, such as a $\beta(1,4)$-galactosyltransferase, a $\beta(1,3)$-galactosyltransferase, a $\beta(1,4)$-galactosyltransferase comprising a mutant catalytic domain, a $\beta(1,3)$-galactosyltransferase comprising a mutant catalytic domain, a sialyltransferase, or a GalNAc transferase. The monosaccharide can comprise 1, 2, 3 or 4 functional groups which can be selected from azido, keto, alkynyl or thiol groups or precursors thereof. The functional groups can also be selected from halogens, sulfonyloxy, halogenated acetamido, mercaptoacetamido or sulfonylated hydroxyacetamido groups. For a detailed protocol the reader is referred to WO2015057064 and WO2015057065.

In still other particular embodiments, the conjugated moiety is linked to the glycan via oxime-bonds and/or via conjugation of an azide-modified form of UDP-GalNAc to an N-glycan with terminal GlcNAc. In even more particular embodiments, the conjugated moiety is linked to the glycan via conjugation of an azide-modified form of UDP-GalNAc to an N-glycan with terminal GlcNAc using a modified galactosyltransferase followed by attachment of the molecule of interest via click-chemistry based reactions. Click-chemistry based reactions are well-known to those active in this field and also become clear based on the examples provided herein. For review articles on current approaches in click-chemistry, the reader is referred to Jain, N. et al. *Pharm Res.* 32(11), 2015, Qasba, P. K. et al., *Biotechnol Prog.* 24(3), 2008 or Nwe, K. and Brechbiel, M. W., *Cancer Biother Radiopharm.* 24(3), 2009.

The use of linkers to modulate the stability of the IVD conjugates as described before is particularly envisaged herein.

Several specific methods are specified in detail in the examples section further below.

Applications of IVDs and IVD-Conjugates of the Invention

In a particular embodiment, a polypeptide comprising an IVD-conjugate of the invention is used to modulate the circulation haft-life or to increase the IVD stability, for selective targeting, to modulate immunogenicity of the IVD-conjugate or for detection purposes.

In yet another embodiment the IVD-conjugates of the invention are used as a medicament.

In yet another embodiment the IVD (not conjugated with any moiety) of the invention is used as a medicament.

In yet another embodiment the IVD (not conjugated with any moiety) of the invention is used to prevent pre-antibody binding.

In yet another embodiment the IVD (not conjugated with any moiety) of the invention is used to reduce immunogenicity.

With the wording "to modulate circulation half-life" it is meant that the half-life of the polypeptide (e.g. IVD-conjugate) can be either increased or decreased. For some applications, it can be useful that the polypeptide comprising an IVD of the invention or IVD-conjugate of the invention remains in the bloodstream for a shorter time than polypeptides or conjugates lacking the specific properties of polypeptides or IVD-conjugates as claimed. Often, prolonged half-life is aimed as many therapeutic molecules are smaller than the renal filtration threshold and are rapidly lost from the circulation thereby limiting their therapeutic potential. As a non-limiting example, albumin or other half-life extending moieties as referred to above can be used in a variety of ways known to the skilled practitioner to increase the circulatory half-life of such molecules.

With "selective targeting" it is meant that polypeptides and IVD-conjugates of the invention can be useful to achieve an exclusive effect on the target of interest. An example of this is conventional chemotherapy where selective targeting of cancer cells without interacting with the normal body cells often fails. As a consequence thereof serious side effects are caused including organ damage resulting in impaired treatment with lower dose and ultimately low survival rates. Polypeptides and IVD-conjugates of the invention, optionally comprising a targeting moiety, can be useful to overcome the disadvantages of conventional approaches not limited to cancer therapy.

Using polypeptides and conjugates of the invention to modulate the immunogenicity can be achieved when compared to polypeptides or IVD-conjugates lacking the specific properties of polypeptides or IVD-conjugates as claimed. For example, for long-term treatment preference is given to low immunogenicity. Particularly and non-limiting, the glycans as described herein can be utilized as a tool to modify immunogenicity. The skilled person can adapt immunogenicity based on common knowledge and the disclosure provided herein.

The polypeptides and conjugates as described herein can be used to prevent or reduce binding to pre-existing antibodies. This effect has been described in literature for glycans on an ISVD (see i.e. WO2016150845). Use of polypeptides and conjugates according to the invention to prevent pre-antibody binding is within the scope of the present disclosure and also envisaged herein.

Polypeptides and conjugates of the invention are also provided for detection purposes, particularly when comprising a detection unit as explained before. Particularly, polypeptides and conjugates of the invention are more prone for detection purposes than polypeptides or conjugates lacking the specific properties of the claimed polypeptides or conjugates.

Thus in a particular embodiment the IVD-conjugates of the invention can also be used for diagnostic purposes.

In yet another embodiment the invention provides kits comprising IVDs of the present invention.

In yet another embodiment the invention provides kits comprising IVD-conjugates of the present invention.

In another embodiment, a pharmaceutical composition is provided comprising a polypeptide comprising an IVD or an IVD-conjugate as described before.

Therefore, the present invention includes pharmaceutical compositions that are comprised of a pharmaceutically acceptable carrier and a pharmaceutically effective amount of polypeptides, nucleotide sequences and IVD-conjugates of the invention and a pharmaceutically acceptable carrier. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of polypeptides, nucleotide sequences and conjugates of the invention and a pharmaceutically acceptable carrier is preferably that amount which produces a result or exerts an influence on the particular condition being treated. The polypeptides, nucleotide sequences and conjugates of the invention and a pharmaceutically acceptable carrier can be administered with pharmaceutically acceptable carriers well known in the art using any effective conventional dosage form, including immediate, slow and timed release preparations, and can be administered by any suitable route such as any of those commonly known to those of ordinary skill in the art. For therapy, the pharmaceutical composition of the invention can be administered to any patient in accordance with standard techniques. The administration can be by any appropriate mode, including orally, parenterally, topically, nasally, ophthalmically, intrathecally, intracerebroventricularly, sublingually, rectally, vaginally, and the like. Still other techniques of formulation as nanotechnology and aerosol and inhalant are also within the scope of this invention. The dosage and frequency of administration will depend on the age, sex and condition of the patient, concurrent administration of other drugs, counter-indications and other parameters to be taken into account by the clinician.

The pharmaceutical composition of this invention can be lyophilized for storage and reconstituted in a suitable carrier prior to use.

When prepared as lyophilization or liquid, physiologically acceptable carrier, excipient, stabilizer need to be added into the pharmaceutical composition of the invention (Remington's Pharmaceutical Sciences 22th edition, Ed. Allen, Loyd V, Jr. (2012). The dosage and concentration of the carrier, excipient and stabilizer should be safe to the subject (human, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as as TWEEN™, PLURONICS™ or PEG and the like.

The preparation containing pharmaceutical composition of this invention should be sterilized before injection. This procedure can be done using sterile filtration membranes before or after lyophilization and reconstitution.

The pharmaceutical composition is usually filled in a container with sterile access port, such as an i.v. solution bottle with a cork. The cork can be penetrated by hypodermic needle.

It is to be understood that although particular embodiments, specific configurations as well as materials and/or molecules, have been discussed herein for nucleotide sequences, cells, polypeptides, conjugates and methods according to the present invention, various changes or modifications in form and detail may be made without departing from the scope and spirit of this invention. The following examples are provided to better illustrate particular embodiments, and they should not be considered limiting the application. The application is limited only by the claims.

Example 1: Use of Crystallographic Data of ISVD Structures as a Rational Design Approach to Introduce N-Glycans In the present example we started from the available crystallographic structure of a representative immunoglobulin single variable domain polypeptide (chain B from entry 3K74 isolated from the RCSB Protein Data Bank, or in short: the PDB database; 3K74 contains two chains, id est the A chain (dihydrofolate reductase) and the B chain (the nanobody binding the dihydrofolate reductase); herein further we use 3K74 to specify the nanobody (B-chain) only) to identify regions in the structure suitable for the introduction of artificial N-glycosylation sites. This 3K74 ISVD polypeptide is a nanobody first described by Oyen D. et al (2011) *J. Mol. Biol.* 407: 138-148, and its secondary protein structure is schematically depicted in FIG. 1.

In our rational design approach, we reasoned that potential regions in the secondary structure for the introduction of an N-glycan should not interfere with (or should not disrupt) the antigen recognition site of the antibody and, importantly, should not hamper the formation of beta sheets during the folding. As the CDR regions of a nanobody are important for antigen recognition and the beta-sheet structure is important for the correct folding, we hypothesized that protein regions between the CDR regions and beta strands would probably be less sensitive to minor modifications such as the attachment of N-glycans.

Example 2: Selection of 9 Hypothetical Regions in the ISVD for the Introduction of N-Glycosylation Signatures Based on our rational design approach and specific criteria outlined in Example 1, we selected a total of 9 regions present in the representative nanobody 3K74 (see FIG. 1, right panel, the 9 selected regions for the introduction of artificial N-glycan acceptor sites are depicted in black). In addition to the regions present in the beta-sheet structural elements, we projected the addition of an N- and a C-terminal glycosylation tag to the actual nanobody amino acid sequence depicted in SEQ ID NO: 1.

The amino acid sequence of nanobody 3K74, without any N- and C-terminal tags is depicted in SEQ ID NO: 1. In SEQ ID NO: 1 the CDR1, CDR2 and CDR3 regions are underlined.

SEQ ID NO: 2 depicts CDR1, SEQ ID NO: 3 depicts CDR2, SEQ ID NO: 4 depicts CDR3, SEQ ID NO: 5 depicts FR1, SEQ ID NO: 6 depicts FR2, SEQ ID NO: 7 depicts FR3 and SEQ ID NO: 8 depicts FR4.

```
(115 amino acids)
SEQ ID NO 1:
QLQESGGGLVQPGGSLRLSCAASGFTFNNYWMYWVRRAPGKGLEWVSM

INPGGIITKYAESVKGRFTISRDNAKNTLYLQMNSLTSEDTAVYYCAK

DWATGLAKKGQGTQVTVSS
```

(CDR1): SEQ ID NO 2

GFTFNNYW (CDR2): SEQ ID NO 3

INPGGIITK (CDR3): SEQ ID NO 4

AKDWATGLA (FR1): SEQ ID NO 5

QLQESGGGLVQPGGSLRLSCAAS (FR2): SEQ ID NO 6

MYWVRRAPGKGLEWVSM (FR3): SEQ ID NO 7

YAESVKGRFTISRDNAKNTLYLQMNSLTSEDTAVYYC (FR4): SEQ ID NO 8

KKGQGTQVTVSS

Again based on the criteria outlined in example 1, we selected specific amino acid sequences within the 9 selected protein regions of nanobody 3K74 (see FIG. 2, which depicts the proposed 10 N-glycan acceptor sites to be introduced in the 9 different regions of the nanobody structure).

Example 3: Proof-of-Concept Using a GFP-Binding Nanobody

A GFP-binding nanobody (abbreviated as GBP and published by Kubala, M. H. et al (2010) Protein Sci. 19(12)) was selected as the benchmark ISVD for the introduction of the 10 rationally designed and proposed N-glycosylation acceptor sites specified in Example 2. We included an artificial N-terminal glyco-tagged variant (QADDANATVQLVESGGA (SEQ ID NO:61), instead of QVQLVESGGA (amino acids 1-10 of SEQ ID NO:9) in wildtype GBP) and also a C-terminal glyco-HIS-tagged variant (VSSLQAAAAAANATVAAASGDVWDIHHHHHH (SEQ ID NO:62), instead of VSSHHHHHH (amino acids 113-121 of SEQ ID NO:9) in wildtype (HIS-tagged) GBP). All the GBP variants were equipped with a C-terminal histidine-tag (6×HIS) which facilitates purification and/or detection.

The amino acid sequence of nanobody GBP is depicted in SEQ ID NO: 9. In SEQ ID NO: 9 the CDR1, CDR2 and CDR3 regions are underlined.

SEQ ID NO: 10 depicts CDR1, SEQ ID NO: 11 depicts CDR2, SEQ ID NO: 12 depicts CDR3, SEQ ID NO: 13 depicts FR1, SEQ ID NO: 14 depicts FR2, SEQ ID NO: 15 depicts FR3 and SEQ ID NO: 16 depicts FR4.

```
(121 amino acids)
SEQ ID NO 9:
QVQLVESGGALVQPGGSLRLSCAASGFPVNRYSMRWYRQAPGKEREWV

AGMSSAGDRSSYEDSVKGRFTISRDDARNTVYLQMNSLKPEDTAVYYC

NVNVGFEYWGQGTQVTVSSHHHHHH
```

(CDR1): SEQ ID NO: 10

GFPVNRYS (CDR2): SEQ ID NO: 11

MSSAGDRSS (CDR3): SEQ ID NO: 12

NVNVGFE (FR1): SEQ ID NO: 13

QVQLVESGGALVQPGGSLRLSCAAS (FR2): SEQ ID NO: 14

MRWYRQAPGKEREWVAG (FR3): SEQ ID NO: 15

YEDSVKGRFTISRDDARNTVYLQMNSLKPEDTAVYYC (FR4): SEQ ID NO: 16

YWGQGTQVTVSS

FIG. 3 depicts the amino acid alignment of the GBP nanobody with reference nanobody 3K74 from Example 1. N-linked glycosylation signatures were introduced in the GBP protein at the hypothetical locations identified through rational analysis of the 3K74 reference nanobody crystal structure. The specific mutations introduced to obtain N-glycan acceptor sites in nanobody GBP are depicted in FIG. 4.

Several chimeric genes were constructed: the coding sequences of the wild type GBP nanobody and the different mutants with introduced N-glycosylation acceptor sites in specific positions as depicted in FIG. 4 were operably linked to the AOX1 promoter (a methanol inducible promoter) of *Pichia pastoris*. The resulting expression vectors were introduced in 3 different strains of *Pichia pastoris*: wild type (WT), GlycoSwitch M5 (GSM5) and GlycoDelete (GD). The GlycoSwitch M5 strain modifies its glycoproteins predominantly with Man5GlcNAc2 structures (Jacobs, P. P. et al., (2009) Nat Protoc. 4(1)) while proteins expressed in the GlycoDelete strain are homogeneously modified with single GlcNAc residues (see for example Claes, K. et al. (2016) ACS Synth Biol. 5(10) and the general GlycoDelete technology which is discussed in the application WO2010015722).

Figure 5:
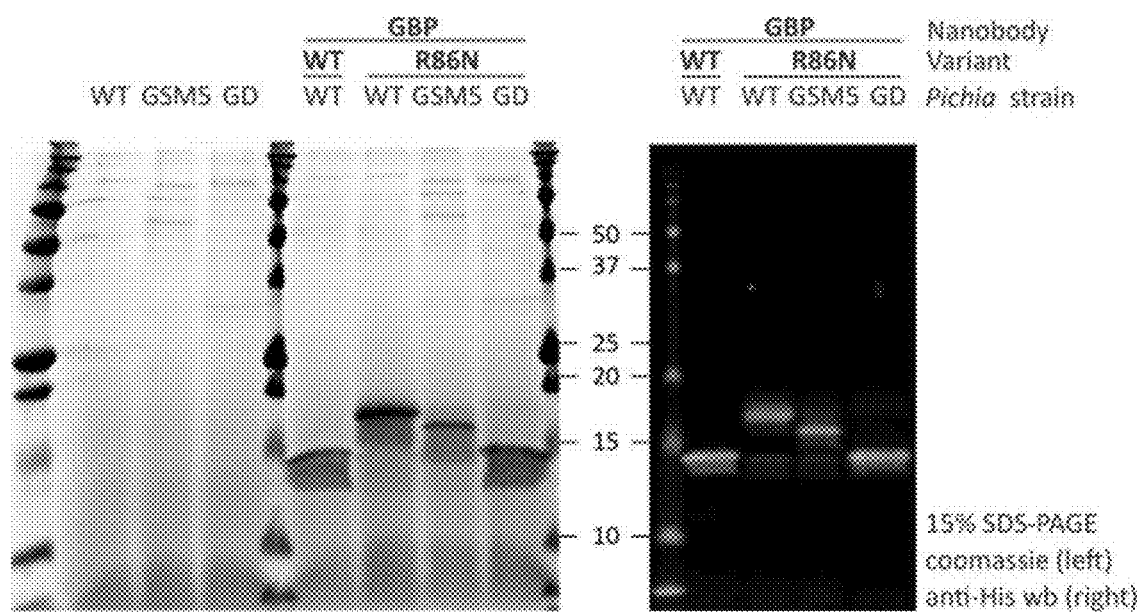
FIG. 5: Coomassie and anti-HIS western blot of nanobody GBP and the GBP-R86N variant (AHo numbering), expressed in *Pichia pastoris* wildtype (WT), Glyco-SwitchM5 (GSM5), and GlycoDelete (GD) strains.
Figure 6:
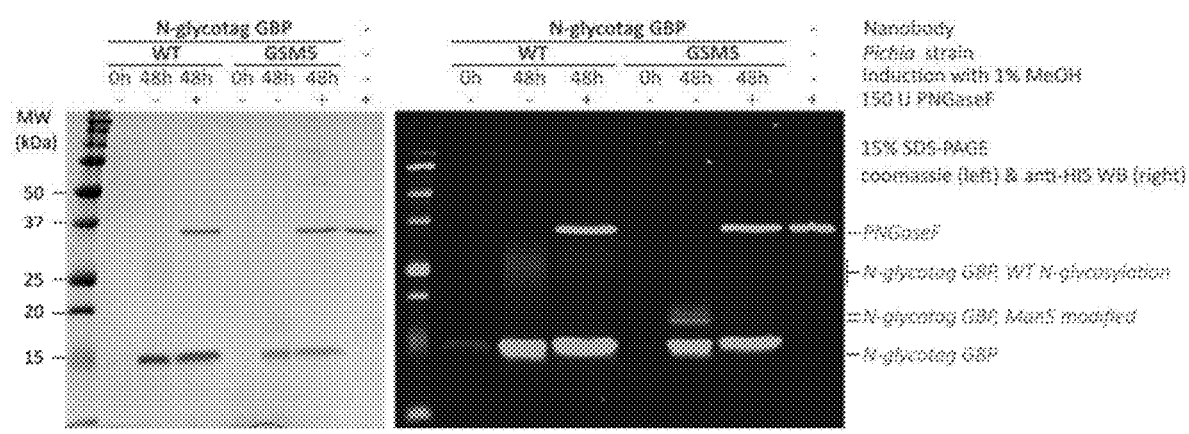
FIG. 6: Coomassie and anti-HIS western blot (or His6-specific western blot which is equivalent language) analysis of the N-glycotag variant of GBP, expressed in *Pichia pastoris* wildtype (WT) and GlycoSwitchM5 (GSM5). Samples were either mock-treated or PNGaseF-digested to remove N-glycans.
Figure 7:
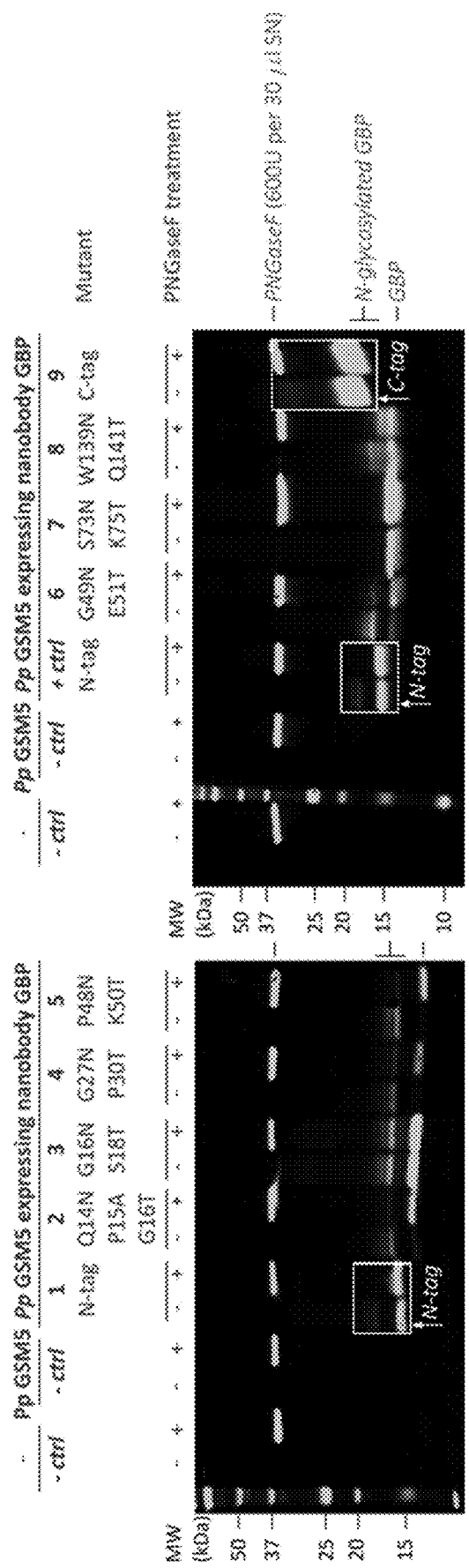
FIG. 7: Coomassie and anti-HIS WB analysis of 9 'glycovariants' of GBP, expressed in *Pichia GlycoSwitchM5* (GSM5). Samples were either mock-treated or PNGaseF-digested to remove N-glycans. White boxes indicate an increase in molecular weight due to addition of the N- (8 amino acids) or C- (22 amino acids) terminal glycotag amino acid sequence.

Subsequently, the different recombinant *Pichia pastoris* cultures were first grown in medium containing glycerol as the sole carbon source for 48 h at 28° C., and subsequently recombinant protein expression was induced by substitution of glycerol for methanol. After another 48 hours at 28° C., the growth medium (supernatant) was collected of each recombinant culture. The culture supernatants were subsequently either treated with the endoglycosidase PNGaseF (to remove the N-glycans) or mock treated, and assayed via Coomassie Blue stained SDS-PAGE and His-tag-specific Western Blot. Results of this analysis are shown in FIGS. 5, 6 and 7.

Our data show that glycosylation of nanobody GBP could be obtained for almost all the glycovariants thereof (except for the S73N-K75T variant (aHo numbering)) albeit with varying efficiency of N-glycosylation. For an overview specifying glycosylation efficiency see Table 1. Please note that this is also shown in the upper part of FIG. 4 (indicated as +++, + and − for glycosylation efficiency). Remarkably, 4 specific positions which lead to very efficient glycosylation were identified in the nanobody protein structure: position 14, position 27, position 48 and position 86. Also remarkably, two of these positions (27 and 86) have never been described for nanobodies with respect to introduction of N-glycan sites. Positions 14 and 48 are cited accidently in WO2016150845. Positions 14, 27, 48 and 86 are according to the Aho numbering.

Figure 8:
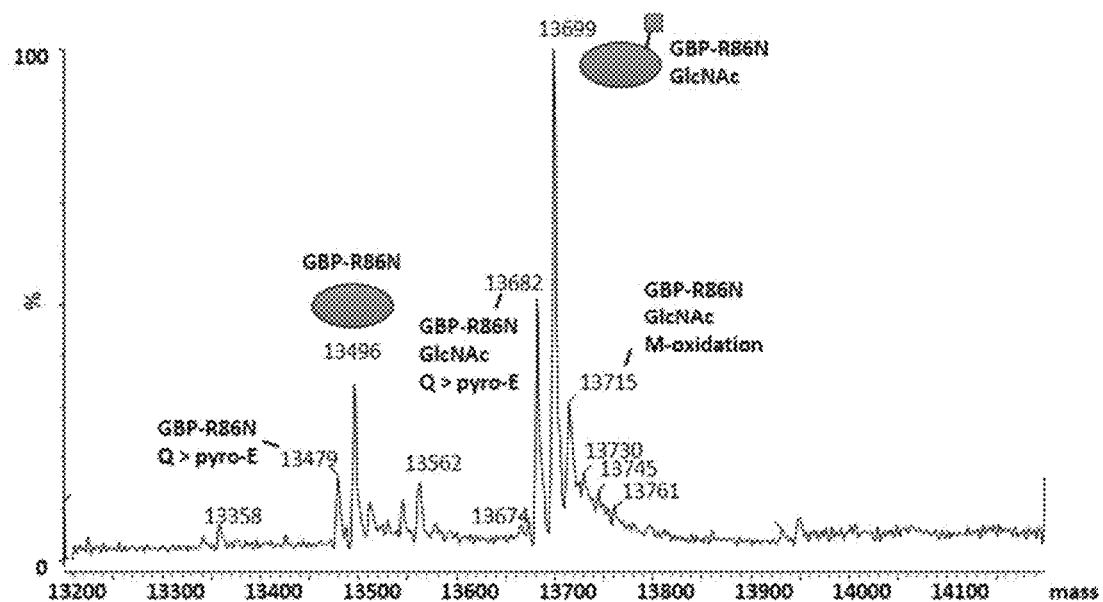
FIG. 8: ESI-QTOF MS analysis of nanobody GBP-R86N produced in the *Pichia pastoris* GlycoDelete (GD) strain. The N-glycosylated variant is detected at 13699 Da, while the non-glycosylated fraction is detected at 13496 Da.

In particular the highly efficiently glycosylated GBP-R86N variant (aHo numbering)—modified in the loop between the D and E strand—produced in the *Pichia pastoris* GlycoDelete background was further characterized in detail after purification using standard Ni2+ affinity chromatography and gel filtration, and subsequently analyzed using a ESI-QTOF mass spectrometer. The results are depicted in FIG. 8.

Nanobody GBP-R86N predominantly occurred in its glycosylated form. We show that this glycovariant allows for a very efficient glycosylation.

Figure 13:
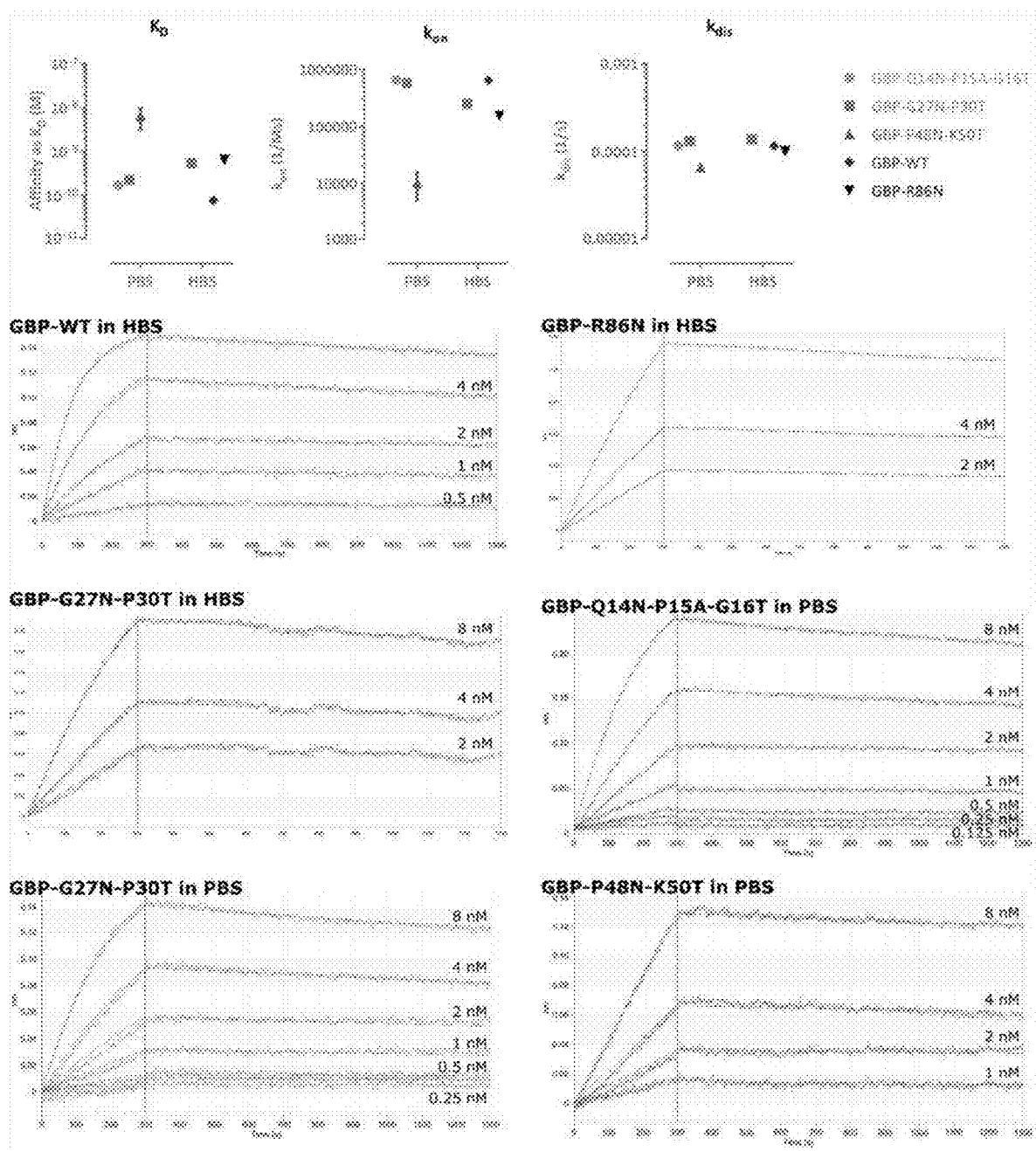
FIG. 13: GBP N-glycosylation variants (except GBP-P48N-K50T) bind their antigen GFP with similar characteristics as the unmodified GBP-WT. Nanobodies were produced in *Pichia pastoris* GlycoSwitchM5 (GSM5, Man5GlcNAc2 glycans) and purified via IMAC and SEC, eluted in either phosphate-buffered saline (PBS) or HEPES-buffered saline (HBS). Biolayer interferometry (BLI) was performed with 100 nM biotinylated Avitag-GFP immobilized on streptavidin tips. Affinity for two-fold dilution series of GBP glycovariants (8 to 0.125 nM) was measured in a 96-well format at 25° C. A summary of affinity parameters is shown above, calculated by ForteBio Data Analysis 9.0 (error bars indicate SEM).

To verify whether nanobody functionality was retained, we analyzed thermal stability and GFP binding affinity of both unmodified GBP nanobody and the four selected glycosylation variants at positions 14, 27, 48 and 86. Selected glycovariants were recombinantly produced in *Pichia pastoris* Kai3 (see Vervecken, N. et al (2007) Modification of the N-glycosylation pathway to produce homogeneous, human-like glycans using GlycoSwitch plasmids, in: J. M. Cregg (Ed.), *Pichia* Protocols, Humana Press, New York, pp. 119-138) a *Pichia* strain that generates Man5GlcNAc2 type N-glycans on recombinant proteins. Melting curves of GBP-WT and its glycovariants were obtained in a thermal shift assay using SYPRO Orange dye in a qPCR machine (Huynh K & Partch C L in *Current Protocols in Protein Sciences* 79, 2015). If a Man5GlcNAc2 type N-glycan is introduced at position 14, 27 or 48, the melting curve shape changes: it shows only one denaturation peak instead of the two denaturation peaks observed for GBP-WT and glycovariant R86N (see FIG. 12). However, the temperature at which thermal denaturation is initiated does not shift. Remarkably, we observed that nanobody function (antigen binding) is not impaired by the presence of an N-glycan in the four specific regions: GFP binding affinity is in the sub-nanomolar range (see FIG. 13). Only when a Man5GlcNAc2 type N-glycan occurs at position 48, antigen affinity is mildly decreased (dissociation constant $K_D$ is increased), mostly due to a decreased association rate ($k_{on}$) (see FIG. 13).

Example 4: Generalization of the Approach

To evaluate if we could extrapolate these findings to other nanobodies, we introduced N-linked-glycosylation signatures in several other nanobodies. In nanobody Nb41 (which is designated as NbCA4141 in Claes, K. et al (2016) *ACS Synth Biol.* 5(10)), we introduced an N-glycosylation sequon at the site corresponding to K86N in reference nanobody 3K74 and R86N in the GBP nanobody. The sequence of Nb41 is depicted in SEQ ID NO: 17. SEQ ID NO: 18 depicts CDR1, SEQ ID NO: 19 depicts CDR2, SEQ ID NO: 20 depicts CDR3, SEQ ID NO: 21 depicts FR1, SEQ ID NO: 22 depicts FR2, SEQ ID NO: 23 depicts FR3 and SEQ ID NO: 24 depicts FR4.

In nanobodies F-VHH-4 and F-VHH-L66 (Rossey, I. et al. (2017) *Nat. Commun.* 8, 14158), we introduced N-glycosylation sequons at the sites corresponding to G27N and/or R86N in GBP, thus obtaining nanobodies carrying either 1 or 2 N-linked glycosylation signatures. The sequences of F-VHH-4 and F-VHH-L66 are depicted in SEQ ID NO: 25 and SEQ ID NO: 26, respectively.

```
(129 amino acids)
SEQ ID NO: 17:
QVQLQESGGGLVQPGGSLRLSCVASGSIFSINAMGWYRQAPGKQREL

VAAISSGGRTNYADSVKGRFTISRDNAKNTVHLQMNSLKPEDTAVYY

CNVGSWGFRSHSYLSGSSWGQGTQVTVSSHHHHHH
```

The 3 CDR regions are underlined

```
(CDR1):
                                          SEQ ID NO: 18
GSIFSINA (CDR2):
                                          SEQ ID NO: 19
ISSGGRTN (CDR3):
                                          SEQ ID NO: 20
NVGSWGFRSHSYLSGS (FR1):
                                          SEQ ID NO: 21
QVQLQESGGGLVQPGGSLRLSCVAS (FR2):
                                          SEQ ID NO: 22
MGWYRQAPGKQRELVAA (FR3):
                                          SEQ ID NO: 23
YADSVKGRFTISRDNAKNTVHLQMNSLKPEDTAVYYC
```

-continued (FR4):
SWGQGTQVTVSS
SEQ ID NO: 24

(F-VHH-4):
(135 amino acids)
SEQ ID NO: 25
QVQLQESGGGLVQPGGSLRLSCAASGFTLDYYYIGWFRQAPGKEREAV

SCISGSSGSTYYPDSVKGRFTISRDNAKNTVYLQMNSLKPEDTAVYYC

ATIRSSSWGGCVHYGMDYWGKGTQVTVSSGSHHHHHHHH (F-VHH-L66):
(135 amino acids)
SEQ ID NO: 26
QVQLQESGGGLVQPGGSLRLSCAASGFTLDYYYIGWFRQAPGKEREGV

SCISSSHGSTYYADSVKGRFTISRDNAKNTVYLQMNSLKPEDTAVYYC

ATVAVAHFRGCGVDGMDYWGKGTQVTVSSGSHHHHHHHH

FIG. 9 depicts a sequence alignment of nanobodies Nb41, F-VHH-4, and F-VHH-L66 with nanobodies GBP and 3K74

Figure 10:
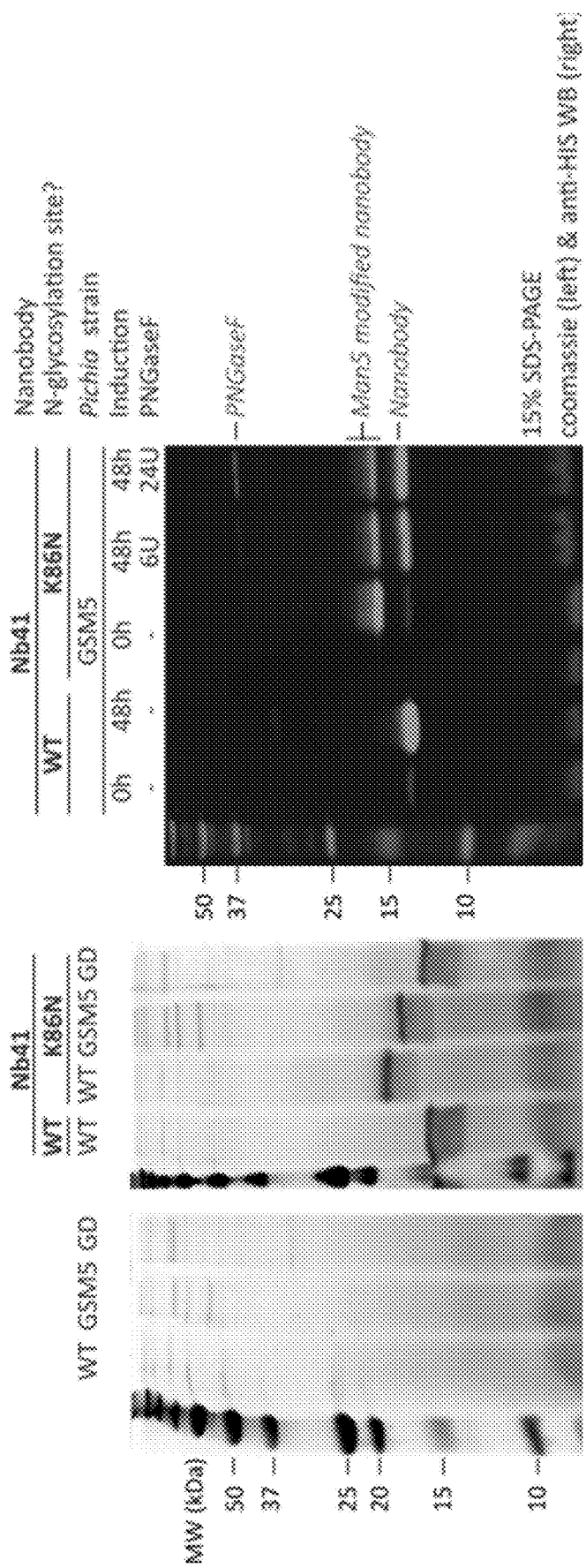
FIG. 10: Coomassie and anti-HIS WB analysis of Nb41 and the Nb41-K86N variant, expressed in *Pichia pastoris* wildtype (WT), GlycoSwitchM5 (GSM5), and GlycoDelete (GD). Samples were either mock-treated or PNGaseF-digested to remove N-glycans.

Wild type Nb41 (without any N-glycosylation signatures) was recombinantly produced in *Pichia* WT, similarly as outlined in example 3. In Nb41, the K86N mutation is equivalent to the GBP-R86N mutation. Nb41-K86N was recombinantly produced in *Pichia* WT, *Pichia* GSM5 and *Pichia* GlycoDelete, similarly as outlined in example 3. After induction of expression, the supernatants of all recombinant productions were collected, PNGaseF-treated or mock treated, and assayed via Coomassie Blue stained SDS-PAGE and/or His-tag-specific Western Blot analysis. A compilation of the data is shown in FIG. 10.

For Nb41, we show that glycosylation was not present in the WT nanobody (as expected), while the introduction of a glycosylation signature at position 86 (AHo numbering) allowed for an efficient N-glycan modification.

Figure 23:
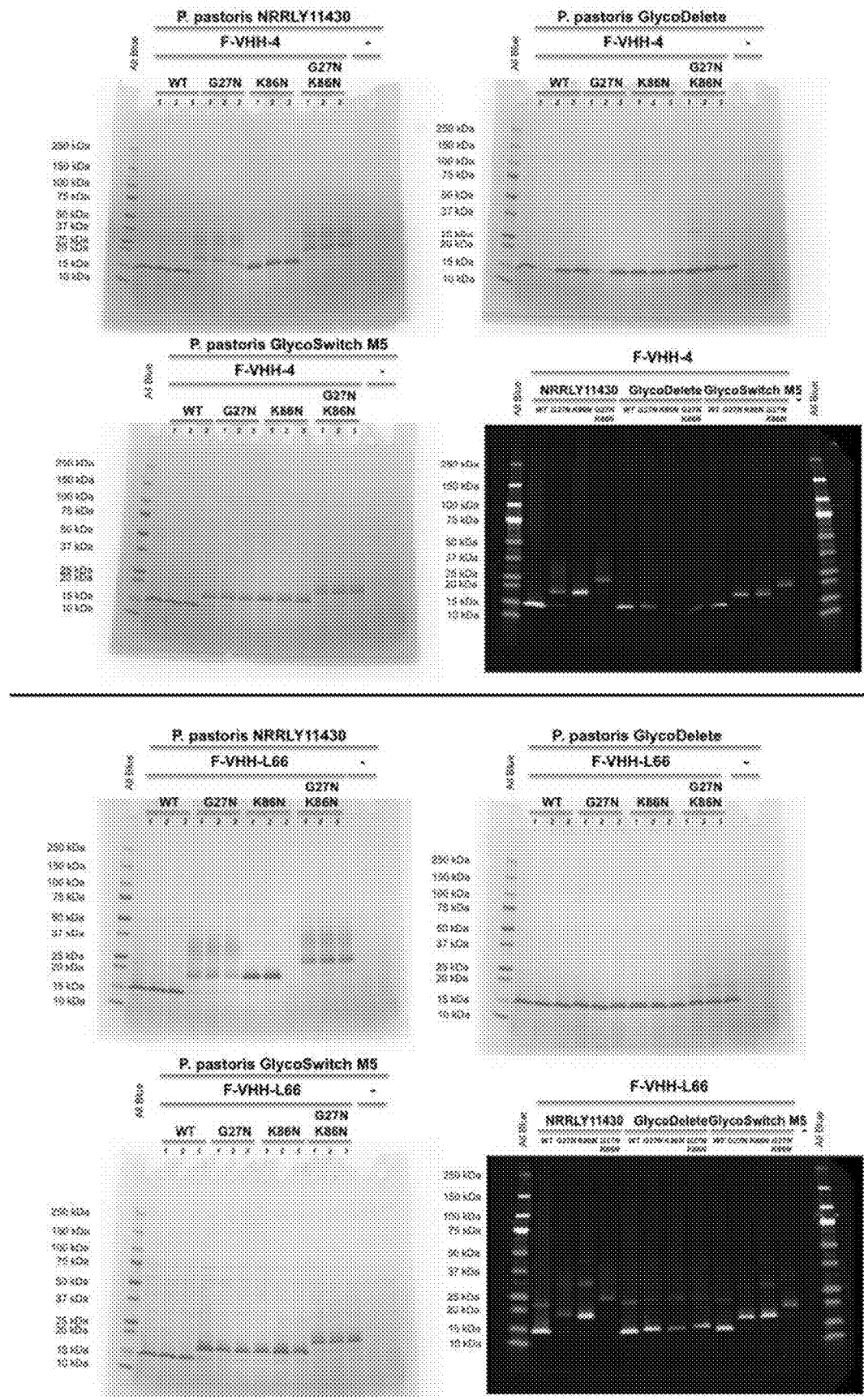
FIG. 23: Coomassie and anti-HIS western blot analysis of nanobody F-VHH-4 variants (upper panel) and F-VHH-L66 variants (lower panel) produced in the *Pichia pastoris* wildtype (NRRLY11430), GlycoSwitchM5, and GlycoDelete strains. For the Coomassie analysis, supernatants of 3 different clones were tested for each nanobody—*Pichia* strain combination; for the western blot analysis, supernatant of 1 representative clone was analyzed.

Wild type F-VHH-4 and F-VHH-L66 (without any N-glycosylation signatures), as well as variants thereof carrying a G27N and/or a K86N mutation (corresponding to G27N and R86N in GBP, respectively; AHo numbering), were recombinantly produced in *Pichia* WT, *Pichia* GSM5 (equivalent name for *Pichia* Kai3 strain) and *Pichia* GlycoDelete, similarly as outlined in example 3. After induction of expression, the supernatants of all recombinant productions were collected and assayed via Coomassie Blue stained SDS-PAGE analysis, His-tag-specific Western Blot analysis, and mass spectrometry analysis. Coomassie Blue and Western Blot data are shown in FIG. 23.

For F-VHH-4 and F-VHH-L66, we found that glycosylation was not present in the WT nanobody (as expected), while the introduction of a glycosylation signature at position 27 or 86 (AHo numbering) allowed for an efficient N-glycan modification. Simultaneous introduction of an N-linked glycosylation signature at position 27 and at position 86 in the same backbone led to efficient N-glycan modification at both sites.

To objectively assess glycosylation efficiencies at positions 27 and 86 (AHo numbering), we performed densitometry analysis on the His-tag-specific western blots of VHH glycovariants produced in *Pichia pastoris* GlycoSwitchM5. Site occupancy of F-VHH-4-G27N was determined as 96% (FIG. 23), that of F-VHH-4-R86N was 93% (FIG. 23), that of GBP-G27N-P30T was 86% (FIG. 7) and that of GBP-R86N was 93% (FIG. 5). For all other nanobody variants with N-glycosylation sites at position 27 and 86, the lower band (corresponding to unglycosylated nanobody) could not be detected if fluorescence gain was set low enough to prevent overexposure of the upper band (corresponding to the N-glycosylated nanobody). This suggests at least 80% N-glycosylation.

A compilation of the glycosylation efficiencies obtained with the GBP, Nb41, F-VHH-4, and F-VHH-L66 nanobodies in the different recombinant *Pichia pastoris* backgrounds is summarized in Table 1 (see also FIG. 11 specifically for the GBP mutants).

TABLE 1

Overview of N-glycosylation nanobody variants.

| Protein | | | Pichia | N-glycosylation | | | |
|---|---|---|---|---|---|---|---|
| Vector | Insert | Modification AHo | Strain | Type | Efficiency | Validation | Where? |
| pKai61 | GBP | | WT | | | | |
| pKai61 | GBP | N-glycotag | GSM5 | Man5 | + | WB | N-terminus |
| pKai61 | GBP | C-glycotag | GSM5 | HighMan | + | WB | C-terminus |
| pKai61 | GBP | Q14N-P15A-G16T | GSM5 | Man5 | +++ | WB | loop A-B |
| pKai61 | GBP | G16N-S18T | GSM5 | Man5 + HighMan | + | WB | loop A-B |
| pKai61 | GBP | G27N-P30T | GSM5 | Man5 | +++ | WB | loop B-C |
| pKai61 | GBP | P48N-K50T | GSM5 | Man5 | +++ | WB | loop C-C' |
| pKai61 | GBP | G49N-E51T | GSM5 | Man5 | + | WB | loop C-C' |
| pKai61 | GBP | S73N-K75T | GSM5 | Man5 | – | WB | loop C''-D |
| pKai61 | GBP | W139N-Q141T | GSM5 | Man5 | + | WB | loop F-G |
| pKai61 | GBP | R86N | WT | HighMan | +++ | CB | loop D-E |
| pKai61 | GBP | R86N | GD | GlcNAc | +++ ±70%* | MS | loop D-E |
| pKai61 | GBP | R86N | GSM5 | Man5 | +++ | CB | loop D-E |
| pKai61 | Nb41 | | WT | | | | |
| pKai61 | Nb41 | K86N | WT | HighMan | +++ | CB | loop D-E |
| pKai61 | Nb41 | K86N | GD | GlcNAc | +++ | CB | loop D-E |
| pKai61 | Nb41 | K86N | GSM5 | Man5 | +++ | WB | loop D-E |
| ppExpr | F-VHH-4 | | WT | | | CB/WB/MS | |
| ppExpr | F-VHH-4 | | GD | | | CB/WB/MS | |
| ppExpr | F-VHH-4 | | GSM5 | | | CB/WB/MS | |
| ppExpr | F-VHH-4 | G27N | WT | HighMan | +++ | CB/WB/MS | loop B-C |
| ppExpr | F-VHH-4 | G27N | GD | GlcNAc | +++ | CB/WB/MS | loop B-C |
| ppExpr | F-VHH-4 | G27N | GSM5 | Man5 | +++ | CB/WB/MS | loop B-C |

TABLE 1-continued

Overview of N-glycosylation nanobody variants.

| Vector | Protein Insert | Modification AHo | Pichia Strain | N-glycosylation Type | Efficiency | Validation | Where? |
|---|---|---|---|---|---|---|---|
| ppExpr | F-VHH-4 | K86N | WT | HighMan | +++ | CB/WB/MS | loop D-E |
| ppExpr | F-VHH-4 | K86N | GD | GlcNAc | +++ | CB/WB/MS | loop D-E |
| ppExpr | F-VHH-4 | K86N | GSM5 | Man5 | +++ | CB/WB/MS | loop D-E |
| ppExpr | F-VHH-4 | G27N + K86N | WT | HighMan | +++ | CB/WB/MS | loop B-C, loop D-E |
| ppExpr | F-VHH-4 | G27N + K86N | GD | GlcNAc | +++ | CB/WB/MS | loop B-C, loop D-E |
| ppExpr | F-VHH-4 | G27N + K86N | GSM5 | Man5 | +++ | CB/WB/MS | loop B-C, loop D-E |
| ppExpr | F-VHH-L66 | | WT | | | CB/WB/MS | |
| ppExpr | F-VHH-L66 | | GD | | | CB/WB/MS | |
| ppExpr | F-VHH-L66 | | GSM5 | | | CB/WB/MS | |
| ppExpr | F-VHH-L66 | G27N | WT | HighMan | +++ | CB/WB/MS | loop B-C |
| ppExpr | F-VHH-L66 | G27N | GD | GlcNAc | +++ | CB/WB/MS | loop B-C |
| ppExpr | F-VHH-L66 | G27N | GSM5 | Man5 | +++ | CB/WB/MS | loop B-C |
| ppExpr | F-VHH-L66 | K86N | WT | HighMan | +++ | CB/WB/MS | loop D-E |
| ppExpr | F-VHH-L66 | K86N | GD | GlcNAc | +++ | CB/WB/MS | loop D-E |
| ppExpr | F-VHH-L66 | K86N | GSM5 | Man5 | +++ | CB/WB/MS | loop D-E |
| ppExpr | F-VHH-L66 | G27N + K86N | WT | HighMan | +++ | CB/WB/MS | loop B-C, loop D-E |
| ppExpr | F-VHH-L66 | G27N + K86N | GD | GlcNAc | +++ | CB/WB/MS | loop B-C, loop D-E |
| ppExpr | F-VHH-L66 | G27N + K86N | GSM5 | Man5 | +++ | CB/WB/MS | loop B-C, loop D-E |

*Pichia* strains: WT = wildtype, GSM5 = GlycoSwitchM5 (alternative name for the *Pichia* Kai3 strain), GD = GlycoDelete.
N-glycosylation types: HighMan = high-mannose N-glycosylation, Man5 = Man5GlcNAc2 and GlcNAc = single GlcNAc residue.
*For nanobody GBP-R86N produced in *Pichia* GlycoDelete, N-glycosylation was validated and quantitated by ESI-QTOF mass spectrometry.
CB = Coomassie Brilliant Blue stained SDS-PAGE analysis, WB = His-tag-specific western blot analysis, MS = Mass spectrometric analysis.

Figure 14:
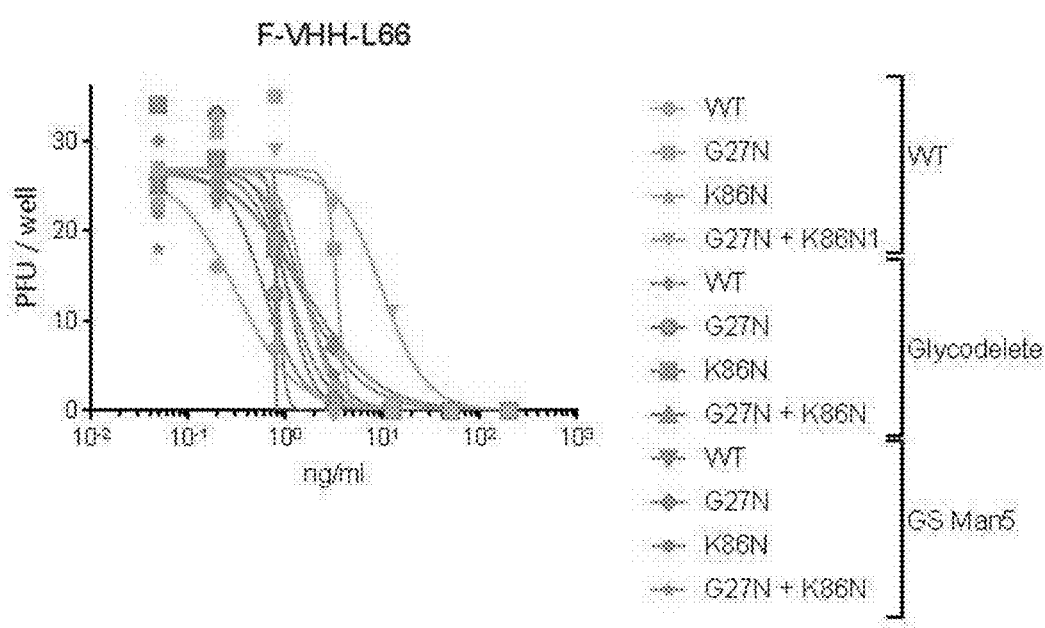
FIG. 14: Neutralization assay for RSV specific VHH F-VHH-L66. F-VHH-L66 was produced both in wild type (wt) *Pichia pastoris* and the GlycoSwitchM5 (GSM5) and Glycodelete (GD) strains.

The RSV-specific VHHs F-VHH-L66 and F-VHH-4, produced in the different *Pichia* backgrounds (WT, GSM5 (indicated in FIG. 14 as GS Man5), and GlycoDelete) were assayed for their neutralizing capacity in an RSV neutralization assay. Briefly: Vero cells were seeded in 96 well plates at a density of 15.000 cells/well and cultivated at 37° C. The following day, 4-fold serial dilutions of purified VHH in Optimem (starting at 400 ng/ml) were mixed with equal volumes of RSV A2 (1.34 PFU/μl), and incubated for 30 minutes at 37° C. Subsequently, the Vero cells were washed once with Optimem, and the Optimem was replaced with 50 μl of the VHH-virus mixture. Cells were incubated at 37° C. for 3 h. After 3 h, 50 μl of DMEM+1.2% avicel+1% FCS was added to the cells, and cells were further incubated at 37° C. for 3 days. Finally, cells were fixed with 2% paraformaldehyde and stained with polyclonal goat anti-RSV antibodies, and plaques were counted. Results for the VHH F-VHH-L66 are shown in FIG. 14.

Our results show that the introduction of the glycosylation sites in these VHHs does not block VHH binding to and neutralization of RSV. Nevertheless, an effect of (the types of) glycan(s) present can be discerned. Glycan size appears to be inversely correlated with the neutralizing capacity of the VHH, suggesting that glycans with a large hydrodynamic radius interfere more with neutralization than smaller glycans (WT glycans>Man5 glycans>GlycoDelete glycans). Moreover, for these VHHs, a glycan at site 27 (AHo numbering) seems to hinder neutralization slightly more than a glycan at site 86 (AHo numbering); the presence of a glycan at both sites has an additive effect.

Thus we can surprisingly conclude that the introduction of small GlycoDelete type glycans (GlcNAc, LacNAc and sialyl-LacNAc) at different positions in a VHH does not lead to a reduction of the efficiency of a VHH as herein shown for VHHs directed to RSV virus.

We conclude that positions within ISVDs (here applied on nanobodies) which allow for efficient N-glycosylation can rationally be selected based on structural criteria, that these positions are conserved within ISVDs and that our concept can be applied to different nanobodies. Particularly preferred positions in the sequence of an ISVD which lead to efficient N-glycan production without encumbering the function of the ISVD are the two regions 83 to 88 and 27 to 40 (AHo numbering).

Example 5: Generalization of the Identified Position for Efficient N-Glycan Introduction in the Genus of ISVDs Sequences of 222 VHH encoding chains (a PDB search was carried out with query "VHH" or nanobody, selected one chain per resulting PDB ID of which either the macro-molecule name contains 'nanobody', 'nb', 'nab', 'vhh' or 'cab'; or the source species is *Camelus dromedarius, Lama glama* or *Vicugna* pacos; or the conserved amino acid sequence 'VQL' occurs in the first 40 amino acid residues) were extracted from the RCSB Protein Data Bank (in short PDB) and aligned using PyMOL (The PyMOL Molecular Graphics System, Version 1.3 Schrödinger, LLC.). In each of these VHHs, the regions between amino acids 83 and 88 (AHo) and between amino acids 27 and 40 (AHo) constitute amino acid strands linking beta strands of the secondary structure. Subsequently the presence of these conserved linker regions was confirmed in almost 100% (1667 out of 1668) of the VHH coding sequences aligned in the Antibody Variable Domain Database (ABVDDB). Without being limited to a particular hypothesis we reason that in these selected regions, a glycan substituent is projected away from the antigen-binding region, so that it minimally interferes with antigen recognition. We conclude that a glycosylation acceptor site introduced at a position located within these two conserved regions can be used for an introduction of an artificial N-glycan site which will predictably be efficiently N-glycosylated in all nanobodies.

Figure 16:
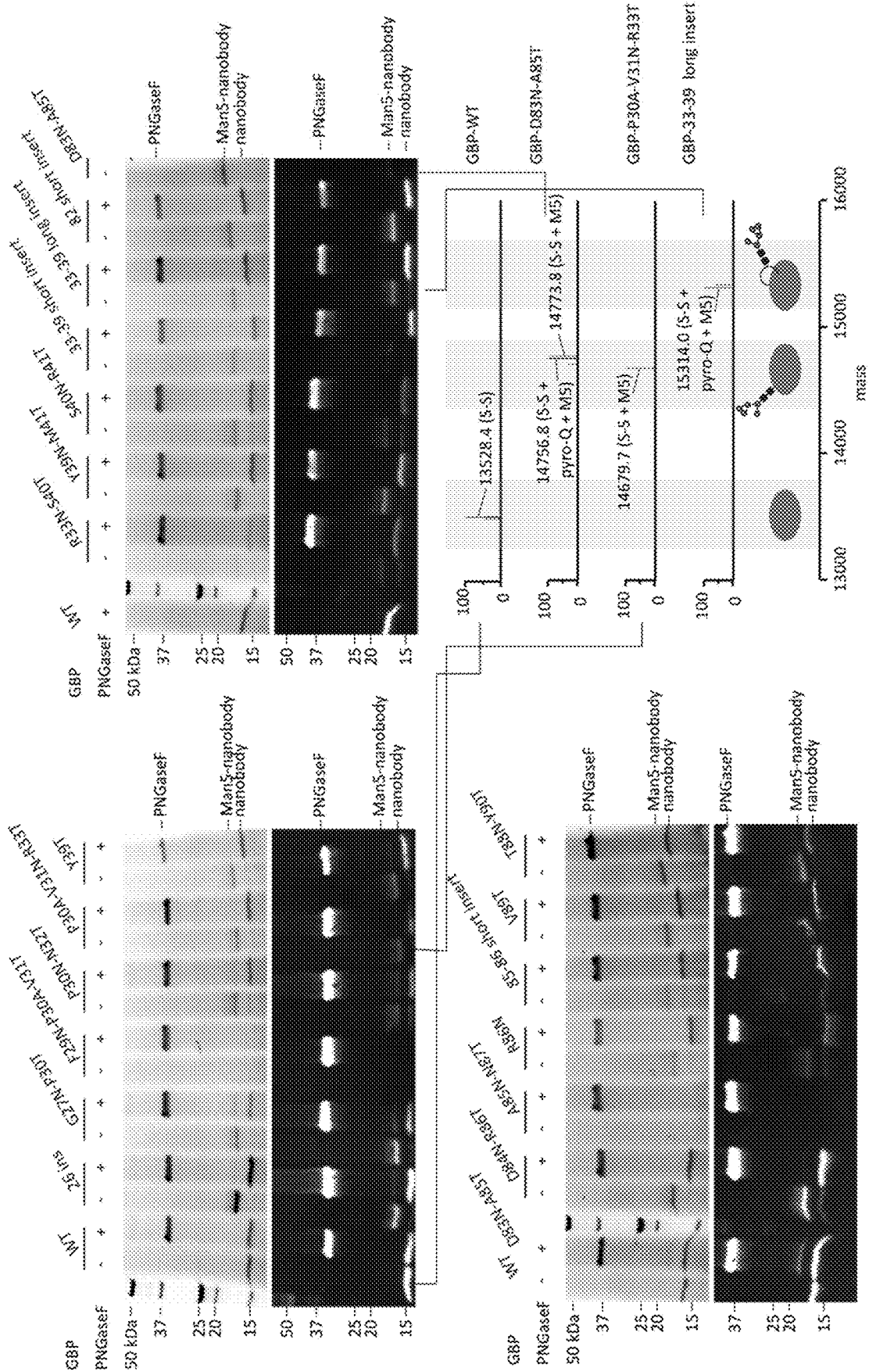
FIG. 16: N-glycans can be introduced at virtually any position of the two selected regions in nanobody GBP, but site occupancy is variable. GBP glycovariants were expressed in *Pichia pastoris* GlycoSwitchM5 (GSM5). Supernatants of all recombinant variants were collected, PNGaseF-treated or mock treated, and assayed for the presence of N-glycosylation on 14-20% gradient SDS-PAGE followed by Bio-Rad TGX stain-free detection (top) and His-tag-specific western blot analysis (bottom). Supernatant samples of wildtype GBP, a glycovariant in each selected region (GBP-P30A-V31N-R33T in region 27-40 and GBP-D84N-A85T in region 83-88) and a glycovariant containing an artificial insert (GBP-33-39-longinsert) were analyzed by intact protein mass spectrometry (bottom right). Masses of the latter three confirm a 1216 Da Man5GlcNAc2 glycan modification is present as schematically shown below. Normalized spectra are shown with normalized length (NL) 2.27E3 for GBP-WT, 4.29E3 for GBP-D83N-A85T, 7.64E2 for GBP-P30T-V31N-R33T and 2.14E3 for GBP-33-39-longinsert. S—S: single disulfide bond, pyroQ: N-terminal pyroglutamine residue, M5: Man5GlcNAc2 glycan modification.

In a next step, we generated a range of expression plasmids encoding GBP nanobody variants by introducing an N-x-T sequon at every single position between amino acids 83 and 88 (AHo) and between amino acids 27 and 40 (AHo), so that in each of the variants the N (Asn) is present in the sequon but at different positions (e.g. 82, 83, 84, 85, an artificially inserted sequence between 85 and 86, 86, 87, 88, 26, 27, 29, 30, 31, 32, 33, an artificially inserted sequence between 33 and 39, 39 or 40) (see FIG. 15). Please note that specifically for the GBP nanobody amino acid sequence AHo-numbering positions 28 and 34-38 do not exist. All these nanobody variants were produced in recombinant *Pichia pastoris* Kai3 strain as described above— variants with the amino acid at positions 29 and 85 mutated to arginine (F29N-P30A-V31T and A85N) were not efficiently transformed in *Pichia pastoris* and were not evaluated. Subsequently, supernatants of all recombinant variants were collected, PNGaseF-treated or mock treated, and assayed for the presence of N-glycosylation via Coomassie Brilliant Blue stained SDS-PAGE and/or His-tag-specific Western Blot analysis (see FIG. 16). The presence of N-glycans could be confirmed in each of the expressed nanobody variants; however, the efficiency of N-glycan addition (site occupancy) is strongly dependent on the exact amino acid position chosen for N-glycosylation sequon introduction (see Table 2). To confirm the glycans present are indeed (GlcNAc)$_2$Man$_5$, supernatant samples of wildtype GBP, a glycovariant in each selected region (GBP-P30A-V31N-R33T in region 27-40 and GBP-D84N-A85T in region 83-88) and a glycovariant containing an artificial insert in the first region (GBP-33-39-longinsert) were analyzed by intact protein mass spectrometry (FIG. 16 bottom right). For each glycovariant, a peak indicating the presence of a 1216 Da (GlcNAc)$_2$Man$_5$ modification was observed.

The above results show that nanobodies can effectively be glycosylated in rationally chosen, conserved regions where the presence of an N-glycan does not affect antigen recognition and protein fold. These data pave the way for glycan-mediated targeting and site-specific glycan-based conjugation strategies.

Example 6: Development of Glycan-Specific Conjugation Methods

The data from the previous examples convincingly show that ISVDs (exemplified by nanobodies) can be effectively glycosylated in rationally chosen, conserved regions where presence of a glycan does not affect antigen recognition and protein fold. These data pave the way for glycan-mediated targeting and site-specific glycan-based conjugation strategies of ISVDs. In the following examples, we are using nanobodies with simple and homogeneous N-linked glycans at artificially engineered N-glycosylation sites (as outlined in Examples 3, 4 and 5) for the application of glycan-specific conjugation methods. Indeed N-glycans comprising only GlcNAc and/or only LacNAc and/or only sialyl-LacNAc can be obtained by in vitro approaches or can be obtained in vivo via the GlycoDelete technology as described in WO2010015722 or via the GlycoDoubleDelete technology as described in WO2017005925). The simple N-glycans provide for a bio-orthogonal handle on the protein that can be used for coupling to a wide variety of desired moieties— e.g. PEG chains, chelators, toxic drugs etc. Different glycan-based conjugation chemistries are evaluated/optimized, using commercially available biotinylated PEG. Basically there exist two broad methods for conjugation: chemical conjugation as exemplified in example 7 and combined chemical and enzymatic conjugation methods as exemplified in example 8.

Example 7: Chemical Conjugation Strategies

In this example we show how a nanobody with an artificially introduced N-glycan at position 86 (Aho numbering) can be specifically modified with PEG-biotin on the glycan. The nanobody is first recombinantly expressed in a HEK293 GlycoDelete cell (see WO2010015722), a

TABLE 2

Overview of N-glycosylation GBP variants within selected regions.

| | Protein | | *Pichia* | | N-glycosylation | | |
|---|---|---|---|---|---|---|---|
| Vector | Insert | Modification | Strain | Type | Efficiency | Validation | Where? |
| pKai61 | GBP | F29N-P30A-V31T | GSM5 | | not transformed | | loop B-C |
| pKai61 | GBP | P30N-N32T | GSM5 | Man5 | ++ | WB | loop B-C |
| pKai61 | GBP | P30A-V31N-R33T | GSM5 | Man5 | ++ | WB | loop B-C |
| pKai61 | GBP | Y39T | GSM5 | Man5 | ++ | WB | loop B-C |
| pKai61 | GBP | R33N-S40T | GSM5 | Man5 | + | WB | loop B-C |
| pKai61 | GBP | Y39N-M41T | GSM5 | Man5 | +++ | WB | loop B-C |
| pKai61 | GBP | S40N-R41T | GSM5 | Man5 | + | WB | loop B-C |
| pKai61 | GBP | 34insert | GSM5 | Man5 | ++ | WB | loop B-C |
| pKai61 | GBP | 34longinsert | GSM5 | Man5 | ++ | WB | loop B-C |
| pKai61 | GBP | 26insert | GSM5 | Man5 | +++ | WB | loop B-C |
| pKai61 | GBP | D83N-A85T | GSM5 | Man5 | ++ | WB | loop D-E |
| pKai61 | GBP | D84N-R86T | GSM5 | Man5 | ++ | WB | loop D-E |
| pKai61 | GBP | A85N-N87T | GSM5 | | not transformed | | loop D-E |
| pKai61 | GBP | V89T | GSM5 | Man5 | ++ | WB | loop D-E |
| pKai61 | GBP | T88N-Y90T | GSM5 | Man5 | ++ | WB | loop D-E |
| pKai61 | GBP | 82insert | GSM5 | Man5 | ++ | WB | loop D-E |
| pKai61 | GBP | 85insert | GSM5 | Man5 | + | WB | loop D-E |

*Pichia* strain GSM5 = GlycoSwitchM5.
Man5 = Man5GlcNAc2.
*For nanobody GBP-R86N produced in *Pichia* GlycoDelete, N-glycosylation was quantitated by SDS-PAGE with Coomassie Brilliant Blue (CB) and anti-HIS western blot (WB) detection.
The origin of the pKai61 vector is described in Schoonooghe S et al (2009) *BMC Biotechnol.* 9, 70.

HEK293 GlycoDoubledelete cell (see WO2017005925), a *Pichia*-GlycoDelete cell, or a *Pichia*-GlycoDelete cell that overexpresses a galactosyltransferase. Depending on the GlycoDelete method used, a nanobody is obtained which is modified with glycans selected from the group consisting of GlcNAc, LacNAc and sialyl-LacNAc.

Figure 17:
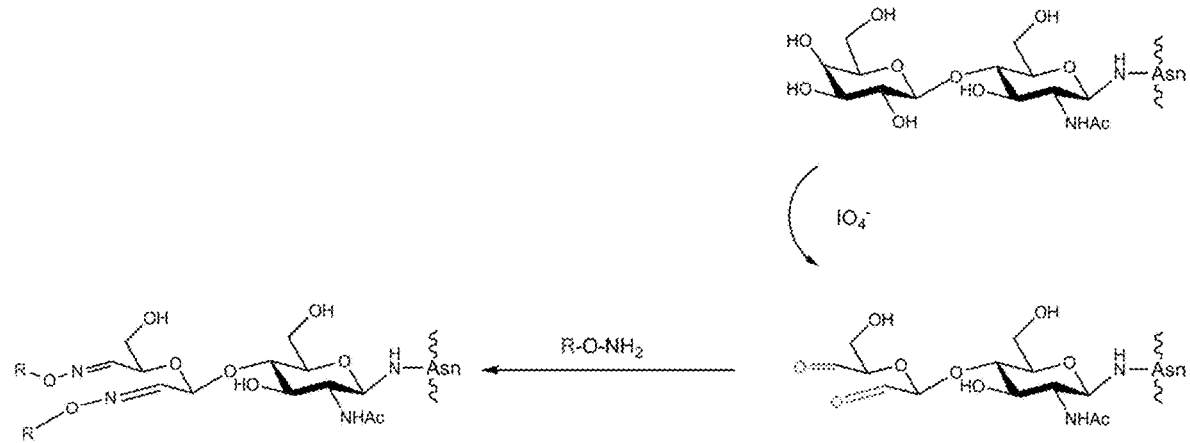
FIG. 17: Schematic outline of LacNAc-based periodate oxidation, coupled with subsequent oxime ligation.
Figure 18:
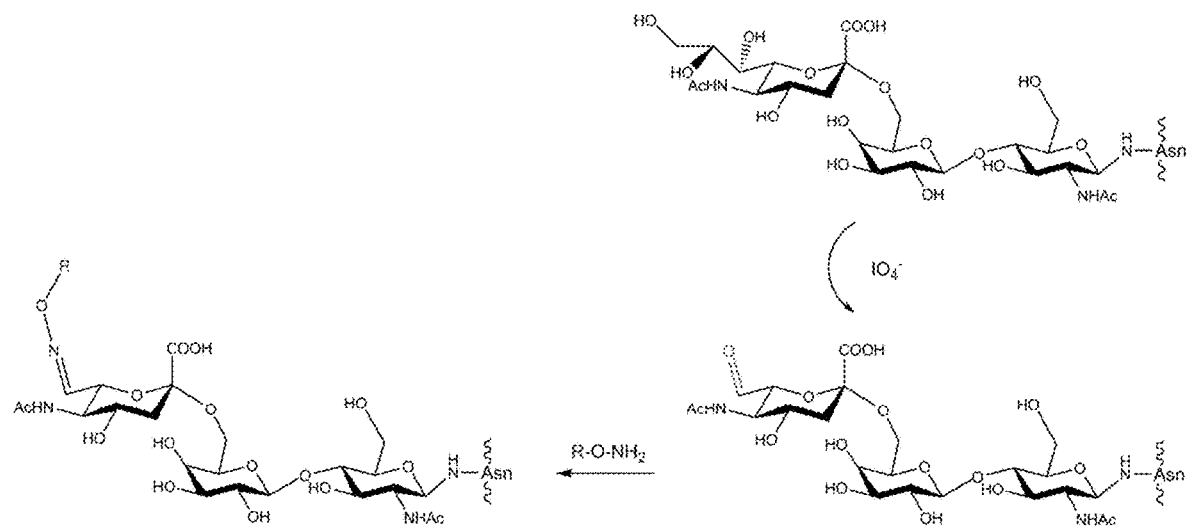
FIG. 18: Schematic outline of sialyl-LacNAc-based periodate oxidation, coupled with subsequent oxime ligation.

According to a first conjugation strategy, vicinal diol(s) in glycans are oxidized by sodium periodate ($NaIO_4$). Early versions of this chemistry have been in use for decades, e.g. to generate fluorescently labeled antibodies. Glyco-engineered nanobodies obtained via the GlycoDelete technology carry glycans on which periodate oxidation yields pure products (in contrast to the situation of wild type glycans). The LacNAc type glycans (GlcNAc-Gal) contain a single vicinal 'cis' diol in the galactose residue (at the C3 and C4 ring positions) which can be oxidized. The sialyl-LacNAc type glycans contain, in addition to the vicinal cis diol in the galactose residue, vicinal diols in the glycerol side chain of the terminal sialic acid residue that are susceptible to periodate oxidation. The vicinal diols in sialic acid are much more easily oxidized by periodate than galactose, allowing the use of mild oxidation conditions favouring sialic acid oxidation while still retaining product homogeneity. Periodate oxidation of the vicinal diols present in the glycan creates free aldehyde groups, which can readily react with aminooxy-containing molecules to form oximes, which are immediately stable in water. Alternatively, the free aldehydes can be reacted with hydrazine-containing molecules to form a stable hydrazone linkage, or they can be linked to amine-containing molecules via reductive amination. The LacNAc and sialyl-LacNAc glycans conjugated in this manner retain an intact GlcNAc residue directly linked to the protein asparagine, which is favourable in terms of conjugate degradability in the lysosome. The schematic outline of LacNAc- and sialyl-LacNAc-based periodate oxidation, coupled with subsequent oxime ligation, is illustrated in FIGS. 17 (LacNAc) and 18 (sialyl-LacNAc).

Briefly, GBP carrying an R86N mutation was recombinantly produced in HEK293 GlycoDelete cells and purified, yielding a mixture of non-glycosylated protein and protein carrying either a single LacNAc or sialyl-LacNAc chain. The purified protein was then subjected to mild periodate oxidation and subsequent oxime ligation to a short biotinylated and aminooxy-modified PEG chain. Mass spec analysis showed that the PEG chain was selectively linked to sialyl-LacNAc-carrying GBP.

Example 8: Chemo-Enzymatic Conjugation Strategies

Figure 19:
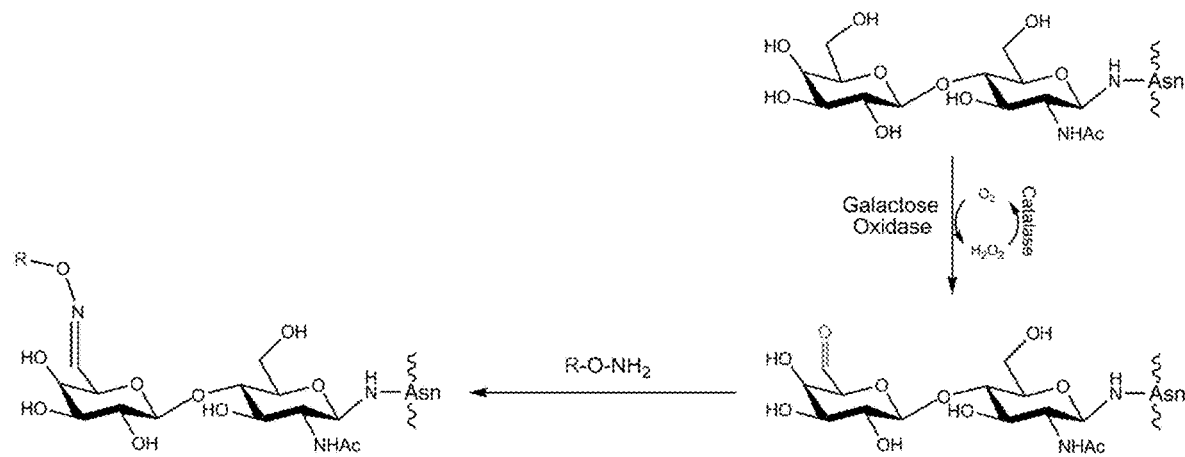
FIG. 19: Schematic outline of the GAO-based LacNAc oxidation, coupled with subsequent oxime ligation.
Figure 20:
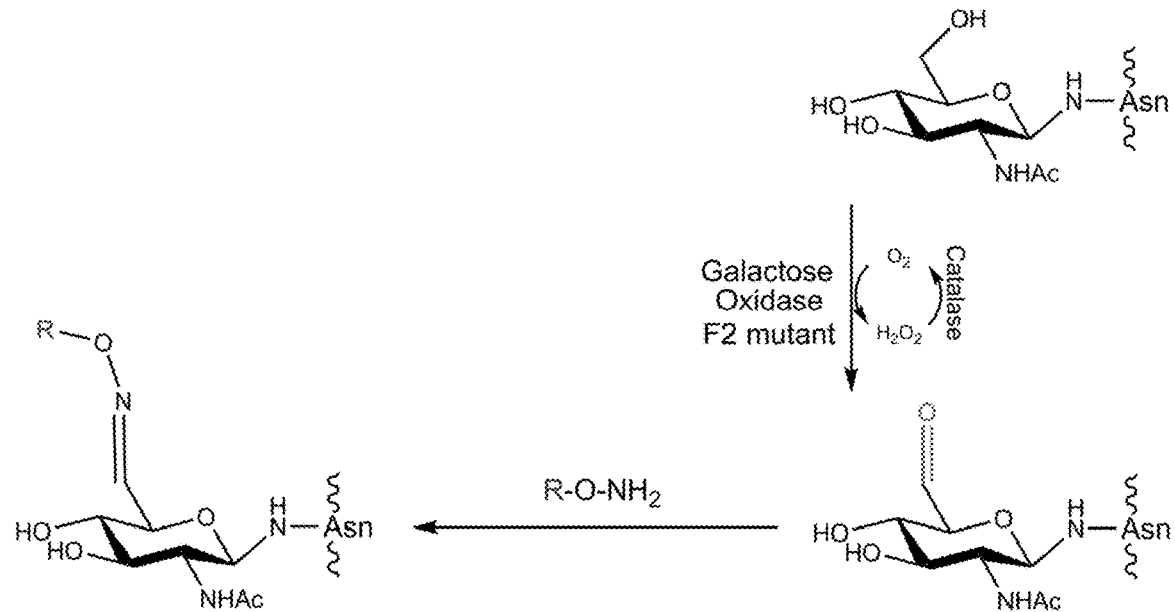
FIG. 20: Schematic outline of GAO-F2-based GlcNAc oxidation, coupled with subsequent oxime ligation.

In this example, alternative conjugation strategies are applied. Instead of periodate oxidation of the glycan, we use the enzyme Galactose Oxidase (GAO) to oxidize the C6 hydroxyl group of the Gal residue in the artificially introduced LacNAc glycan (as obtained in example 7) on the nanobody of interest. This enzymatic oxidation also creates a free aldehyde group, which can be linked to a molecule of interest via oxime ligation, hydrazone ligation or reductive amination (Park, A. et al., *Endocrinology* 154, 2013), as described in example 7. The schematic outline of GAO-based LacNAc oxidation, coupled with subsequent oxime ligation, is illustrated in FIG. 19. In a similar approach, a mutant form of Galactose Oxidase (GAO-F2; see Rannes, J. B. et al. (2011), *J. Am. Chem. Soc.*, 133, 8436-8439) can be used to oxidize the C6 hydroxyl group of GlcNAc; a cargo of interest can then be directly linked to the GlcNAc residue. The schematic outline of GAO-F2-based GlcNAc oxidation, coupled with subsequent oxime ligation, is illustrated in FIG. 20.

Briefly, GBP carrying an R86N mutation was recombinantly produced in *Pichia* GlycoDelete cells or *Pichia* GlycoDelete cells which co-express a galactosyltransferase. Proteins were purified, yielding a mixture of non-glycosylated protein and protein carrying a single GlcNAc residue (*Pichia*-GlycoDelete), or a mixture of non-glycosylated protein and protein carrying GlcNAc or LacNAc (*Pichia*-GlycoDelete with galactosyltransferase co-expression). The purified protein derived from *Pichia*-GlycoDelete with galactosyltransferase co-expression was then oxidized with GAO and linked to a short biotinylated and aminooxy-modified PEG chain in a one-pot reaction. Mass spec analysis showed that the PEG chain was selectively linked to LacNAc-carrying GBP. The purified protein derived from *Pichia*-GlycoDelete was oxidized with GAO-F2 and linked to a short biotinylated and aminooxy-modified PEG chain in a one-pot reaction. Mass spec analysis showed that the PEG chain was selectively linked to GlcNAc-carrying GBP.

Figure 21:
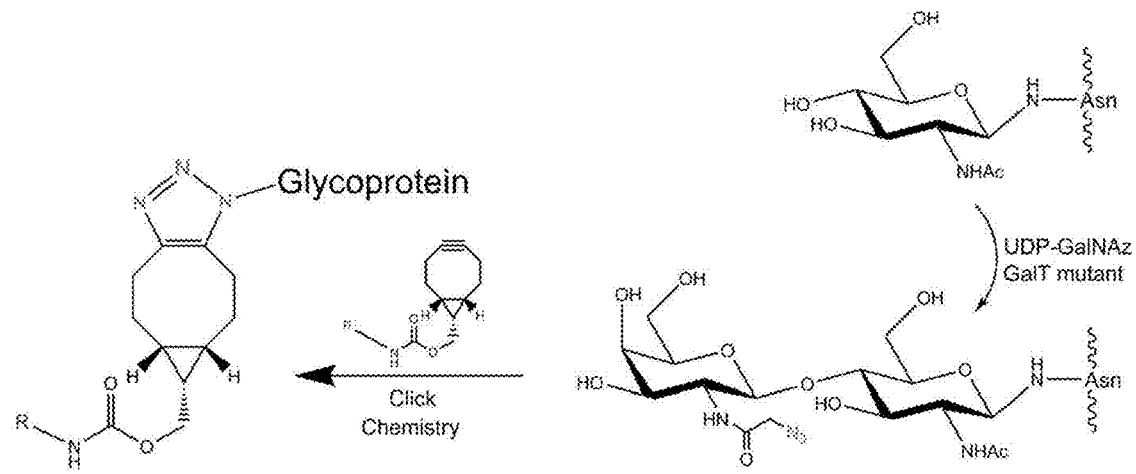
FIG. 21: Schematic outline for chemo-enzymatic coupling of azide-modified form of GalNAc (GalNAz) to a single GlcNAc N-glycan, followed by a click chemistry reaction of the azide with a strained alkyne.
Figure 22:
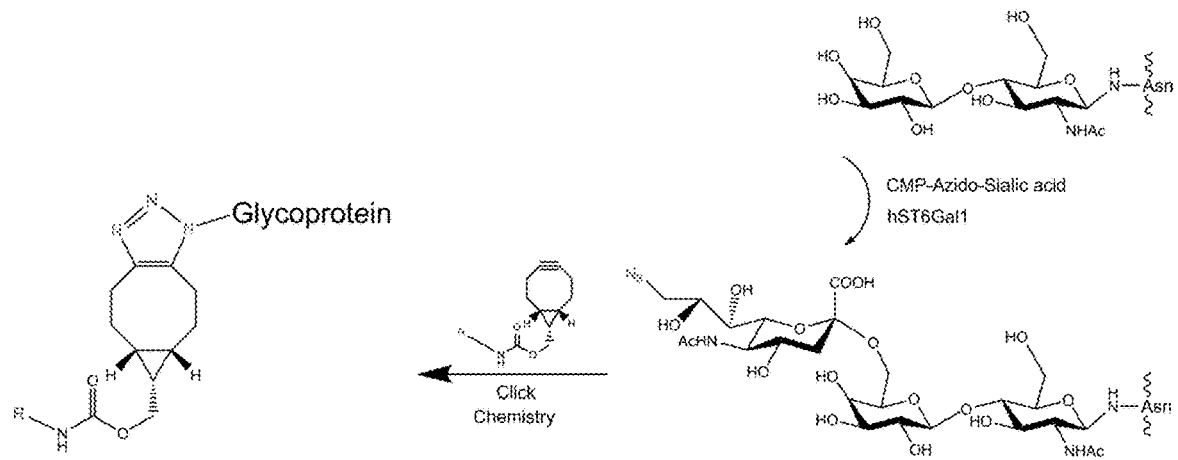
FIG. 22: Schematic outline for chemo-enzymatic coupling of azide-modified form of Sia (AzSia) to a LacNAc N-glycan, followed by a click chemistry reaction of the azide with a strained alkyne.

In an alternative chemo-enzymatic strategy, we can use the enzyme hST6Gal1 (Wu, Z. L., Carbohydrate Research 412, 2015) to conjugate an azide-modified form of Sia (AzSia) to LacNAc, or use a mutated form of human beta-1,4-galactosyl/GalNAc transferase (van Geel, R., *Bioconjug. Chem.* 26, 2015) to conjugate an azide-modified form of GalNAc (GalNAz) to the single GlcNAc N-glycan present on our nanobody of interest. Via the azide function, the introduced GalNAz/AzSia on the nanobody can homogeneously and site-specifically be functionalized with a PEG chain or another molecule of interest employing click chemistry (e.g. copper-free azide-alkyne cycloaddition reaction). The schematic outline is illustrated in FIGS. 21 (GalNAz) and 22 (AzSia).

Azide-modified GlcNAc, LacNAc, and sialyl-LacNAc glycans may also be obtained by feeding azide-modified monosaccharide precursors (GlcNAz, GalNAz, AzSia) to the GlycoDelete cells producing the protein of interest; this allows subsequent site-specific functionalization via click chemistry.

Briefly, GBP carrying an R86N mutation was recombinantly produced in *Pichia* GlycoDelete cells or *Pichia* GlycoDelete cells which co-express a galactosyltransferase. Proteins were purified, yielding a mixture of non-glycosylated protein and protein carrying a single GlcNAc residue (*Pichia*-GlycoDelete), or a mixture of non-glycosylated protein and protein carrying GlcNAc or LacNAc (*Pichia*-GlycoDelete with galactosyltransferase co-expression). The purified protein derived from *Pichia*-GlycoDelete with galactosyltransferase co-expression was then incubated with CMP-Azido-Sialic Acid and recombinant hST6Gal1 enzyme to add an AzSia residue to the LacNAc chain, and subsequently subjected to a click reaction with a short biotinylated and DBCO-modified PEG chain. Mass spec analysis showed that the PEG chain was selectively linked to LacNAc-carrying GBP. The purified protein derived from *Pichia*-GlycoDelete was incubated with UDP-GalNAz and a mutated form of human beta-1,4-galactosyl/GalNAc transferase enzyme to add a GalNAz residue to the single GlcNAc glycan, and subsequently subjected to a click reaction with a short biotinylated and DBCO-modified PEG chain. Mass spec analysis showed that the PEG chain was selectively linked to GlcNAc-carrying GBP.

The invention claimed is:

1. A nucleotide sequence encoding a polypeptide, wherein the polypeptide comprises:
    an immunoglobulin single variable domain (ISVD) derived from a camelid heavy chain antibody, wherein the ISVD comprises an amino acid sequence that comprises 4 framework regions (FR) and 3 complementarity determining regions (CDR) according to the following formula (1):

FR1-CDR1-FR2-CDR2-FR3-CDR3-FR4     (1), wherein the ISVD further comprises a N-glycosylation acceptor site present on an amino acid selected from amino acids 83 to 88 of the ISVD according to the AHo numbering convention.

2. The nucleotide sequence of claim 1, wherein the ISVD comprises at least one additional glycosylation acceptor site in the ISVD.

3. The nucleotide sequence of claim 1, wherein the nucleotide sequences is present in an expression vector.

4. The nucleotide sequence of claim 3, wherein the expression vector is present in a cell.

5. The cell of claim 4, wherein the cell is a higher eukaryotic cell, a mammalian cell, a plant cell, a lower eukaryotic cell, a filamentous fungus cell, a yeast cell, or a prokaryotic cell.

6. The cell of claim 4, wherein the cell is a glyco-engineered cell.

7. A polypeptide comprising the ISVD encoded by the nucleotide sequence of claim 1.

8. The polypeptide of claim 7,
    wherein the polypeptide is glycosylated and comprises one or more glycans, and
    wherein the glycans have a terminal GlcNAc, GalNAc, Galactose, Sialic Acid, Glucose, Glucosamine, Galactosamine, Bacillosamine, GalNAz, GlcNAz, azido-sialic acid, Mannose or Mannose-6-P sugar or a chemically modified monosaccharide.

9. The polypeptide comprising an ISVD of claim 7, wherein the glycosylation consists of one or more glycans selected from the group consisting of GlcNAc, LacNAc, sialyl-LacNAc, Man5GlcNAc2, Man8GlcNAc2, Man9GlcNAc2, hyper-mannosylated glycans, mannose-6-phosphate glycans, complex glycans, hybrid glycans, GlcNAz, GlcNAc-GalNAz, azido-sialic acid-LacNAc, and chemically modified glycans.

10. A method of glycan-specific conjugation, the method comprising:
    conjugating a moiety to a glycan present on the polypeptide of claim 8.

11. The polypeptide of claim 7 further comprising a moiety conjugated to the polypeptide.

12. The polypeptide of claim 11 wherein the moiety is conjugated to an N-linked glycan.

13. The polypeptide of claim 11, wherein the moiety comprises a half-life extending moiety, a therapeutic agent, a detection unit, or a targeting moiety.

* * * * *

SEQUENCE LISTING

<160> NUMBER OF SEQ ID NOS: 62

<210> SEQ ID NO 1
<211> LENGTH: 115
<212> TYPE: PRT
<213> ORGANISM: Artificial Sequence
<220> FEATURE:
<223> OTHER INFORMATION: nanobody

<400> SEQUENCE: 1

Gln Leu Gln Glu Ser Gly Gly Gly Leu Val Gln Pro Gly Gly Ser Leu
1               5                   10                  15

Arg Leu Ser Cys Ala Ala Ser Gly Phe Thr Phe Asn Asn Tyr Trp Met
                20                  25                  30

Tyr Trp Val Arg Arg Ala Pro Gly Lys Gly Leu Glu Trp Val Ser Met
            35                  40                  45

Ile Asn Pro Gly Gly Ile Ile Thr Lys Tyr Ala Glu Ser Val Lys Gly
        50                  55                  60

Arg Phe Thr Ile Ser Arg Asp Asn Ala Lys Asn Thr Leu Tyr Leu Gln
65                  70                  75                  80

Met Asn Ser Leu Thr Ser Glu Asp Thr Ala Val Tyr Tyr Cys Ala Lys
                85                  90                  95

Asp Trp Ala Thr Gly Leu Ala Lys Lys Gly Gln Gly Thr Gln Val Thr
            100                 105                 110

Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: CDR1

<400> SEQUENCE: 2

Gly Phe Thr Phe Asn Asn Tyr Trp
1               5

<210> SEQ ID NO 3
<211> LENGTH: 9
<212> TYPE: PRT
<213> ORGANISM: Artificial Sequence
<220> FEATURE:
<223> OTHER INFORMATION: CDR2

<400> SEQUENCE: 3

Ile Asn Pro Gly Gly Ile Ile Thr Lys
1               5

<210> SEQ ID NO 4
<211> LENGTH: 9
<212> TYPE: PRT
<213> ORGANISM: Artificial Sequence
<220> FEATURE:
<223> OTHER INFORMATION: CDR3

<400> SEQUENCE: 4

Ala Lys Asp Trp Ala Thr Gly Leu Ala
1               5

<210> SEQ ID NO 5
<211> LENGTH: 23
<212> TYPE: PRT

-continued

```
<213> ORGANISM: Artificial Sequence
<220> FEATURE:
<223> OTHER INFORMATION: FR1

<400> SEQUENCE: 5

Gln Leu Gln Glu Ser Gly Gly Gly Leu Val Gln Pro Gly Gly Ser Leu
1               5                   10                  15

Arg Leu Ser Cys Ala Ala Ser
            20

<210> SEQ ID NO 6
<211> LENGTH: 17
<212> TYPE: PRT
<213> ORGANISM: Artificial Sequence
<220> FEATURE:
<223> OTHER INFORMATION: FR2

<400> SEQUENCE: 6

Met Tyr Trp Val Arg Arg Ala Pro Gly Lys Gly Leu Glu Trp Val Ser
1               5                   10                  15

Met

<210> SEQ ID NO 7
<211> LENGTH: 37
<212> TYPE: PRT
<213> ORGANISM: Artificial Sequence
<220> FEATURE:
<223> OTHER INFORMATION: FR3

<400> SEQUENCE: 7

Tyr Ala Glu Ser Val Lys Gly Arg Phe Thr Ile Ser Arg Asp Asn Ala
1               5                   10                  15

Lys Asn Thr Leu Tyr Leu Gln Met Asn Ser Leu Thr Ser Glu Asp Thr
            20                  25                  30

Ala Val Tyr Tyr Cys
        35

<210> SEQ ID NO 8
<211> LENGTH: 12
<212> TYPE: PRT
<213> ORGANISM: Artificial Sequence
<220> FEATURE:
<223> OTHER INFORMATION: FR4

<400> SEQUENCE: 8

Lys Lys Gly Gln Gly Thr Gln Val Thr Val Ser Ser
1               5                   10

<210> SEQ ID NO 9
<211> LENGTH: 121
<212> TYPE: PRT
<213> ORGANISM: Artificial Sequence
<220> FEATURE:
<223> OTHER INFORMATION: Nanobody

<400> SEQUENCE: 9

Gln Val Gln Leu Val Glu Ser Gly Gly Gly Ala Leu Val Gln Pro Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45
```

-continued

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
                100                 105                 110

Val Ser Ser His His His His His His
        115                 120

<210> SEQ ID NO 10
<211> LENGTH: 8
<212> TYPE: PRT
<213> ORGANISM: Artificial Sequence
<220> FEATURE:
<223> OTHER INFORMATION: CDR1

<400> SEQUENCE: 10

Gly Phe Pro Val Asn Arg Tyr Ser
1               5

<210> SEQ ID NO 11
<211> LENGTH: 9
<212> TYPE: PRT
<213> ORGANISM: Artificial Sequence
<220> FEATURE:
<223> OTHER INFORMATION: CDR2

<400> SEQUENCE: 11

Met Ser Ser Ala Gly Asp Arg Ser Ser
1               5

<210> SEQ ID NO 12
<211> LENGTH: 7
<212> TYPE: PRT
<213> ORGANISM: Artificial Sequence
<220> FEATURE:
<223> OTHER INFORMATION: CDR3

<400> SEQUENCE: 12

Asn Val Asn Val Gly Phe Glu
1               5

<210> SEQ ID NO 13
<211> LENGTH: 25
<212> TYPE: PRT
<213> ORGANISM: Artificial Sequence
<220> FEATURE:
<223> OTHER INFORMATION: FR1

<400> SEQUENCE: 13

Gln Val Gln Leu Val Glu Ser Gly Gly Ala Leu Val Gln Pro Gly Gly
1               5                   10                  15

Ser Leu Arg Leu Ser Cys Ala Ala Ser
            20                  25

<210> SEQ ID NO 14
<211> LENGTH: 17
<212> TYPE: PRT
<213> ORGANISM: Artificial Sequence
<220> FEATURE:
<223> OTHER INFORMATION: FR2

<400> SEQUENCE: 14

```
Met Arg Trp Tyr Arg Gln Ala Pro Gly Lys Glu Arg Glu Trp Val Ala
1               5                   10                  15
Gly

<210> SEQ ID NO 15
<211> LENGTH: 37
<212> TYPE: PRT
<213> ORGANISM: Artificial Sequence
<220> FEATURE:
<223> OTHER INFORMATION: FR3

<400> SEQUENCE: 15

Tyr Glu Asp Ser Val Lys Gly Arg Phe Thr Ile Ser Arg Asp Asp Ala
1               5                   10                  15

Arg Asn Thr Val Tyr Leu Gln Met Asn Ser Leu Lys Pro Glu Asp Thr
                20                  25                  30

Ala Val Tyr Tyr Cys
                35

<210> SEQ ID NO 16
<211> LENGTH: 12
<212> TYPE: PRT
<213> ORGANISM: Artificial Sequence
<220> FEATURE:
<223> OTHER INFORMATION: FR4

<400> SEQUENCE: 16

Tyr Trp Gly Gln Gly Thr Gln Val Thr Val Ser Ser
1               5                   10

<210> SEQ ID NO 17
<211> LENGTH: 129
<212> TYPE: PRT
<213> ORGANISM: Artificial Sequence
<220> FEATURE:
<223> OTHER INFORMATION: Nanobody

<400> SEQUENCE: 17

Gln Val Gln Leu Gln Glu Ser Gly Gly Gly Leu Val Gln Pro Gly Gly
1               5                   10                  15

Ser Leu Arg Leu Ser Cys Val Ala Ser Gly Ser Ile Phe Ser Ile Asn
                20                  25                  30

Ala Met Gly Trp Tyr Arg Gln Ala Pro Gly Lys Gln Arg Glu Leu Val
                35                  40                  45

Ala Ala Ile Ser Ser Gly Gly Arg Thr Asn Tyr Ala Asp Ser Val Lys
        50                  55                  60

Gly Arg Phe Thr Ile Ser Arg Asp Asn Ala Lys Asn Thr Val His Leu
65                  70                  75                  80

Gln Met Asn Ser Leu Lys Pro Glu Asp Thr Ala Val Tyr Tyr Cys Asn
                85                  90                  95

Val Gly Ser Trp Gly Phe Arg Ser His Ser Tyr Leu Ser Gly Ser Ser
                100                 105                 110

Trp Gly Gln Gly Thr Gln Val Thr Val Ser Ser His His His His His
        115                 120                 125

His

<210> SEQ ID NO 18
<211> LENGTH: 8
<212> TYPE: PRT
<213> ORGANISM: Artificial Sequence
```

```
<220> FEATURE:
<223> OTHER INFORMATION: CDR1

<400> SEQUENCE: 18

Gly Ser Ile Phe Ser Ile Asn Ala
1               5

<210> SEQ ID NO 19
<211> LENGTH: 8
<212> TYPE: PRT
<213> ORGANISM: Artificial Sequence
<220> FEATURE:
<223> OTHER INFORMATION: CDR2

<400> SEQUENCE: 19

Ile Ser Ser Gly Gly Arg Thr Asn
1               5

<210> SEQ ID NO 20
<211> LENGTH: 16
<212> TYPE: PRT
<213> ORGANISM: Artificial Sequence
<220> FEATURE:
<223> OTHER INFORMATION: CDR3

<400> SEQUENCE: 20

Asn Val Gly Ser Trp Gly Phe Arg Ser His Ser Tyr Leu Ser Gly Ser
1               5                   10                  15

<210> SEQ ID NO 21
<211> LENGTH: 25
<212> TYPE: PRT
<213> ORGANISM: Artificial Sequence
<220> FEATURE:
<223> OTHER INFORMATION: FR1

<400> SEQUENCE: 21

Gln Val Gln Leu Gln Glu Ser Gly Gly Gly Leu Val Gln Pro Gly Gly
1               5                   10                  15

Ser Leu Arg Leu Ser Cys Val Ala Ser
            20                  25

<210> SEQ ID NO 22
<211> LENGTH: 17
<212> TYPE: PRT
<213> ORGANISM: Artificial Sequence
<220> FEATURE:
<223> OTHER INFORMATION: FR2

<400> SEQUENCE: 22

Met Gly Trp Tyr Arg Gln Ala Pro Gly Lys Gln Arg Glu Leu Val Ala
1               5                   10                  15

Ala

<210> SEQ ID NO 23
<211> LENGTH: 37
<212> TYPE: PRT
<213> ORGANISM: Artificial Sequence
<220> FEATURE:
<223> OTHER INFORMATION: FR3

<400> SEQUENCE: 23

Tyr Ala Asp Ser Val Lys Gly Arg Phe Thr Ile Ser Arg Asp Asn Ala
1               5                   10                  15

Lys Asn Thr Val His Leu Gln Met Asn Ser Leu Lys Pro Glu Asp Thr
```

```
                    20                  25                  30

Ala Val Tyr Tyr Cys
            35

<210> SEQ ID NO 24
<211> LENGTH: 12
<212> TYPE: PRT
<213> ORGANISM: Artificial Sequence
<220> FEATURE:
<223> OTHER INFORMATION: FR4

<400> SEQUENCE: 24

Ser Trp Gly Gln Gly Thr Gln Val Thr Val Ser Ser
1               5                  10

<210> SEQ ID NO 25
<211> LENGTH: 135
<212> TYPE: PRT
<213> ORGANISM: Artificial Sequence
<220> FEATURE:
<223> OTHER INFORMATION: Nanobody

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Tyr Ile Gly Trp Phe Arg Gln Ala Pro Gly Lys Glu Arg Glu Ala Val
        35                  40                  45

Ser Cys Ile Ser Gly Ser Gly Ser Thr Tyr Tyr Pro Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Ile Arg Ser Ser Ser Trp Gly Gly Cys Val His Tyr Gly Met
            100                 105                 110

Asp Tyr Trp Gly Lys Gly Thr Gln Val Thr Val Ser Ser Gly Ser His
        115                 120                 125

His His His His His His His
    130                 135

<210> SEQ ID NO 26
<211> LENGTH: 135
<212> TYPE: PRT
<213> ORGANISM: Artificial Sequence
<220> FEATURE:
<223> OTHER INFORMATION: Nanobody

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Tyr Ile Gly Trp Phe Arg Gln Ala Pro Gly Lys Glu Arg Glu Gly Val
        35                  40                  45

Ser Cys Ile Ser Ser Ser His Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Val Tyr Tyr Cys
                 85                  90                  95

Ala Thr Val Ala Val Ala His Phe Arg Gly Cys Gly Val Asp Gly Met
            100                 105                 110

Asp Tyr Trp Gly Lys Gly Thr Gln Val Thr Val Ser Ser Gly Ser His
        115                 120                 125

His His His His His His His
    130             135
```

```
<210> SEQ ID NO 27
<211> LENGTH: 5
<212> TYPE: PRT
<213> ORGANISM: Artificial Sequence
<220> FEATURE:
<223> OTHER INFORMATION: linker

<400> SEQUENCE: 27

Gly Gly Gly Ser Ser
1               5
```

```
<210> SEQ ID NO 28
<211> LENGTH: 17
<212> TYPE: PRT
<213> ORGANISM: Artificial Sequence
<220> FEATURE:
<223> OTHER INFORMATION: artificial N-terminal glyco-tag

<400> SEQUENCE: 28

Gln Ala Asp Asp Ala Asn Ala Thr Val Gln Leu Val Glu Ser Gly Gly
1               5                   10                  15

Ala
```

```
<210> SEQ ID NO 29
<211> LENGTH: 10
<212> TYPE: PRT
<213> ORGANISM: Artificial Sequence
<220> FEATURE:
<223> OTHER INFORMATION: part of wildtype GBP

<400> SEQUENCE: 29

Gln Val Gln Leu Val Glu Ser Gly Gly Ala
1               5                   10
```

```
<210> SEQ ID NO 30
<211> LENGTH: 31
<212> TYPE: PRT
<213> ORGANISM: Artificial Sequence
<220> FEATURE:
<223> OTHER INFORMATION: C-terminal glyco-HIS-tag

<400> SEQUENCE: 30

Val Ser Ser Leu Gln Ala Ala Ala Ala Ala Asn Ala Thr Val Ala
1               5                   10                  15

Ala Ala Ser Gly Asp Val Trp Asp Ile His His His His His His
                20                  25                  30
```

```
<210> SEQ ID NO 31
<211> LENGTH: 9
<212> TYPE: PRT
<213> ORGANISM: Artificial Sequence
<220> FEATURE:
<223> OTHER INFORMATION: Part of wildtype GBP

<400> SEQUENCE: 31
```

Val Ser Ser His His His His His
1               5

<210> SEQ ID NO 32
<211> LENGTH: 121
<212> TYPE: PRT
<213> ORGANISM: Artificial Sequence
<220> FEATURE:
<223> OTHER INFORMATION: Mutated GBP

<400> SEQUENCE: 32

Gln Val Gln Leu Val Glu Ser Gly Gly Ala Leu Val Asn Ala Thr Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser His His His His His His
        115                 120

<210> SEQ ID NO 33
<211> LENGTH: 121
<212> TYPE: PRT
<213> ORGANISM: Artificial Sequence
<220> FEATURE:
<223> OTHER INFORMATION: Mutated GBP

<400> SEQUENCE: 33

Gln Val Gln Leu Val Glu Ser Gly Gly Ala Leu Val Gln Asn Gly Thr
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser His His His His His His
        115                 120

<210> SEQ ID NO 34
<211> LENGTH: 121
<212> TYPE: PRT
<213> ORGANISM: Artificial Sequence
<220> FEATURE:
<223> OTHER INFORMATION: Mutated GBP

<400> SEQUENCE: 34

```
Gln Val Gln Leu Val Glu Ser Gly Gly Ala Leu Val Gln Pro Asn Gly
1               5                   10                  15

Thr Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
            85                  90                  95

Asn Val Asn Val Gly Phe Glu Tyr Trp Gly Gln Gly Thr Gln Val Thr
            100                 105                 110

Val Ser Ser His His His His His His
            115                 120
```

<210> SEQ ID NO 35
<211> LENGTH: 121
<212> TYPE: PRT
<213> ORGANISM: Artificial Sequence
<220> FEATURE:
<223> OTHER INFORMATION: Mutated GBP

<400> SEQUENCE: 35

```
Gln Val Gln Leu Val Glu Ser Gly Gly Ala Leu Val Gln Pro Gly Gly
1               5                   10                  15

Ser Leu Arg Leu Ser Cys Ala Ala Ser Asn Phe Thr Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
            85                  90                  95

Asn Val Asn Val Gly Phe Glu Tyr Trp Gly Gln Gly Thr Gln Val Thr
            100                 105                 110

Val Ser Ser His His His His His His
            115                 120
```

<210> SEQ ID NO 36
<211> LENGTH: 121
<212> TYPE: PRT
<213> ORGANISM: Artificial Sequence
<220> FEATURE:
<223> OTHER INFORMATION: Mutated GBP

<400> SEQUENCE: 36

```
Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Asn Gly Thr Glu Arg Glu Trp Val
        35                  40                  45
```

```
Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
                100                 105                 110

Val Ser Ser His His His His His His
        115                 120

<210> SEQ ID NO 37
<211> LENGTH: 121
<212> TYPE: PRT
<213> ORGANISM: Artificial Sequence
<220> FEATURE:
<223> OTHER INFORMATION: Mutated GBP

<400> SEQUENCE: 37

Gln Val Gln Leu Val Glu Ser Gly Gly Ala Leu Val Gln Pro Gly Gly
 1                5                  10                 15

Ser Leu Arg Leu Ser Cys Ala Ala Ser Gly Phe Pro Val Asn Arg Tyr
                20                  25                  30

Ser Met Arg Trp Tyr Arg Gln Ala Pro Asn Lys Thr Arg Glu Trp Val
            35                  40                  45

Ala Gly Met Ser Ser Ala Gly Asp Arg Ser Tyr Glu Asp Ser Val
    50                  55                  60

Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
                100                 105                 110

Val Ser Ser His His His His His His
        115                 120

<210> SEQ ID NO 38
<211> LENGTH: 121
<212> TYPE: PRT
<213> ORGANISM: Artificial Sequence
<220> FEATURE:
<223> OTHER INFORMATION: Mutated GBP

<400> SEQUENCE: 38

Gln Val Gln Leu Val Glu Ser Gly Gly Ala Leu Val Gln Pro Gly Gly
 1                5                  10                 15

Ser Leu Arg Leu Ser Cys Ala Ala Ser Gly Phe Pro Val Asn Arg Tyr
                20                  25                  30

Ser Met Arg Trp Tyr Arg Gln Ala Pro Gly Lys Glu Arg Glu Trp Val
            35                  40                  45

Ala Gly Met Ser Ser Ala Gly Asp Arg Ser Ser Tyr Glu Asp Asn Val
    50                  55                  60

Thr Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                 85                  90                  95

Asn Val Asn Val Gly Phe Glu Tyr Trp Gly Gln Gly Thr Gln Val Thr
                100                 105                 110
```

```
Val Ser Ser His His His His His
        115                 120

<210> SEQ ID NO 39
<211> LENGTH: 121
<212> TYPE: PRT
<213> ORGANISM: Artificial Sequence
<220> FEATURE:
<223> OTHER INFORMATION: Mutated GBP

<400> SEQUENCE: 39

Gln Val Gln Leu Val Glu Ser Gly Gly Ala Leu Val Gln Pro Gly Gly
1               5                  10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Asn Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser His His His His His His
        115                 120

<210> SEQ ID NO 40
<211> LENGTH: 121
<212> TYPE: PRT
<213> ORGANISM: Artificial Sequence
<220> FEATURE:
<223> OTHER INFORMATION: Mutated GBP

<400> SEQUENCE: 40

His Gln Val Gln Leu Val Glu Ser Gly Gly Ala Leu Val Gln Pro Gly
1               5                  10                  15

Gly Ser Leu Arg Leu Ser Cys Ala Ala Ser Gly Phe Pro Val Asn Arg
            20                  25                  30

Tyr Ser Met Arg Trp Tyr Arg Gln Ala Pro Gly Lys Glu Arg Glu Trp
        35                  40                  45

Val Ala Gly Met Ser Ser Ala Gly Asp Arg Ser Ser Tyr Glu Asp Ser
    50                  55                  60

Val Lys Gly Arg Phe Thr Ile Ser Arg Asp Asp Ala Arg Asn Thr Val
65                  70                  75                  80

Tyr Leu Gln Met Asn Ser Leu Lys Pro Glu Asp Thr Ala Val Tyr Tyr
                85                  90                  95

Cys Asn Val Asn Val Gly Phe Glu Tyr Asn Gly Thr Gly Thr Gln Val
            100                 105                 110

Thr Val Ser Ser His His His His His
        115                 120

<210> SEQ ID NO 41
<211> LENGTH: 60
<212> TYPE: PRT
<213> ORGANISM: Artificial Sequence
<220> FEATURE:
<223> OTHER INFORMATION: Fragment of SEQ ID NO:9
```

```
<400> SEQUENCE: 41

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60

<210> SEQ ID NO 42
<211> LENGTH: 60
<212> TYPE: PRT
<213> ORGANISM: Artificial Sequence
<220> FEATURE:
<223> OTHER INFORMATION: Mutated GBP

<400> SEQUENCE: 42

Ala Ala Ser Asn Phe Thr Val Asn Arg Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60

<210> SEQ ID NO 43
<211> LENGTH: 60
<212> TYPE: PRT
<213> ORGANISM: Artificial Sequence
<220> FEATURE:
<223> OTHER INFORMATION: Mutated GBP

<400> SEQUENCE: 43

Ala Ala Ser Gly Asn Ala Thr Asn Arg Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60

<210> SEQ ID NO 44
<211> LENGTH: 60
<212> TYPE: PRT
<213> ORGANISM: Artificial Sequence
<220> FEATURE:
<223> OTHER INFORMATION: Mutated GBP

<400> SEQUENCE: 44

Ala Ala Ser Gly Phe Asn Val Thr Arg Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60
```

<210> SEQ ID NO 45
<211> LENGTH: 60
<212> TYPE: PRT
<213> ORGANISM: Artificial Sequence
<220> FEATURE:
<223> OTHER INFORMATION: Mutated GBP

<400> SEQUENCE: 45

Ala Ala Ser Gly Phe Ala Asn Asn Thr Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60

<210> SEQ ID NO 46
<211> LENGTH: 60
<212> TYPE: PRT
<213> ORGANISM: Artificial Sequence
<220> FEATURE:
<223> OTHER INFORMATION: Mutated GBP

<400> SEQUENCE: 46

Ala Ala Ser Gly Phe Pro Val Asn Arg Thr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60

<210> SEQ ID NO 47
<211> LENGTH: 60
<212> TYPE: PRT
<213> ORGANISM: Artificial Sequence
<220> FEATURE:
<223> OTHER INFORMATION: Mutated GBP

<400> SEQUENCE: 47

Ala Ala Ser Gly Phe Pro Val Asn Asn Tyr Thr Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
    50                  55                  60

<210> SEQ ID NO 48
<211> LENGTH: 60
<212> TYPE: PRT
<213> ORGANISM: Artificial Sequence
<220> FEATURE:
<223> OTHER INFORMATION: Mutated GBP

<400> SEQUENCE: 48

Ala Ala Ser Gly Phe Pro Val Asn Arg Asn Ser Thr Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
50                  55                  60

<210> SEQ ID NO 49
<211> LENGTH: 60
<212> TYPE: PRT
<213> ORGANISM: Artificial Sequence
<220> FEATURE:
<223> OTHER INFORMATION: Mutated GBP

<400> SEQUENCE: 49

Ala Ala Ser Gly Phe Pro Val Asn Arg Tyr Asn Met Thr Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Arg Asn Thr Val Tyr Leu
50                  55                  60

<210> SEQ ID NO 50
<211> LENGTH: 63
<212> TYPE: PRT
<213> ORGANISM: Artificial Sequence
<220> FEATURE:
<223> OTHER INFORMATION: Mutated GBP

<400> SEQUENCE: 50

Ala Ala Ser Gly Phe Pro Val Asn Arg Asn Ala Thr Tyr Ser Met Arg
1               5                   10                  15

Trp Tyr Arg Gln Ala Pro Gly Lys Glu Arg Glu Trp Val Ala Gly Met
            20                  25                  30

Ser Ser Ala Gly Asp Arg Ser Ser Tyr Glu Asp Ser Val Lys Gly Arg
        35                  40                  45

Phe Thr Ile Ile Ser Arg Asp Asp Ala Arg Asn Thr Val Tyr Leu
50                  55                  60

<210> SEQ ID NO 51
<211> LENGTH: 66
<212> TYPE: PRT
<213> ORGANISM: Artificial Sequence
<220> FEATURE:
<223> OTHER INFORMATION: Mutated GBP

<400> SEQUENCE: 51

Ala Ala Ser Gly Phe Pro Val Asn Arg Asp Asn Ala Asn Ala Thr Tyr
1               5                   10                  15

Ser Met Arg Trp Tyr Arg Gln Ala Pro Gly Lys Glu Arg Glu Trp Val
            20                  25                  30

Ala Gly Met Ser Ser Ala Gly Asp Arg Ser Ser Tyr Glu Asp Ser Val
        35                  40                  45

Lys Gly Arg Phe Thr Ile Ile Ser Arg Asp Asp Ala Arg Asn Thr Val
    50                  55                  60

Tyr Leu
65

<210> SEQ ID NO 52
<211> LENGTH: 63
<212> TYPE: PRT
<213> ORGANISM: Artificial Sequence
<220> FEATURE:
<223> OTHER INFORMATION: Mutated GBP

<400> SEQUENCE: 52

Ala Ala Ser Asn Ala Thr Gly Phe Pro Val Asn Arg Tyr Ser Met Arg
1               5                   10                  15

Trp Tyr Arg Gln Ala Pro Gly Lys Glu Arg Glu Trp Val Ala Gly Met
                20                  25                  30

Ser Ser Ala Gly Asp Arg Ser Ser Tyr Glu Asp Ser Val Lys Gly Arg
            35                  40                  45

Phe Thr Ile Ile Ser Arg Asp Asp Ala Arg Asn Thr Val Tyr Leu
        50                  55                  60

<210> SEQ ID NO 53
<211> LENGTH: 60
<212> TYPE: PRT
<213> ORGANISM: Artificial Sequence
<220> FEATURE:
<223> OTHER INFORMATION: Mutated GBP

<400> SEQUENCE: 53

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
                20                  25                  30

Gly Asp Arg Ser Ser Tyr Glu Asp Ser Val Lys Gly Arg Phe Thr Ile
            35                  40                  45

Ile Ser Arg Asn Asp Thr Arg Asn Thr Val Tyr Leu
        50                  55                  60

<210> SEQ ID NO 54
<211> LENGTH: 60
<212> TYPE: PRT
<213> ORGANISM: Artificial Sequence
<220> FEATURE:
<223> OTHER INFORMATION: Mutated GBP

<400> SEQUENCE: 54

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
                20                  25                  30

Gly Asp Arg Ser Ser Tyr Glu Asp Ser Val Lys Gly Arg Phe Thr Ile
            35                  40                  45

Ile Ser Arg Asp Asn Ala Thr Asn Thr Val Tyr Leu
        50                  55                  60

<210> SEQ ID NO 55
<211> LENGTH: 60
<212> TYPE: PRT
<213> ORGANISM: Artificial Sequence
<220> FEATURE:
<223> OTHER INFORMATION: Mutated GBP

<400> SEQUENCE: 55

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
                20                  25                  30

Gly Asp Arg Ser Ser Tyr Glu Asp Ser Val Lys Gly Arg Phe Thr Ile
            35                  40                  45

Ile Ser Arg Asp Asp Asn Arg Thr Thr Val Tyr Leu
        50                  55                  60

<210> SEQ ID NO 56
<211> LENGTH: 60
<212> TYPE: PRT
<213> ORGANISM: Artificial Sequence
<220> FEATURE:
<223> OTHER INFORMATION: Mutated GBP

<400> SEQUENCE: 56

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
                20                  25                  30

Gly Asp Arg Ser Ser Tyr Glu Asp Ser Val Lys Gly Arg Phe Thr Ile
            35                  40                  45

Ile Ser Arg Asp Asp Ala Thr Asn Thr Val Tyr Leu
        50                  55                  60

<210> SEQ ID NO 57
<211> LENGTH: 60
<212> TYPE: PRT
<213> ORGANISM: Artificial Sequence
<220> FEATURE:
<223> OTHER INFORMATION: Mutated GBP

<400> SEQUENCE: 57

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
                20                  25                  30

Gly Asp Arg Ser Ser Tyr Glu Asp Ser Val Lys Gly Arg Phe Thr Ile
            35                  40                  45

Ile Ser Arg Asp Asp Ala Arg Asn Thr Thr Tyr Leu
        50                  55                  60

<210> SEQ ID NO 58
<211> LENGTH: 60
<212> TYPE: PRT
<213> ORGANISM: Artificial Sequence
<220> FEATURE:
<223> OTHER INFORMATION: Mutated GBP

<400> SEQUENCE: 58

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
                20                  25                  30

Gly Asp Arg Ser Ser Tyr Glu Asp Ser Val Lys Gly Arg Phe Thr Ile
            35                  40                  45

Ile Ser Arg Asp Asp Ala Arg Asn Asn Val Thr Leu
        50                  55                  60

<210> SEQ ID NO 59
<211> LENGTH: 63
<212> TYPE: PRT

```
<213> ORGANISM: Artificial Sequence
<220> FEATURE:
<223> OTHER INFORMATION: Mutated GBP

<400> SEQUENCE: 59

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asn Ala Thr Asp Asp Ala Arg Asn Thr Val Tyr Leu
    50                  55                  60

<210> SEQ ID NO 60
<211> LENGTH: 63
<212> TYPE: PRT
<213> ORGANISM: Artificial Sequence
<220> FEATURE:
<223> OTHER INFORMATION: Mutated GBP

<400> SEQUENCE: 60

Ala Ala Ser Gly Phe Pro Val Asn Arg Tyr Ser Met Arg Trp Tyr Arg
1               5                   10                  15

Gln Ala Pro Gly Lys Glu Arg Glu Trp Val Ala Gly Met Ser Ser Ala
            20                  25                  30

Gly Asp Arg Ser Ser Tyr Glu Asp Ser Val Lys Gly Arg Phe Thr Ile
        35                  40                  45

Ile Ser Arg Asp Asp Ala Asn Ala Thr Arg Asn Thr Val Tyr Leu
    50                  55                  60

<210> SEQ ID NO 61
<211> LENGTH: 18
<212> TYPE: PRT
<213> ORGANISM: Artificial Sequence
<220> FEATURE:
<223> OTHER INFORMATION: Glyco-tagged GBP

<400> SEQUENCE: 61

Gln Ala Asp Asp Ala Asn Ala Thr Gln Val Gln Leu Val Glu Ser Gly
1               5                   10                  15

Gly Ala

<210> SEQ ID NO 62
<211> LENGTH: 31
<212> TYPE: PRT
<213> ORGANISM: Artificial Sequence
<220> FEATURE:
<223> OTHER INFORMATION: Glyco-HIS-tagged GBP

<400> SEQUENCE: 62

Val Ser Ser Leu Gln Ala Ala Ala Ala Ala Asn Ala Thr Val Ala
1               5                   10                  15

Ala Ala Ser Gly Asp Val Trp Asp Ile His His His His His His
            20                  25                  30
```